(12) United States Patent
Li et al.

(10) Patent No.: US 11,857,634 B2
(45) Date of Patent: Jan. 2, 2024

(54) CATIONIC AMPHIPHILIC POLYMERS FOR CODELIVERY OF HYDROPHOBIC AGENTS AND NUCLEIC ACIDS

(71) Applicant: University of Pittsburgh—Of the Commonwealth System of Higher Education, Pittsburgh, PA (US)

(72) Inventors: Song Li, Wexford, PA (US); Jingjing Sun, Pittsburgh, PA (US); Yichao Chen, Pittsburgh, PA (US); Yixian Huang, Pittsburgh, PA (US); Yanhua Liu, Pittsburgh, PA (US); Binfeng Lu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 590 days.

(21) Appl. No.: 17/049,152

(22) PCT Filed: Apr. 20, 2019

(86) PCT No.: PCT/US2019/028418
§ 371 (c)(1),
(2) Date: Oct. 20, 2020

(87) PCT Pub. No.: WO2019/204799
PCT Pub. Date: Oct. 24, 2019

(65) Prior Publication Data
US 2021/0236645 A1    Aug. 5, 2021

Related U.S. Application Data

(60) Provisional application No. 62/660,515, filed on Apr. 20, 2018.

(51) Int. Cl.
| | | |
|---|---|---|
| *A61K 47/58* | (2017.01) | |
| *A61K 47/54* | (2017.01) | |
| *A61K 9/107* | (2006.01) | |
| *A61K 31/65* | (2006.01) | |
| *C12N 15/113* | (2010.01) | |

(52) U.S. Cl.
CPC ............ *A61K 47/58* (2017.08); *A61K 9/1075* (2013.01); *A61K 31/65* (2013.01); *A61K 47/549* (2017.08); *C12N 15/113* (2013.01); *C12N 2310/14* (2013.01); *C12N 2310/351* (2013.01)

(58) Field of Classification Search
CPC .............. C12N 15/113; C12N 2310/14; C12N 2310/351; A61K 47/58; A61K 47/549; A61K 9/1075; A61K 31/65
See application file for complete search history.

(56) References Cited

U.S. PATENT DOCUMENTS

| | | |
|---|---|---|
| 5,763,548 A | 6/1998 | Matyjaszewski |
| 5,789,487 A | 8/1998 | Matyjaszewski |
| 5,807,937 A | 9/1998 | Matyjaszewski |
| 5,945,491 A | 8/1999 | Matyjaszewski |
| 6,111,022 A | 8/2000 | Matyjaszewski |
| 6,121,371 A | 9/2000 | Matyjaszewski |
| 6,124,411 A | 9/2000 | Matyjaszewski |
| 6,162,882 A | 12/2000 | Matyjaszewski |
| 6,407,187 B1 | 6/2002 | Matyjaszewski |
| 6,512,060 B1 | 1/2003 | Matyjaszewski |
| 6,538,091 B1 | 3/2003 | Matyjaszewski |
| 6,541,580 B1 | 4/2003 | Matyjaszewski |
| 6,624,262 B2 | 9/2003 | Matyjaszewski |
| 6,624,263 B2 | 9/2003 | Matyjaszewski |
| 6,627,314 B2 | 9/2003 | Matyjaszewski |
| 6,759,491 B2 | 7/2004 | Matyjaszewski |
| 6,790,919 B2 | 9/2004 | Matyjaszewski |
| 6,887,962 B2 | 5/2005 | Matyjaszewski |
| 7,019,082 B2 | 3/2006 | Matyjaszewski |
| 7,049,373 B2 | 5/2006 | Matyjaszewski |
| 7,064,166 B2 | 6/2006 | Matyjaszewski |
| 7,125,938 B2 | 10/2006 | Matyjaszewski |
| 7,157,530 B2 | 1/2007 | Matyjaszewski |
| 7,332,550 B2 | 2/2008 | Matyjaszewski |
| 7,572,874 B2 | 8/2009 | Matyjaszewski |
| 7,678,869 B2 | 3/2010 | Matyjaszewski |
| 7,795,355 B2 | 9/2010 | Matyjaszewski |
| 7,825,199 B1 | 11/2010 | Matyjaszewski |
| 7,893,173 B2 | 2/2011 | Matyjaszewski |
| 7,893,174 B2 | 2/2011 | Matyjaszewski |
| 8,252,880 B2 | 8/2012 | Matyjaszewski |
| 8,273,823 B2 | 9/2012 | Matyjaszewski |
| 8,349,410 B2 | 1/2013 | Huang |
| 9,855,341 B2 | 1/2018 | Li |
| 9,949,927 B2 | 4/2018 | Xu et al. |
| 10,172,795 B2 | 1/2019 | Gao |

(Continued)

FOREIGN PATENT DOCUMENTS

| | | | |
|---|---|---|---|
| CN | 105985495 | * 10/2016 | ............ C08F 259/08 |
| WO | WO199513059 A1 | 5/1995 | |
| WO | WO2013152227 A1 | 10/2013 | |
| WO | WO2014080251 A1 | 5/2014 | |
| WO | WO2014093631 A1 | 6/2014 | |
| WO | WO2017023667 | 2/2017 | |
| WO | WO2019204799 A1 | 10/2019 | |

OTHER PUBLICATIONS

CN105985495 Machine Translation (Year: 2016).*

(Continued)

*Primary Examiner* — Sean M Basquill
(74) *Attorney, Agent, or Firm* — BARTONY & ASSOCIATES LLC

(57) ABSTRACT

A formulation includes a plurality of polymers including a hydrophobic polymer backbone (for example, formed via radical polymerization), a first plurality of pendant groups attached to the hydrophobic polymer backbone and including at least one cationic group, and a second plurality of pendant groups attached to the hydrophobic polymer backbone and including at least one hydrophilic polymer, a first therapeutic compound, and a second therapeutic compound, wherein the second therapeutic compound is different from the first therapeutic compound and includes a nucleic acid.

19 Claims, 20 Drawing Sheets

(56) References Cited

U.S. PATENT DOCUMENTS

| | | | |
|---|---|---|---|
| 2011/0065807 A1 | 3/2011 | Radovic_Moreno | |
| 2011/0117024 A1 | 5/2011 | Sinko | |
| 2012/0213854 A1* | 8/2012 | Fetzer | A61P 35/00 |
| | | | 977/788 |
| 2012/0309780 A1 | 12/2012 | Kwon | |
| 2014/0155577 A1 | 6/2014 | Parquette | |
| 2015/0197585 A1 | 7/2015 | Epps, III et al. | |
| 2017/0189560 A1 | 7/2017 | Popovtzer et al. | |
| 2018/0214563 A1 | 8/2018 | Li | |
| 2018/0291134 A1 | 10/2018 | Gao et al. | |

OTHER PUBLICATIONS

M. Ogawa et al., Sensitivity to gemcitabine and its metabolizing enzymes in neuroblastoma, Clin. Cancer Res. 11 (2005) 3485-3493.

J.L. Abbruzzese et al., A phase I clinical, plasma, and cellular pharmacology study of gemcitabine, J. Clin. Oncol. 9 (1991) 491-498.

J. Kleeff et al., Pancreatic cancer microenvironment, Int. J. Cancer 121 (2007) 699-705.

S. Lunardi et al., The stromal compartments in pancreatic cancer: are there any therapeutic targets?, Cancer Lett. 343 (2014) 147-155.

US National Library of Medicine. ClinicalTrials.gov [online], https://clinicaltrials.gov/ct2/show/NCT02077881, 2020.

I. Shevchenko et al., Low-dose gemcitabine depletes regulatory T cells and improves survival in the orthotopic Panc02 model of pancreatic cancer, Int. J. Cancer 133 (2013) 98-107.

L. Partecke et al., A syngeneic orthotopic murine model of pancreatic adenocarcinoma in the C57/BL6 mouse using the Panc02 and 6606PDA cell lines, Eur. Surg. Res. 47 (2011) 98-107.

B.-F. Pan et al., Mechanisms of resistance to 6-thioguanine in a murine pancreatic tumor, Cancer Chemother. Pharmacol. 29 (1992) 471-474.

J. Sun et al., Intracellular plasmid DNA delivery by self-assembled nanoparticles of amphiphilic PHML-b-PLLA-b-PHML copolymers and the endocytosis pathway analysis, J. Biomater. Appl. 31 (2016) 606-621.

P.E. Saw et al., Hyper-cell-permeable micelles as a drug delivery carrier for effective cancer therapy, Biomaterials 123 (2017) 118-126.

Matyjaszewski, K., Davis, T. P., Statistical, Gradient, Block, and Graft Copolymers by Controlled/Living Radical Polymerizations; Advances in Polymer Science; vol. 159; 2002, 1-168.

Matyjaszewski, K.,, Davis, T. P., Eds. Handbook of Radical Polymerization; Wiley: Hoboken, 2002, 1-923.

Lu, J. et al., "PEG-Derivatized Embelin as a Nanomicellar Carrier For Delivery of Paclitaxel to Breast and Prostate Cancers", Biomaterials, 2013, vol. 34, No. 5, pp. 1591-1600.

Hou Dy, et al. Inhibition of indoleamine 2,3-dioxygenase in dendritic cells by stereoisomers of 1-methyl-tryptophan correlates with antitumor responses. Cancer research 67, 792-801 (2007).

Liu X, et al. Selective inhibition of IDO1 effectively regulates mediators of antitumor immunity. Blood 115, 3520-3530 (2010).

Handke N, et al. Elaboration of glycopolymer-functionalized micelles from an N-vinylpyrrolidone/lactide-based reactive copolymer platform. Macromolecular bioscience 13, 1213-1220 (2013).

Broz M L, et al. Dissecting the tumor myeloid compartment reveals rare activating antigen-presenting cells critical for T cell immunity. Cancer Cell, 26, 638-652 (2014).

Matyjaszewski, K. et al., Atom Transfer Radical Polymerization; Chem. Rev. 2001, 101, 2921-2990.

Tsarenskt, N. et al, "Green" Atom Transfer Radical Polymerization: From Process Design to Preparation of Well-Defined Environmentally Friendly Polymeric Materials; Chem Rev 2007, 107, 2270-2299.

Braunecker, Wade et al., Controlled/Living Radical Polymerization: Features, Development, and Perspectives; Prog. Polym. Sci., 2007, 32, 93-146.

Chen, Y., et al. Targeted delivery of curcumin to tumors via PEG-derivatized FTS-based micellar system. The AAPS journal 16, 600-608 (2014).

Zhang, X., et al. PEG-farnesyl thiosalicylic acid telodendrimer micelles as an improved formulation for targeted delivery of paclitaxel. Molecular pharmaceutics 11, 2807-2814 (2014).

Zhang, X., et al. Reduction-sensitive dual functional nanomicelles for improved delivery of paclitaxel. Bioconjugate chemistry 25, 1689-1696 (2014).

Zhang, P., et al. A PEG-Fmoc conjugate as a nanocarrier for paclitaxel. Biomaterials 35, 7146-7156 (2014).

Zhang, X., et al. Targeted delivery of anticancer agents via a dual function nanocarrier with an interfacial drug-interactive motif. Biomacromolecules 15, 4326-4335 (2014).

Zhang, X., et al. Tunable pH-Responsive Polymeric Micelle for Cancer Treatment. ACS Macro Letters 4, 620-623 (2015).

Sun, J., et al. A prodrug micellar carrier assembled from polymers with pendant farnesyl thiosalicylic acid moieties for improved delivery of paclitaxel. Acta Biomaterialia 43, 282-291 (2016).

Wolfson, E., et al. Enhancing FTS (Salirasib) efficiency via combinatorial treatment. Biology of the cell 107, 130-143 (2015).

Zhang, X., et al. PEG-farnesylthiosalicylate conjugate as a nanomicellar carrier for delivery of paclitaxel. Bioconjugate Chem. 24, 464-472 (2013).

Zhang, P., et al. Design and evaluation of a PEGylated lipopeptide equipped with drug-interactive motifs as an improved drug carrier. AAPS J. 16, 114-124 (2014).

Marciano, D. et al., Farnesyl derivatives of rigid carboxylic acids-inhibitors of ras-dependent cell growth. J. Med. Chem. 38, 1267-72 (1995).

Xiong, X. B.et al., Enhanced intracellular delivery and improved antitumor efficacy of doxorubicin by sterically stabilized liposomes modified with a synthetic RGD mimetic. J. Control. Release, 107, 262-75 (2005).

Lu, J. et al. PEG-derivatized embelin as a nanomicellar carrier for delivery of paclitaxel to breast and prostate cancers. Biomaterials, 34, 1591-600 (2013).

Xiao, K. et al. A self-assembling nanoparticle for paclitaxel delivery in ovarian cancer, Biomaterials, 2009. vol. 30, pp. 6006-6016.

Gao, X. et al. Nanoassembly of surfactants with interfacial drug-interactive motifs as tailor-designed drug carriers, Molecular Pharmaceutics, Dec. 17, 2012 (E-pub) vol. 10, pp. 187-198.

A.B. Kunnumakkara, P. Anand, B.B. Aggarwal, Curcumin inhibits proliferation, invasion, angiogenesis and metastasis of different cancers through interaction with multiple cell signaling proteins, Cancer letters, 269 (2008) 199-225.

L.R. Chaudhary, K.A. Hruska, Inhibition of cell survival signal protein kinase B/Akt by curcumin in human prostate cancer cells, J Cell Biochem, 89 (2003) 1-5.

S. Lev-Ari, L. Strier, D. Kazanov, L. Madar-Shapiro, H. Dvory-Sobol, I. Pinchuk, B. Marian, D. Lichtenberg, N. Arber, Celecoxib and curcumin synergistically inhibit the growth of colorectal cancer cells, Clinical cancer research : an official journal of the American Association for Cancer Research, 11 (2005) 6738-6744.

M. Notarbartolo, P. Poma, L. Dusonchet, M. Cervello, N. D'Alessandro, Antitumor effects of curcumin, alone or in combination with cisplatin or doxorubicin, on human hepatic cancer cells. Analysis of their possible relationship to changes in NF-κB activation levels and in IAP gene expression, Cancer letters, 224 (2005) 53-65.

B. Rotblat, M. Ehrlich, R. Haklai, Y. Kloog, The Ras inhibitor farnesylthiosalicylic acid (Salirasib) disrupts the spatiotemporal localization of active Ras: A potential treatment for cancer, Method Enzymol, 439 (2008) 467-489.

M. Marom, R. Haklai, G. Benbaruch, D. Marciano, Y. Egozi, Y. Kloog, Selective-Inhibition of Ras-Dependent Cell-Growth by Farnesylthiosalicylic Acid, Journal of Biological Chemistry, 270 (1995) 22263-22270.

Y. Kloog, A.D. Cox, RAS inhibitors: potential for cancer therapeutics, Molecular medicine today, 6 (2000) 398-402.

(56) References Cited

OTHER PUBLICATIONS

R. Blum, Y. Kloog, Tailoring Ras-pathway-inhibitor combinations for cancer therapy, Drug resistance updates : reviews and commentaries in antimicrobial and anticancer chemotherapy, 8 (2005) 369-380.
J. Min, A. Zaslavsky, G. Fedele, S.K. McLaughlin, E.E. Reczek, T. De Raedt, I. Guney, D.E. Strochlic, L.E. MacConaill, R. Beroukhim, R.T. Bronson, S. Ryeom, W.C. Hahn, M. Loda, K. Cichowski, An oncogene-tumor suppressor cascade drives metastatic prostate cancer by coordinately activating Ras and nuclear factor-kappaB, Nature medicine, 16 (2010) 286-294.
M. Gana-Weisz, J. Halaschek-Wiener, B. Jansen, G. Elad, R. Haklai, Y. Kloog, The Ras inhibitor S-trans, trans-farnesylthiosalicylic acid chemosensitizes human tumor cells without causing resistance, Clinical Cancer Research, 8 (2002) 555-565.
Y. Kloog, A.D. Cox, M. Sinensky, Concepts in Ras-directed therapy, Expert opinion on investigational drugs, 8 (1999) 2121-2140.
R. Haklai, G. Elad-Sfadia, Y. Egozi, Y. Kloog, Orally administered FTS (salirasib) inhibits human pancreatic tumor growth in nude mice, Cancer chemotherapy and pharmacology, 61 (2008) 89-96.
A. Biran, M. Brownstein, R. Haklai, Y. Kloog, Down regulation of survivin and aurora A by histone deacetylase and RAS inhibitors: a new drug combination for cancer therapy, International journal of cancer. Journal international du cancer, 128 (2011) 691-701.
Mologni, S. Brussolo, M. Ceccon, C. Gambacorti-Passerini, Synergistic effects of combined Wnt/KRAS inhibition in colorectal cancer cells, PloS one, 7 (2012) e51449.
P. Anand, A.B. Kunnumakkara, R.A. Newman, B.B. Aggarwal, Bioavailability of curcumin: problems and promises, Molecular pharmaceutics, 4 (2007) 807-818.
A. Kraitzer, Y. Kloog, R. Haklai, M. Zilberman, Composite fiber structures with antiproliferative agents exhibit advantageous drug delivery and cell growth inhibition in vitro, Journal of pharmaceutical sciences, 100 (2011) 133-149.
Y.X. Huang, J.Q. Lu, X. Gao, J. Li, W.C. Zhao, M. Sun, D.B. Stolz, R. Venkataramanan, L.C. Rohan, S. Li, PEG-Derivatized Embelin as a Dual Functional Carrier for the Delivery of Paclitaxel, Bioconjugate Chem, 23 (2012) 1443-1451.
X. Gao, L. Huang, Potentiation of cationic liposome-mediated gene delivery by polycations, Biochemistry, 35 (1996) 1027-1036.
C. Ramachandran, H.B. Fonseca, P. Jhabvala, E.A. Escalon, S.J. Melnick, Curcumin inhibits telomerase activity through human telomerase reverse transcritpase in MCF-7 breast cancer cell line, Cancer letters, 184 (2002) 1-6.
R.A. McPherson, M.C. Conaway, C.W. Gregory, W. Yue, R.J. Santen, The novel ras antagonist, farnesylthiosalicylate, suppresses growth of prostate cancer in vitro, Prostate, 58 (2004) 325-334.
P. Starkel, N. Charette, I. Borbath, T. Schneider-Merck, C. De Saeger, J. Abarca, I. Leclercq, Y. Horsmans, Ras inhibition in hepatocarcinoma by S-trans-trans-farnesylthiosalicyclic acid: association of its tumor preventive effect with cell proliferation, cell cycle events, and angiogenesis, Molecular carcinogenesis, 51 (2012) 816-825.
K.S. Smalley, T.G. Eisen, Farnesyl thiosalicylic acid inhibits the growth of melanoma cells through a combination of cytostatic and pro-apoptotic effects, International journal of cancer. Journal international du cancer, 98 (2002) 514-522.
H. Aoki, Y. Takada, S. Kondo, R. Sawaya, B.B. Aggarwal, Y. Kondo, Evidence that curcumin suppresses the growth of malignant gliomas in vitro and in vivo through induction of autophagy: role of Akt and extracellular signal-regulated kinase signaling pathways, Molecular pharmacology, 72 (2007) 29-39.
L. Li, F.S. Braiteh, R. Kurzrock, Liposome-encapsulated curcumin: in vitro and in vivo effects on proliferation, apoptosis, signaling, and angiogenesis, Cancer, 104 (2005) 1322-1331.
M.M. Yallapu, M. Jaggi, S.C. Chauhan, Curcumin nanoformulations: a future nanomedicine for cancer, Drug discovery today, 17 (2012) 71-80.

Liu, L. Sun, Q.J. Wu, W.H. Guo, L. Li, Y.S. Chen, Y.C. Li, C.Y. Gong, Z.Y. Qian, Y.Q. Wei, Curcumin loaded polymeric micelles inhibit breast tumor growth and spontaneous pulmonary metastasis, Int J Pharmaceut, 443 (2013) 175-182.
H. Maeda, J. Wu, T. Sawa, Y. Matsumura, K. Hori, Tumor vascular permeability and the EPR effect in macromolecular therapeutics: a review, J Control Release, 65 (2000) 271-284.
H. Cabral, Y. Matsumoto, K. Mizuno, Q. Chen, M. Murakami, M. Kimura, Y. Terada, M.R. Kano, K. Miyazono, M. Uesaka, N. Nishiyama, K. Kataoka, Accumulation of sub-100 nm polymeric micelles in poorly permeable tumours depends on size, Nat Nanotechnol, 6 (2011) 815-823.
Qiu, J.; et al., Controlled/living radical polymerization in aqueous media: homogeneous and heterogeneous systems, Prog. Polym. Sci. 2001, 26, 2083-2134.
Lukyanov, Anatoly N., et al. Micelles from Lipid Derivatives of Water-Soluble Polymers as Delivery Systems for Poorly Soluble Drugs, Advanced Drug Delivery Reviews, vol. 56, 1273-1289, 2004.
Matyjaszewski, K., Ed. Controlled Radical Polymerization; ACS: Washington, D. C., 1998; ACS Symposium Series 685.
Matyjaszewski, K., Ed.; Controlled/Living Radical Polymerization. Progress in ATRP, NMP, and RAFT; ACS: Washington, D. C., 2000; ACS Symposium Series 768.
Tian, Lu et al., Core Crosslinkable Polymeric Micelles from PEG-Lipid Amphiphiles as Drug Carriers, J. Matter. Chem., 2004, 14, 2317-2324.
Dong, A et al. Chemical Insights into Antibacterial N-Halamines. Chemical Reviews. vol. 117, Mar. 2, 2017, pp. 4806-4862.
Nakabayashi, K et al. Recent progress in controlled radical polymerization of N-vinyl Monomers. European Polymer Journal, vol. 49, Jul. 24, 2013, pp. 2808-2838.
Matsuo, Y et al. Precise Synthesis of Block Polymers Composed of Three or More Blocks by Specially Designed Linking Methodologies in Conjunction with Living Anionic Polymerization System. Polymers, vol. 5, Jul. 17, 2013, pp. 1012-1040.
Lu. J. eL al., PEG_derivatized embelin as a nanomicellar carrier for delivery of paclitaxel to breast and prostate cancers, Biomaterials, Nov. 23, 2012 (E-pub), vol. 34, 1591-1600.
Xiao, K. et al., A self-assembling nanoparticle for paclitaxel delivery in ovarian cancer, Biomaterials, 2009, vol. 30, 6006-6016.
Gao, X. et al., Nanoassembly of surfactants with interfacial drug-interactive motifs as tailor-designed drug carriers, Molecular Pharmaceutics, Dec. 17, 2012 (E-pub), vol. 10, 187-198.
Bhadra D. et al., Pegylated Lysine Based Copolymeric Dendritic Micelles for Solubilization Ans Delivery Of Artemether, Journal of Pharmacy and Pharmaceutical Sciences, Canadian Society for Pharmaceutical Sciences, Edmonton, CA, vol. 8. No. 3, Sep. 2, 2005, pp. 467-482.
Sang Cheon Lee et al, Hydrotropic Polymeric Micelles for Enhanced Paclitaxel Solubility: In Vitro and In Vivo Characterization, Biomacromolecules, vol. 8. No. 1, Dec. 1, 2006, pp. 202-208.
Saravanakumar G et al., Hydrotropic hyaluronic acid conjugates: Synthesis, characterization and implications as a carrier of paclitaxel, International Journal of Pharmaceutics, Elsevier BV, NL, vol. 394. No. 1-2, Jul. 15, 2010, pp. 154-161.
Saravanakumar G et al., Hydrotropic oligomer-conjugated glycol chitosan as a carrier of paclitaxel: Synthesis characterization and in vivo biodistribution, Journal of Controlled Release, Elsevier, Amsterdam, NL, vol. 140, No. 3, Dec. 16, 2009, pp. 210-217.
Ian W. Hamley et al., A Thermoresponsive Hydrogel Based on Telechelic PEG End-Capped with Hydrophobic Dipeptides, Macromolecular Bioscience, vol. 11, No. 8, May 6, 2011, pp. 1068-1078.
Peng Zhang et al., Design and Evaluation of a PEGylated Lipopeptide Equipped with Drug-Interactive Motifs as an Improved Drug Carrier, The AAPS Journal, vol. 16, No. 1, Nov. 27, 2013, pp. 114-124.
Schakov Rafael et al., Peptide-based hydrogel nanoparticles as effective drug delivery agents, Bioorganic & Medicinal Chemistry, Pergamon, GB, vol. 21, No. 12, Mar. 21, 2013, pp. 3517-3522.
Xiaolan Zhang et al., PEG-Farnesylthiosalicylate Conjugate as a Nanomicellar Carrier for Delivery of Paclitaxel, Bioconjugate Chemistry, vol. 24, No. 3. Mar. 20, 2013, pp. 464-472.

(56) References Cited

OTHER PUBLICATIONS

Jianqin Lu et al., Design and Characterization of PEG-Derivatized Vitamin E as a Nanomicellar Formulation for Delivery of Paclitaxel, Molecular Pharmaceutics, vol. 10, No. 8, Aug. 5, 2013, pp. 2888-2898.
Beg, Sarwar, Bioavailability Enhancement Strategies: Basics, Formulation Approaches and Regulatory Considerations, Current Drug Delivery, 2011, vol. 8, No. 6, pp. 1-12.
Nanjwade, Basavaraj K., Functions of Lipids for Enhancement of Oral Bioavailability of Poorly Water-Soluble Drugs, Sci Pharm. 2011; 79: 705-727.
Buse, Joshua, Properties, engineering and applications of lipid-based nanoparticle drug-delivery systems: current research and advances,Nanomedicine (2010) 5(8), 1237-1260.
Puri, Anu et al., Lipid-Based Nanoparticles as Pharmaceutical Drug Carriers: From Concepts to Clinic, Crit Rev Ther Drug Carrier Syst. 2009 ; 26(6): 523-580.
Narang, Ajit S. et al., Stable drug encapsulation in micelles and microemulsions, International Journal of Pharmaceutics 345 (2007) 9-25.
Jiang, Jianfei et al., A Mitochondria-Targered Nitroxide/Hemigramicisin S Conjugate Protects Mouse Embryonic Cells Against Gamma Irradiation, Int J Radiat Oncol Biol Phys. Mar. 1, 2008; 70(3): 816-825.
Jiang, Jianfei et al., Structural Requirements for Optimized Delivery, Inhibition of Oxidative Stress, and Antiapoptotic Activity of Targeted Nitroxides, The Journal of Pharmacology and Experimental Therapeutics, vol. 320, No. 3, 1050-1060, 2007.
Rajagopalan, Malolan S., et al., The Mitochondria-targeted Nitroxide JP4-039 Augments Potentially Lethal Irradiation Damage Repair, in vivo 23: 717-726 (2009).
Epperly, Michael W., et al., Intraesophageal Administration of GS-Nitroxide (JP4-039) Protects Against Ionizing Irradiation-induced Esophagitis, in vivo 24: 811-820 (2010).
Epperly, M., et al., Topical Application of GS-Nitroxide JP4-039 Emulsion Mitigates Ionizing Irradiation Induced Skin Burns, Int. J. Radiation Oncology Biol. Physics. 78(2010)S634-S635.
Goff, Julie P., et al., Radiobiologic Effects of GS-Nitroxide (JP4-039) on the Hematopoietic Syndrome, in vivo 25: 315-324 (2011).
Frantz, Celine-Marie, et al., Large-Scale Asymmetric Synthesis of the Bioprotective Agent JP4-039 and Analogs, Organic Letters (2011), Vo. 13, No. 9, 2318-2321.
Zalipsky, S., et al., Attachment of Drugs to polyethylene Glycols, Eur. Polvm. J. vol. 19, No. 12, pp. 1177 1183, 1983.
Patist, A. et al., On the Measurement of Critical Micelle Concentrations of Pure and Technical-Grade Nonionic Surfactants, Journal of Surfactants and Detergents, vol. 3, No. 1 (Jan. 2000), 53-58.
Kenworthy, A. K. et al., Range and Magnitude of the Steric Pressure Between Bilayers Containing Phospholipids with Covalently Attached Poly(ethylene glycol), Biophysical Journal vol. 68 May 1995 1921-1936.
Zhu, Peizhi et al., Fluorescence Quenching by Tempo: A Sub-30 A° Single-Molecule Ruler, Biophys. J. 89(2005) L37-L39.
Lee, Jaehwi, et al., Hydrotropic Solubilization of Paclitaxel: Analysis of Chemical Structures for Hydrotropic Property, Pharmaceutical Research, vol. 20, No. 7, Jul. 2003, 1022-1030.
Kim, Ji Young, et al., Hydrotropic polymer micelles as versatile vehicles for delivery of poorly water-soluble drugs, Journal of Controlled Release 152 (2011) 13-20.
Dabholkar, Rupa D., et al., Polyethylene glycol-phosphatidylethanolamine conjugate (PEG-PE)-based mixed micelles: Some properties, loading with paclitaxel, and modulation of P-glycoprotein-mediated efflux, International Journal of Pharmaceutics 315 (2006) 148-157.
Luo, Juntao et al., Well-Defined, Size-Tunable, Multifunctional Micelles for Efficient Paclitaxel Delivery for Cancer Treatment, Bioconjugate Chem. 2010, 21, 1216-1224.
Yen, Chiao-Ting, et al., Design and synthesis of new N-(fluorenyl-9-methoxycarbonyl) (Fmoc)-dipeptides as anti-inflammatory agents, European Journal of Medicinal Chemistry 44 (2009) 1933-1940.

Zhang, Yan, et al., Supramolecular Hydrogels Respond to Ligand-Receptor Interaction, J. Am. Chem. Soc. 2003, 125, 13680-13681.
Jayawarna, Vineetha et al., Nanostructured Hydrogels for Three-Dimensional Cell Culture Through Self-Assembly of Fluorenylmethoxycarbonyl-Dipeptides, Adv. Mater. 2006, 18, 611-614.
Mahler, Assaf et al., Rigid, Self-Assembled Hydrogel Composed of a Modified Aromatic Dipeptide, Adv. Mater. 2006, 18, 1365-1370.
Huang, Yixian, et al., PEG-Derivatized Embelin as a Dual Functional Carrier for the Delivery of Paclitaxel Bioconjugate Chem. 2012, 23, 1443-1451.
Dong, He et al., Long-Circulationg 15nm Micelles Based on Amphiphilic 3-Helix Peptide-PEG Conjugates, ACSNANO, vol. 6, No. 6, 5320-5329, 2012.
L. Rahib et al., Projecting cancer incidence and deaths to 2030: the unexpected burden of thyroid, liver, and pancreas cancers in the United States, Cancer Res. 74 (2014) 2913-2921.
H. Burris 3rd et al., Improvements in survival and clinical benefit with gemcitabine as first-line therapy for patients with advanced pancreas cancer: a randomized trial, J. Clin. Oncol. 15 (1997) 2403-2413.
L.A. Shipley et al., Metabolism and disposition of gemcitabine, and oncolytic deoxycytidine analog, in mice, rats, and dogs, Drug Metab. Dispos. 20 (1992) 849-855.
K.K. Frese et al., nab-Paclitaxel potentiates gemcitabine activity by reducing cytidine deaminase levels in a mouse model of pancreatic cancer, Cancer discovery 2 (2012) 260-269.
N. Awasthi et al., Comparative benefits of Nab-paclitaxel over gemcitabine or polysorbatebased docetaxel in experimental pancreatic cancer, Carcinogenesis 34 (2013) 2361-2369.
H. Meng et al., Use of a lipid-coated mesoporous silica nanoparticle platform for synergistic gemcitabine and paclitaxel delivery to human pancreatic cancer in mice, ACS Nano 9 (2015) 3540-3557.
L. Zitvogel et al., Immunological aspects of cancer chemotherapy, Nat. Rev. Immunol. 8 (2008) 59-73.
L. Apetoh et al., Toll-like receptor 4-dependent contribution of the immune system to anticancer chemotherapy andradiotherapy, Nat. Med. 13 (2007) 1050.
M.S. Sasso et al., Low dose gemcitabine-loaded lipid nanocapsules target monocytic myeloid-derived suppressor cells and potentiate cancer immunotherapy, Biomaterials 96 (2016) 47-62.
K. Thind et al., Immunotherapy in pancreatic cancer treatment: a new frontier, Therapeutic advances in gastroenterology 10 (2017) 168-194.
N. Martinez-Bosch et al., Immune Evasion in Pancreatic Cancer: from Mechanisms to Therapy, Cancers 10 (2018) 6.
C. Uyttenhove et al., Evidence for a tumoral immune resistance mechanism based on tryptophan degradation by indoleamine 2, 3-dioxygenase, Nat. Med. 9 (2003) 1269.
J. Godin-Ethier et al., Indoleamine 2, 3-dioxygenase expression in human cancers: clinical and immunologic perspectives, Clin. Cancer Res. 17 (2011) 6985-6991.
H.K. Koblish et al., Hydroxyamidine inhibitors of indoleamine-2, 3-dioxygenase potently suppress systemic tryptophan catabolism and the growth of IDO-expressing tumors, Mol. Cancer Ther. 9 (2010) 489-498.
N.Liu et al., Selective inhibition of IDO1 effectively regulates mediators of antitumor immunity, Blood 115 (2010) 3520-3530.
A. Witkiewicz et al., Expression of indoleamine 2, 3-dioxygenase in metastatic pancreatic ductal adenocarcinoma recruits regulatory T cells to avoid immune detection, J. Am. Coll. Surg. 206 (2008) 849-854.
D.H. Munn et al., Indoleamine 2, 3-dioxygenase and tumor-induced tolerance, The Journal of clinical investigation 117 (2007) 1147-1154.
D.H. Munn et al., IDO in the tumor microenvironment: inflammation, counterregulation, and tolerance, Trends Immunol. 37 (2016) 193-207.
A. Nayak et al., A Phase I study of NLG919 for adult patients with recurrent advanced solid tumors, Journal for immunotherapy of cancer 2 (2014) P250.

(56) References Cited

OTHER PUBLICATIONS

Y. Chen et al., An immunostimulatory dual-functional nanocarrier that improves cancer immunochemotherapy, Nat. Commun. 7 (2016) 13443-13455.
H. Maeda et al., The EPR effect for macromolecular drug delivery to solid tumors: Improvement of tumor uptake, lowering of systemic toxicity, and distinct tumor imaging in vivo, Adv. Drug Delivery. Rev. 65 (2013) 71-79.
M.K.Danquah et al., Extravasation of polymeric nanomedicines across tumor vasculature, Adv. Drug Delivery. Rev. 63 (2011) 623-639.
F. Danhier et al., To exploit the tumor microenvironment: passive and active tumor targeting of nanocarriers for anti-cancer drug delivery, J. Control. Release 148 (2010) 135-146.
V.P. Chauhan et al., Strategies for advancing cancer nanomedicine, Nat. Mater. 12 (2013) 958-962.
H. Cabral et al., Accumulation of sub-100 nm polymeric micelles in poorly permeable tumours depends on size, Nat. Nanotechnol. 6 (2011) 815-823.
V.P. Chauhan et al., Normalization of tumour blood vessels improves the delivery of nanomedicines In a size-dependent manner, Nat. Nanotechnol. 7 (2012) 383-388.
K. Huang et al., Size-dependent localization and penetration of ultrasmall gold nanoparticles in cancer cells, multicellular spheroids, and tumors in vivo, ACS Nano 6 (2012) 4483-4493.
Z. Popovic et al., A nanoparticle size series for in vivo fluorescence imaging, Angew. Chem. 122 (2010) 8831-8834.
V.P. Chauhan et al., Fluorescent nanorods and nanospheres for real-time in vivo probing of nanoparticle shapedependent tumor penetration, Angewandte Chemie International Edition 50 (2011) 11417-11420.
J. Sun et al., A prodrug micellar carrier assembled from polymers with pendant farnesyl thiosalicylic acid moieties for improved delivery of paclitaxel, Acta Biomater. 43 (2016) 282-291.
R. Bruni et al., Ultrasmall polymeric nanocarriers for drug delivery to podocytes in kidney glomerulus, J. Control. Release 255 (2017) 94-107.
M. Vandana et al., Long circulation and cytotoxicity of PEGylated gemcitabine and its potential for the treatment of pancreatic cancer, Biomaterials 31 (2010) 9340-0356.
D. Chitkara et al., Self-assembling, amphiphilic polymer-gemcitabine conjugate shows enhanced antitumor efficacy against human pancreatic adenocarcinoma, Bioconjug. Chem. 24 (2013) 1161-1173.
J. Sun et al., Doxorubicin delivered by a redox-responsive dasatinib-containing polymeric prodrug carrier for combination therapy, J. Control. Release 258 (2017) 43-55.
M. Zauri et al., CDA directs metabolism of epigenetic nucleosides revealing a therapeutic window in cancer, Nature 524 (2015) 114-118.
N. Weizman et al., Macrophages mediate gemcitabine resistance of pancreatic adenocarcinoma by upregulating cytidine deaminase, Oncogene 33 (2014) 3812-3819.
T. Kammertoens et al., Tumour ischaemia by interferon-γ resembles physiological blood vessel regression, Nature 545 (2017) 98.
P.R. Kunk et al., From bench to bedside a comprehensive review of pancreatic cancer immunotherapy, Journal for immunotherapy of cancer 4 (2016) 14.
Y. Zhao et al., Can nanomedicines kill cancer stem cells?, Adv. Drug Delivery. Rev. 65 (2013) 1763-1783.
J. Sun et al., Programmable co-delivery of the immune checkpoint inhibitor NLG919 and chemotherapeutic doxorubicin via a redox-responsive immunostimulatory polymeric prodrug carrier, Acta Pharmacol. Sin. 38 (2017) 823-834.
G.M. Soliman et al., Dendrimers and miktoarm polymers based multivalent nanocarriers for efficient and targeted drug delivery, Chem. Commun. 47 (2011) 9572-9587.
Y. Jiang et al., The interplay of size and surface functionality on the cellular uptake of sub-10 nm gold nanoparticles, ACS Nano 9 (2015) 9988-9993.
J. Wang et al., The role of micelle size in tumor accumulation, penetration, and treatment, ACS Nano 9 (2015) 7195-7206.
R. Nagarajan et al., Block copolymer self?assembly in selective solvents: Spherical micelles with segregated cores, The Journal of Chemical Physics 90 (1989) 5843-5856.
K. Mortensen et al., Poly (ethylene oxide)-poly (propylene oxide)-poly (ethylene oxide) triblock copolymers in aqueous solution. The influence of relative block size, Macromolecules 26 (1993) 4128-4135.
Y.H. Bae et al., Stability issues of polymeric micelles, J. Control. Release 131 (2008) 2-4.
H. Chen et al., Fast release of lipophilic agents from circulating PEG-PDLLA micelles revealed by in vivo forster resonance energy transfer imaging, Langmuir 24 (2008) 5213-5217.
A. Schulz et al., Drug-induced morphology switch in drug delivery systems based on poly (2-oxazoline) s, ACS Nano 8 (2014) 2686-2696.
A. Reisch et al., Charge-controlled nanoprecipitation as a modular approach to ultrasmall polymer nanocarriers: making bright and stable nanoparticles, ACS Nano 9 (2015) 5104-5116.
Y. Wang et al., Dissipative particle dynamics simulation study on the mechanisms of self-assembly of large multimolecular micelles from amphiphilic dendritic multiarm copolymers, Soft Matter 9 (2013) 3293-3304.

\* cited by examiner

Linker L¹ examples:

Linker L² and P examples:
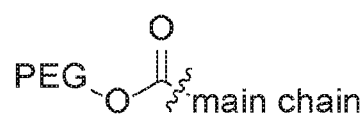
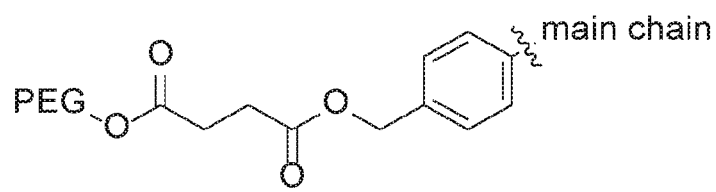
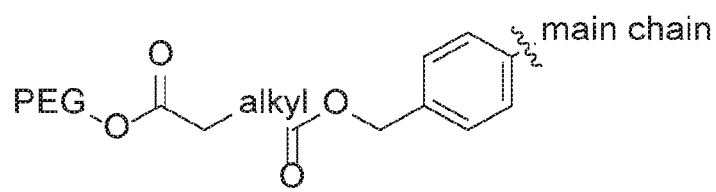
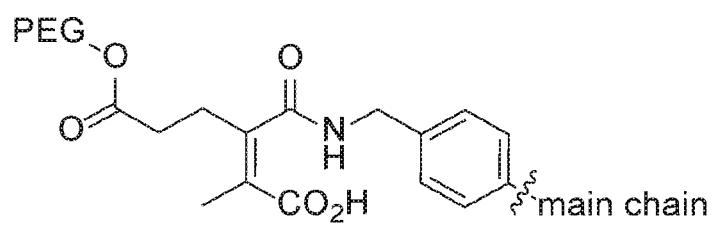
Fig. 3D

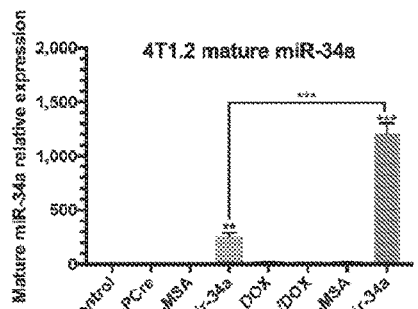
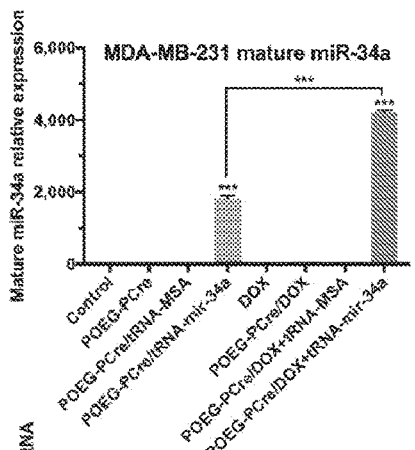
Fig. 13A
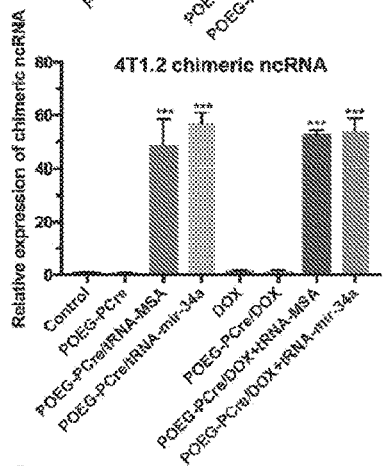
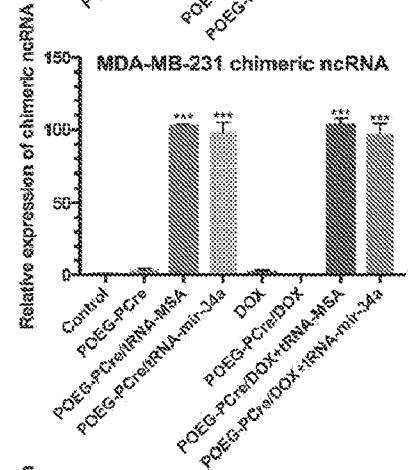
Fig. 13B
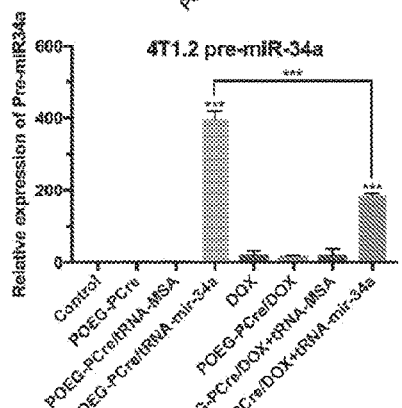
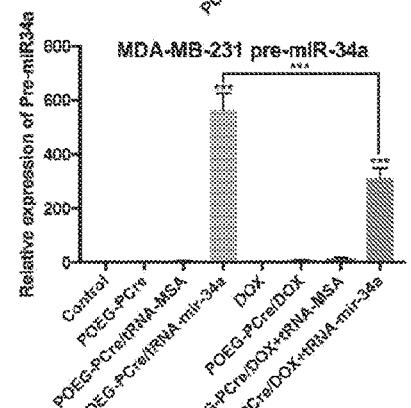
Fig. 13C
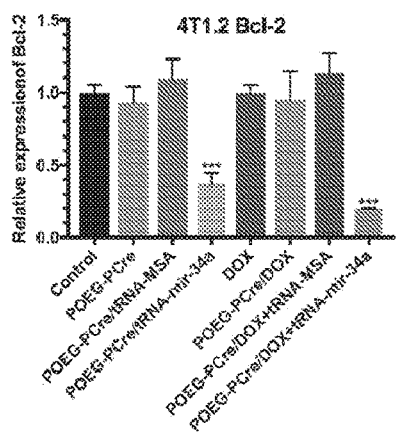
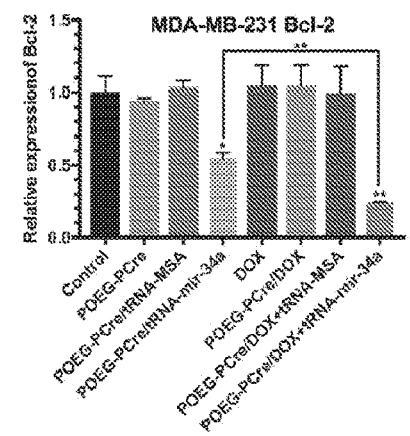
Fig. 13D

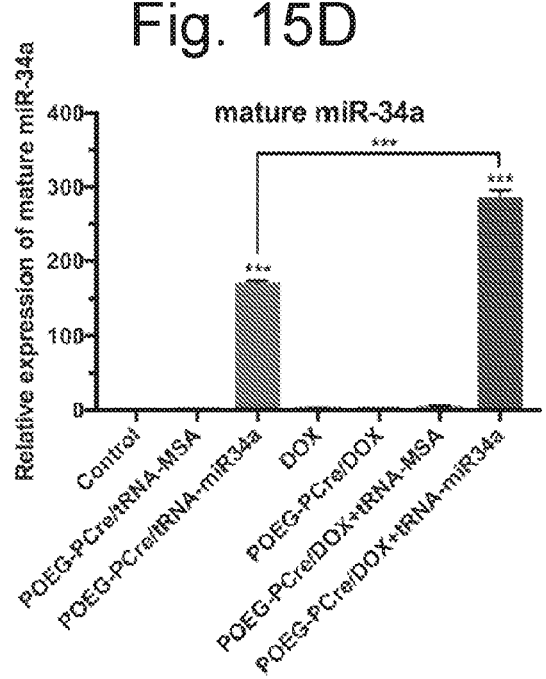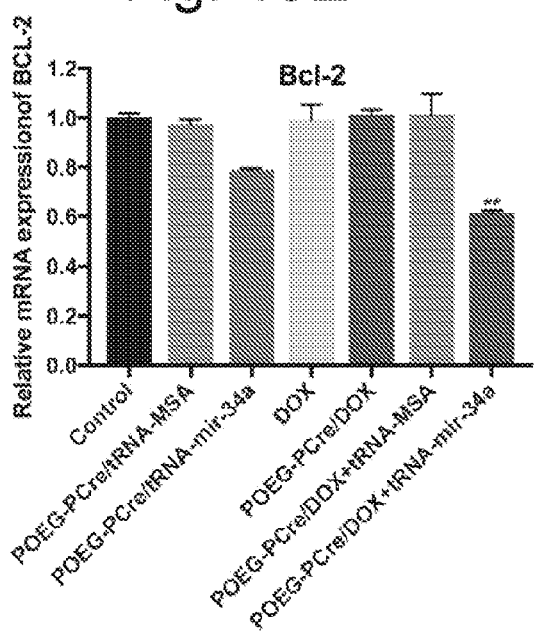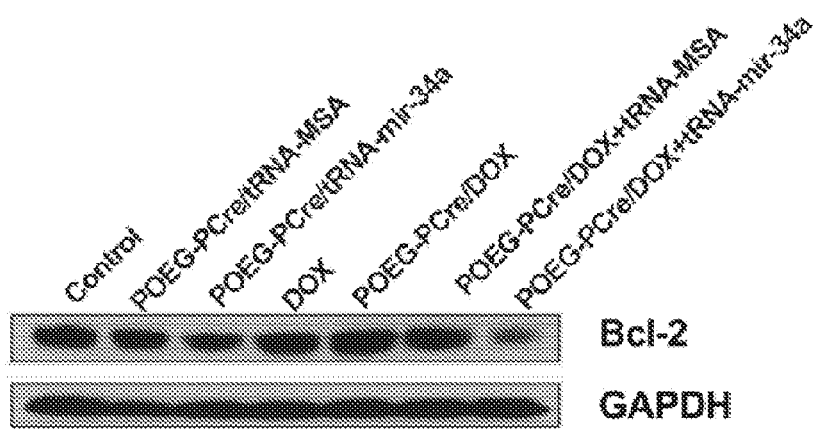

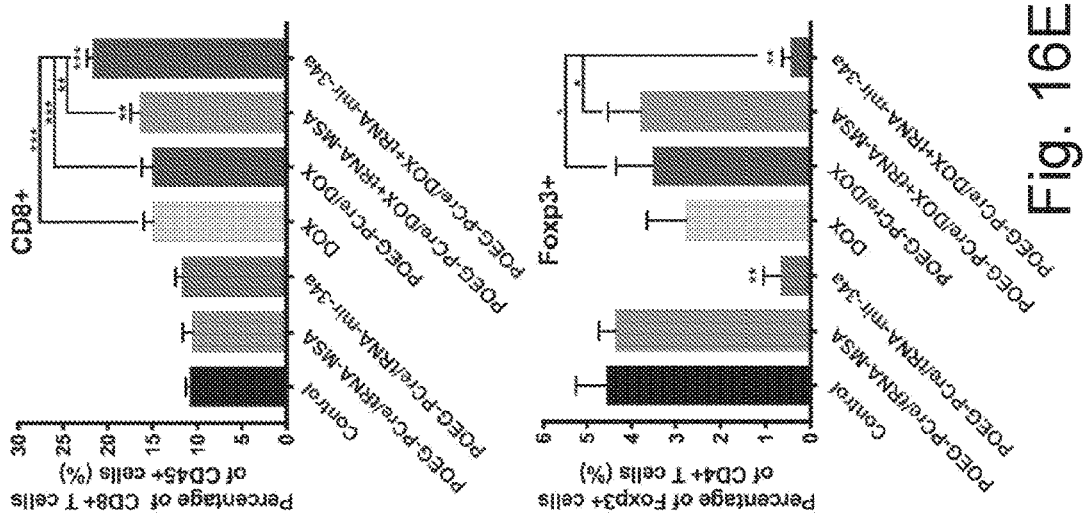
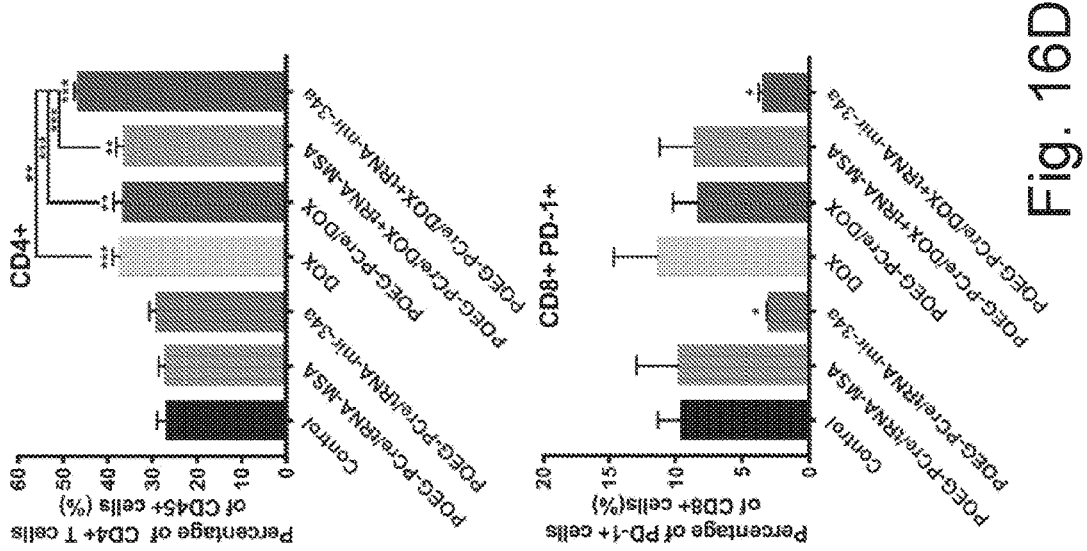

CATIONIC AMPHIPHILIC POLYMERS FOR CODELIVERY OF HYDROPHOBIC AGENTS AND NUCLEIC ACIDS

CROSS-REFERENCE TO RELATED APPLICATIONS

This application is a national phase filing of PCT International Patent Application No. PCT/US2019/028418, filed Apr. 20, 2019, which claims benefit of U.S. Provisional Patent Application Ser. No. 62/660,515, filed Apr. 20, 2018, the disclosures of which are incorporated herein by reference.

GOVERNMENTAL INTEREST

This invention was made with government support under grant numbers CA174305 and CA223788 awarded by the National Institutes of Health. The government has certain rights in the invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosures of all references cited herein are incorporated by reference.

Drug combination therapy has represented a promising strategy to minimize the administration dosage of each drug (or therapeutic compound) and achieve the synergistic therapeutic effect. However, there are many molecular targets that are deemed "undruggable" with respect to development of small molecule drugs.

A number of delivery systems have been developed for gene delivery, including viral carriers, peptides, liposomes and cationic polymers. Despite the high efficiency in gene delivery, viral vector-based therapies are limited by their safety concerns such as immunogenicity, and the difficulty of large-scale production. On the other hand, non-viral nanocarriers have attracted increasing attention in nucleic acid delivery because of their favorable safety profiles and the ease of production.

Alternative strategies include, for example, small interference RNA (siRNA)-based approach to modulate the functions of "undruggable" genes. A combination of small drugs and nucleic acid-based therapeutics (including, for example, DNA and siRNA) represents an attractive approach for treatment of many diseases. Indeed, increasing evidence shows that combination of therapeutic genes and drugs may synergistically induce the apoptosis of cancer cells. However, the simultaneous delivery of small molecule compounds, therapeutic agents or drugs and nucleic acid-based compounds into targeted cells has been a big challenge as a result of the differences in physicochemical properties of the two types of therapeutic agents. There is a continuing need to develop a delivery system capable of co-delivering, for example small molecule therapeutic agents or drugs (for example, chemotherapeutic agents or drugs) and nucleic acid-based therapeutic agents or drugs simultaneously and with high efficiency for cancer and/or other therapies.

SUMMARY

In one aspect, a formulation includes a plurality of polymers including a hydrophobic polymer backbone (for example, formed via radical polymerization), a first plurality of pendant groups attached to the hydrophobic polymer backbone and including at least one cationic group, and a second plurality of pendant groups attached to the hydrophobic polymer backbone and including at least one hydrophilic polymer, a first therapeutic compound, and a second therapeutic compound, wherein the second therapeutic compound is different from the first therapeutic compound and includes a nucleic acid. In a number of embodiments, the first therapeutic compound is a small molecule therapeutic compound. The first therapeutic compound may, for example, have a molecular weight below 2.0 kDa, below 1.5 kDa or below 1 kDa. In a number of embodiments, the second therapeutic compound includes RNA or DNA. For example, the second therapeutic compound may include a gene or siRNA. In a number of embodiments, the first therapeutic compound is a chemotherapeutic compound. The plurality of polymers may, for example, form micelles.

At least one of the first plurality of pendant groups or the second plurality of pendant groups may, for example, be attached to the hydrophobic polymer backbone via a linking moiety including a group interactive via π-π stacking. In a number of embodiments, the first plurality of pendant groups is attached to the hydrophobic polymeric backbone via a first linking group including at least a first group which is interactive via π-π stacking, and the second plurality of pendant groups is attached to the hydrophobic polymer backbone via a second linking group including at least a second group which is interactive via π-π stacking. The group which is interactive via π-π stacking may, for example, include or be an aromatic group. The at least one group interactive via π-π stacking may, for example, include an aromatic group (for example, a benzyl group or a naphthyl group). In a number of embodiments, the at least one group interactive via π-π stacking includes a benzyl group.

The hydrophobic polymer backbone may, for example, be formed via radical polymerization of vinyl monomers. In a number of embodiment, the hydrophobic polymer backbone is formed via a free radical polymerization or via a reversible-deactivation radical polymerization.

The at least one cationic group may, for example, include an inherently cationic group or a group which forms a cation in the formulations hereof and/or in vivo. A group which forms a cation in vivo may, for example, be an amine group, wherein the amine group is an acyclic amine group, a cyclic amine group or a heterocyclic amine group. In a number of embodiments, the amine group (for example, a primary amine, a secondary amine, or a tertiary amine) is selected from the group consisting of a metformin group, a morpholine group, a piperazine group, a pyridine group, a pyrrolidine group, piperidine, a thiomorpholine, a thiomorpholine oxide, a thiomorpholine dioxide, imidazole, guanidine or creatine. In a number of embodiments, the at least on cationic group includes a quaternary ammonium group.

In a number of embodiments, the second plurality of pendant groups is attached to the hydrophobic polymer backbone via a linking moiety that is labile in vivo or under in vivo conditions. For example, the linking moiety may be labile under acidic pH conditions.

In another aspect, a formulation for delivery of compounds in vivo includes a plurality of polymers including a hydrophobic polymer backbone (for example, formed via radical polymerization), a first plurality of pendant groups attached to the hydrophobic polymer backbone and including at least one cationic group, and a second plurality of pendant groups attached to the hydrophobic polymer backbone and including at least one hydrophilic polymer, and a plurality of nucleic acid compounds. The plurality of polymers may, for example, form micelles. The plurality of nucleic acid compounds interact with cationic groups of the first plurality of pendant groups. The formulations and/or components thereof may, for example, be further characterized as described above.

In another aspect, a method of formulating a composition for delivery of a first therapeutic compound and a second therapeutic compound to a patient, wherein the second therapeutic compound is different from the first therapeutic compound and includes a nucleic acid, includes mixing a plurality of polymers including a hydrophobic polymer backbone (for example, formed via radical polymerization), a first plurality of pendant groups attached to the hydrophobic polymer backbone and including at least one cationic group, and a second plurality of pendant groups attached to the hydrophobic polymer backbone and including at least one hydrophilic polymer with a plurality of the first therapeutic compounds and with a plurality of the second therapeutic compounds. The plurality of polymers may, for example, form micelles. The plurality of the second therapeutic compounds may, for example, interact with cationic groups of the first plurality of pendant groups. The formulations and/or components thereof may, for example, be further characterized as described above.

In a further aspect, a method of delivering a first therapeutic compound and a second therapeutic compound to a patient, wherein the second therapeutic compound is different from the first therapeutic compound and includes a nucleic acid, includes administering a formulation including a plurality of polymers including a hydrophobic polymer backbone (for example, formed via radical polymerization), a first plurality of pendant groups attached to the hydrophobic polymer backbone and including at least one cationic group, and a second plurality of pendant groups attached to the hydrophobic polymer backbone and including at least one hydrophilic polymer, a plurality of the first therapeutic compounds and a plurality of the second therapeutic compound. As described above, the plurality of polymers may, for example, form micelles. The plurality of the second therapeutic compounds may, for example, interact with cationic groups of the first plurality of pendant groups. The formulations and/or components thereof may, for example, be further characterized as described above.

In a further aspect, a polymer includes a hydrophobic polymer backbone, a first plurality of pendant groups attached to the hydrophobic polymer backbone and including at least one cationic group, and a second plurality of pendant groups attached to the hydrophobic polymer backbone and including at least one hydrophilic polymer.

In still a further aspect, a polymer includes a hydrophobic polymer backbone formed via radical polymerization, a first plurality of pendant groups attached to the hydrophobic polymer backbone and including at least one cationic group, and a second plurality of pendant groups attached to the hydrophobic polymer backbone and including at least one hydrophilic polymer.

In the polymers hereof, the at least one pendant group of the first plurality of pendant groups or at least one pendant group of the second plurality of pendant group may, for example, include both at least on cationic group and at least one hydrophilic polymer.

In a number of embodiments, at least one of the at least one of the first plurality of pendant groups or the second plurality of pendant groups is attached to the hydrophobic polymer backbone via a linking moiety including at least one group which is interactive via π-π stacking. In a number of embodiments, the first plurality of pendant groups is attached to the hydrophobic polymeric backbone via a first linking group including at least a first group which is interactive via π-π stacking, and the second plurality of pendant groups is attached to the hydrophobic polymer backbone via a second linking group including at least a second group which is interactive via π-π stacking. The at least one group interactive via π-π stacking may, for example, include an aromatic group (for example, a benzyl group or a naphthyl group). In a number of embodiments, the at least one group interactive via π-π stacking includes a benzyl group.

The hydrophobic polymer backbone may, for example, formed via radical polymerization of vinyl monomers. In a number of embodiments, the hydrophobic polymer backbone is formed via a free radical polymerization or via a reversible-deactivation radical polymerization.

The at least one cationic group may, for example, include an inherently cationic group of a group which forms a cation in the formulation hereof and/or in vivo. In a number of embodiments, the group which forms a cation in vivo is an amine group, wherein the amine group is an acyclic amine group, a cyclic amine group or a heterocyclic amine group. The amine may, for example, be selected from the group consisting of a metformin group, a morpholine group, a pyridine group, a piperazine group, a pyrrolidine group, piperidine, a thiomorpholine, a thiomorpholine oxide, a thiomorpholine dioxide, imidazole, guanidine or creatine. The cationic group may, for example, include a quaternary ammonium group.

The second plurality of pendant groups may, for example, be attached to the hydrophobic polymer backbone via a linking moiety that is labile in vivo or under in vivo conditions. The second plurality of pendant groups may, for example, be attached to the hydrophobic polymer backbone via a linking moiety that is labile under acidic pH conditions.

The present systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 3D illustrates representative examples of a second linking group ($L^2$) for the polymers hereof.

FIG. 13A illustrates a study of the processing of tRNA-mir-34a into mature tumor suppressor miR-34a in 4T1.2 cells and MDA-MB-231 cells as evaluated by quantitative RT-PCR for various formulations.

FIG. 13B illustrates a study of the amounts of chimeric ncRNA scaffold inside 4T1.2 cells and MDA-MB-231 cells after treatment with various formulations.

FIG. 13C illustrates a study of the level of pre-miR-34a in 4T1.2 cells and MDA-MB-231 cells after treatment with various formulations.

FIG. 13D illustrates a study of the mRNA expression levels in 4T1.2 cells and MDA-MB-231 cells for various formulations.

FIG. 15D illustrates a study of the relative expression of mature miR-34a after treatment with various formulations.

FIG. 15E illustrates a study relative mRNA expression of Bcl-2 after treatment with various formulations.

FIG. 15F illustrates that the expression levels of Bcl-2 in tumor tissues were significantly suppressed at both mRNA and protein levels following treatment with tRNA-mir-34a, particularly in a DOX co-loaded formulation.

FIG. 16A illustrates a study of $CD4^+$ cell numbers after treatment with various formulations.

FIG. 16B illustrates a study of $CD8^+$ cell numbers after treatment with various formulations.

FIG. 16C illustrates a study of the number of functional CD8 (IFN-γ+ CD8) cells after treatment with various formulations.

FIG. 16D illustrates a study of the numbers of PD1+ CD8 cells after treatment with various formulations.

FIG. 16E illustrates a study of the numbers of $Foxp3^+$ cells after treatment with various formulations.

FIG. 16F illustrates a study of the numbers of MDSC cells after treatment with various formulations.

DETAILED DESCRIPTION

Figure 1:
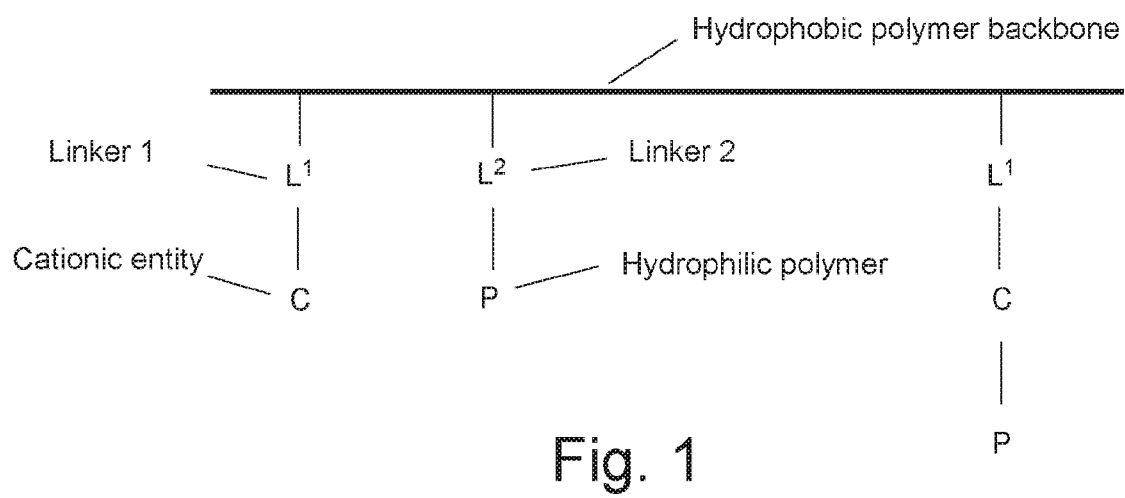
FIG. 1 illustrated schematically embodiments of amphiphilic polymers hereof.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a therapeutic compound" includes a plurality of such therapeutic compounds and equivalents thereof known to those skilled in the art, and so forth, and reference to "the therapeutic compound" is a reference to one or more such therapeutic compounds and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

As used herein, the term "polymer" refers to a chemical compound that is made of a plurality of small molecules or monomers that are arranged in a repeating structure to form a larger molecule. Polymers may occur naturally or be formed synthetically. The use of the term "polymer" encompasses homopolymers as well as copolymers. The term "copolymer" is used herein to include any polymer having two or more different monomers. Copolymers may, for example, include alternating copolymers, periodic copolymers, statistical copolymers, random copolymers, block copolymers, graft copolymers etc. Examples of polymers include, for example, polyalkylene oxides.

As used herein, the term "pendant" refers to a group or moiety attached to a backbone chain of a long molecule such as a polymer as described above. Pendant group may be either (1) short chain or low molecular weight groups or (2) long chain or high molecular groups such as polymers. Pendant groups are sometime referred to as side groups. Long chain pendant groups or high molecular weight pendant groups are sometimes referred to as "pendant chains" or "side chains".

Figure 2:
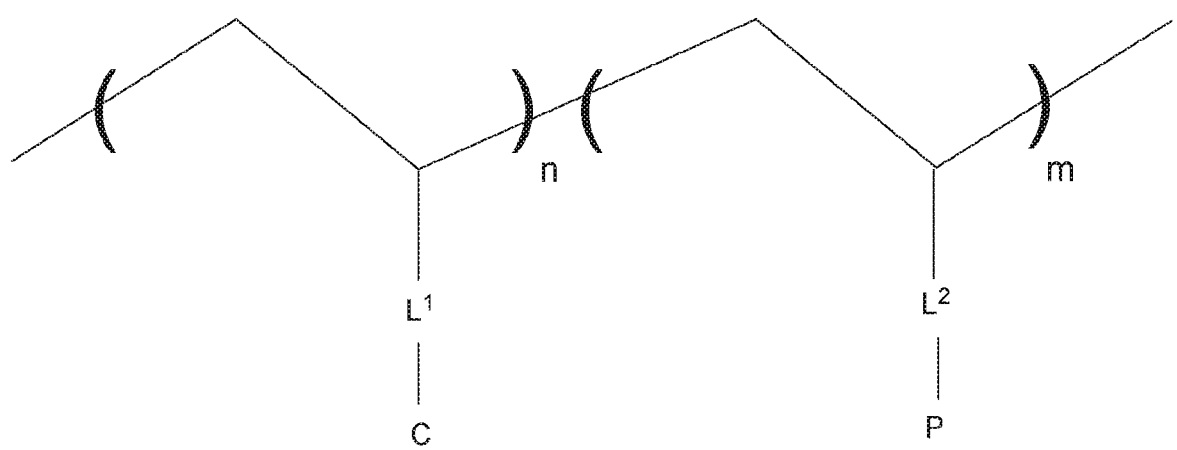
FIG. 2 illustrated schematically embodiments of amphiphilic polymers hereof.

In a number of embodiments, systems, formulations, methods and compositions hereof are provide for co-delivery of small molecule therapeutic agents or drugs (for example, chemotherapeutic therapeutic agents or drugs) and nucleic acid-based therapeutic agents or drugs simultaneously. FIGS. 1 and 2 illustrated schematically amphiphilic polymers hereof. The amphiphilic polymer may, for example, be formed via radical polymerization to have a hydrophobic polymer backbone. The hydrophobic polymer backbone may, for example, be formed via a free radical polymerization or via a reversible-deactivation radical polymerization or RDRP (formerly referred to a controlled radical polymerization or CRP).

Reversible-Deactivation Radical Polymerization (RDRP) procedures include, for example, Nitroxide Mediated Polymerization (NMP), Atom Transfer Radical Polymerization (ATRP), and Reversible Addition Fragmentation Transfer (RAFT) and others (including cobalt mediated transfer) that have evolved over the last two decades. RDRP provide access to polymer and copolymers comprising radically polymerizable/copolymerizable monomers with predefined molecular weights, compositions, architectures and narrow/controlled molecular weight distributions. Because RDRP processes can provide compositionally homogeneous well-defined polymers, with predicted molecular weight, narrow/designed molecular weight distribution, and high degrees of α- and ω-chain end-functionalization, they have been the subject of much study, as reported in several review articles and ACS symposia. See, for example, Qiu, J.; Charleux, B.; Matyjaszewski, K., *Prog. Polym. Sci.* 2001, 26, 2083; Davis, K. A.; Matyjaszewski, K. *Adv. Polym. Sci.* 2002, 159, 1; Matyjaszewski, K., Ed. Controlled Radical Polymerization; ACS: Washington, D.C., 1998; ACS Symposium Series 685. Matyjaszewski, K., Ed.; Controlled/Living Radical Polymerization. Progress in ATRP, NMP, and RAFT; ACS: Washington, D.C., 2000; ACS Symposium Series 768; and Matyjaszewski, K., Davis, T. P., Eds. Handbook of Radical Polymerization; Wiley: Hoboken, 2002, the disclosures of which are incorporated herein by reference.

The hydrophobic polymer backbone may be formed via radical polymerization of radically polymerizable monomers (including conventional of free radical polymerization as well as RDRP). Such monomers may include pendant groups as described above prior to polymerization. Alternatively, such pendant groups may be attached after polymerization. Representative monomers for use herein include styrene, acrylic acid, methacrylic acid, acrylonitrile, vinyl monomers and their derivatives. In a number of embodiments, the degree of polymerization for hydrophobic polymers hereof is, for example, less than 500.

Figure 3A:
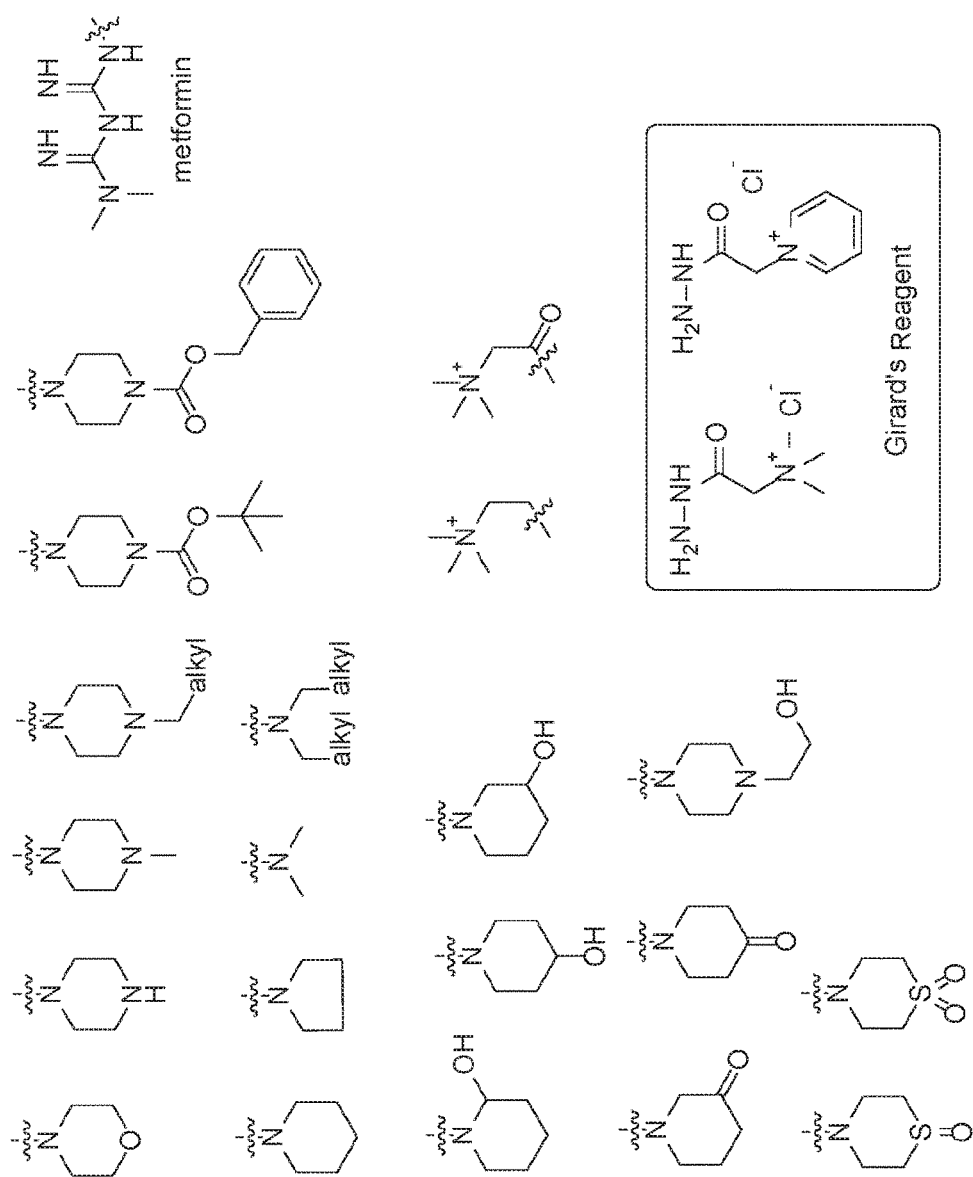
FIG. 3A illustrates representative examples of pendant groups (C, cationic groups) for the polymers hereof.
Figure 3B:
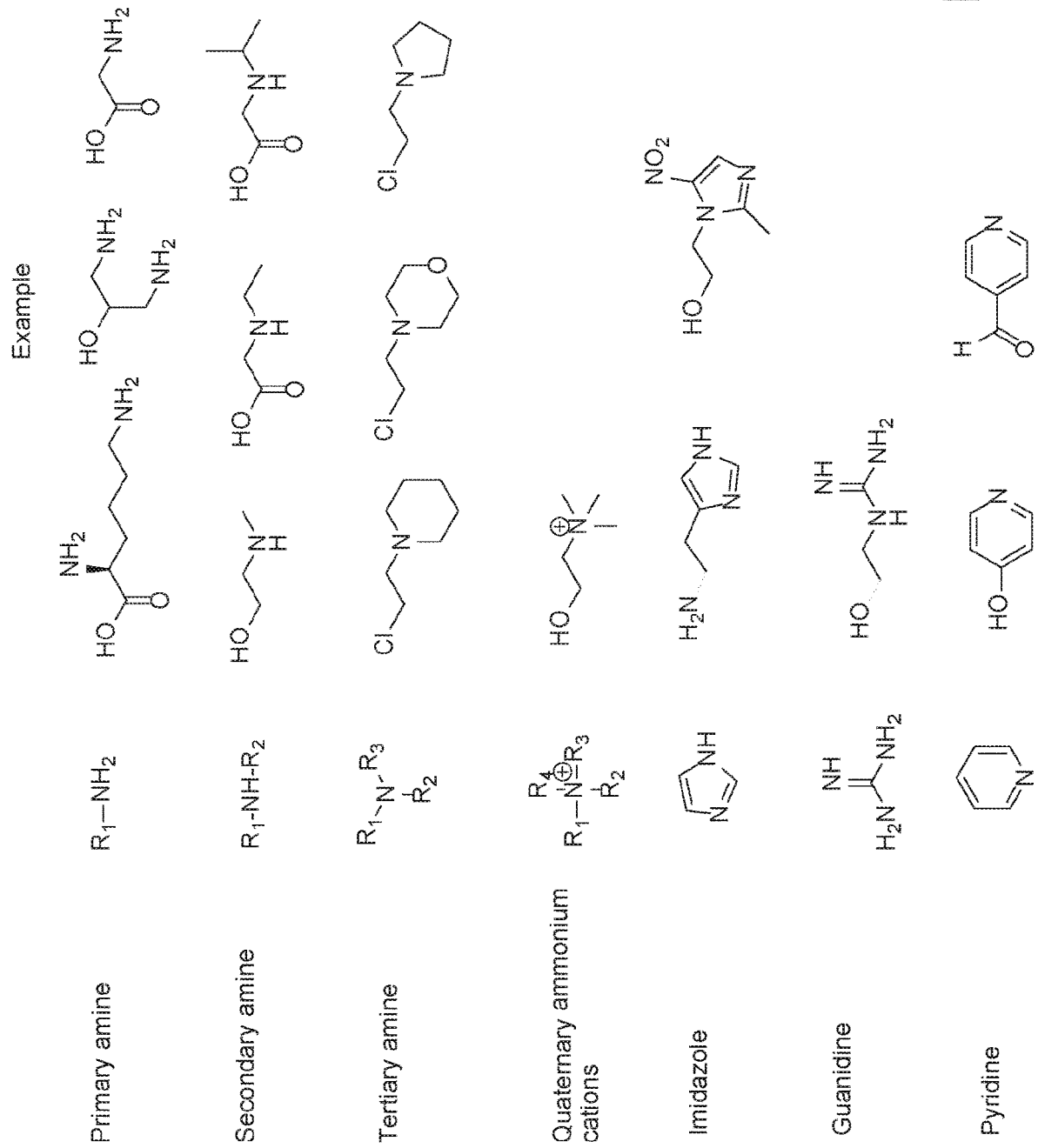
FIG. 3B illustrates further representative examples of pendant groups (C, cationic groups).
Figure 3C:
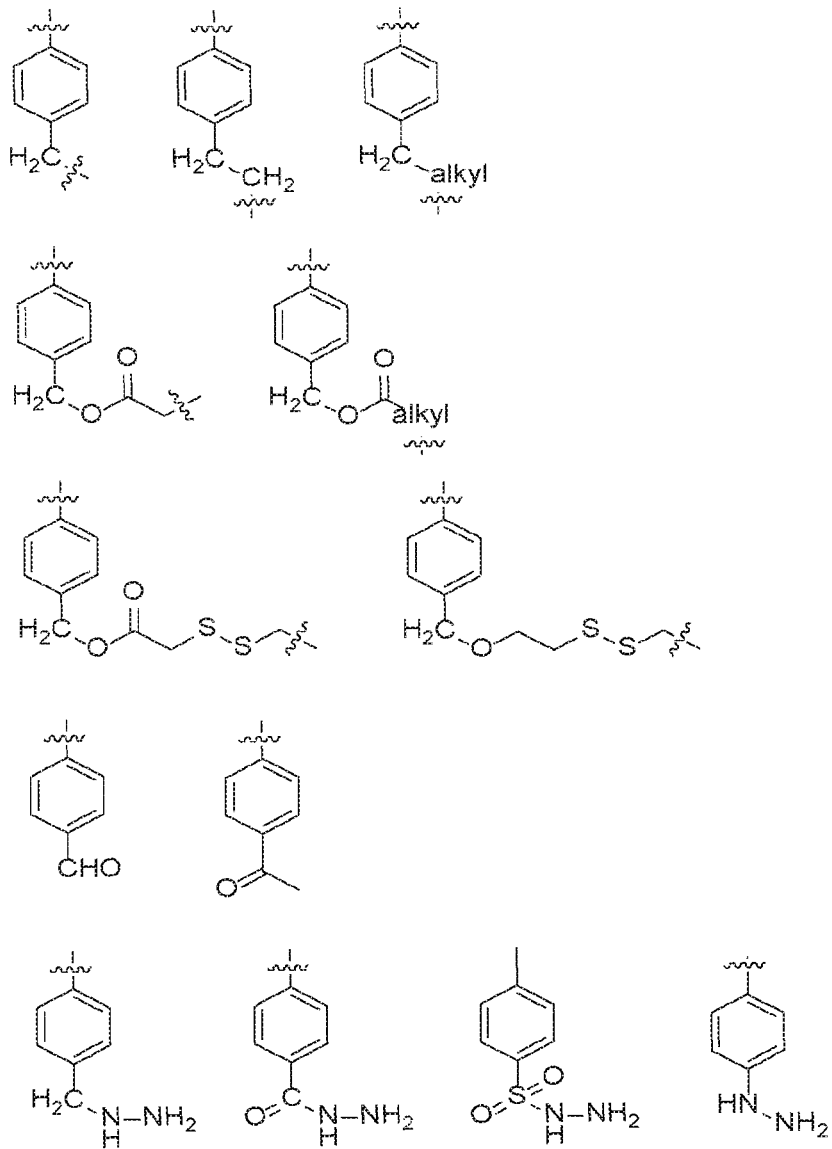
FIG. 3C illustrates representative examples of a first linking group ($L^1$) for the polymers hereof.

In a number of embodiments, the polymer further includes a first plurality of pendant groups (C) attached to the hydrophobic polymer backbone and including at least one cationic group and a second plurality of pendant groups attached to the hydrophobic polymer backbone and including at least one hydrophilic polymer (P). Representative examples of pendant groups (C) are set forth in FIGS. 3A and 3B. Pendant group hereof may also include both at least one cationic group and at least one hydrophilic polymer. In a number of embodiments, at least one of the first plurality of pendant groups and the second plurality of pendant groups is attached to the hydrophobic polymer backbone via a linking moiety. The linking moiety may include at least one group interactive via π-π stacking. The first plurality of pendant groups may, for example, be attached to the hydrophobic polymeric backbone via a first linking group ($L^1$). The first linking group ($L^1$) may, for example, include at least a first group which is interactive via π-π stacking. Representative examples of first linking group ($L^1$) are illustrated in FIG. 3C. The second plurality of pendant groups ($L^2$) may also be attached to the hydrophobic polymer backbone via a second linking group. The second linking group ($L^2$) may, for example, independently include at least a second group interactive via π-π stacking. Representative examples of the second linking group ($L^1$) are illustrated in FIG. 3D, wherein linker groups ($L^2$) are attached to a hydrophilic polymer P in the form of polyethylene glycol of PEG. The first linking group ($L^1$) and/or the second linking group ($L^2$) may, for example, include an aromatic group. In general, aromatic groups are cyclic molecules including resonance bonds that exhibit increased stability compared to other geometric or connective arrangements with the same set of atoms. Aromatic groups include, for example, benzyl and naphthyl groups. In a number of embodiments hereof, aromatic groups hereof are benzyl groups.

The at least one cationic group may, for example, include an inherently cationic group or a group which forms a cation in the formulations hereof and/or in vivo (for example, an amine group which forms a cation in vivo). The amine group may be an acyclic amine group, a cyclic amine group or a heterocyclic amine group. The at least one cationic group may, for example, be selected from the group consisting of a metformin group, a morpholine group, a piperazine group, a pyrrolidine group, a piperidine group, a thiomorpholine, a thiomorpholine oxide, a thiomorpholine dioxide, imidazole, guanidine or creatine. In a number of embodiments, the at least one cationic group is selected from the group consisting of a metformin group, a morpholine group, a piperazine group or creatine. The cationic amine groups described herein may be substituted or unsubstituted.

The hydrophilic oligomer or the hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiments, the at least one hydrophilic polymer is a polyalkylene oxide. The polyalkylene oxide may, for example, be a polyethylene glycol. A polyethylene glycol or other hydrophilic polymer hereof may, for example, have a molecular weight of at least 500 Da. In a number of embodiments, the polyethylene glycol of other hydrophilic polymer hereof has a molecular weight in the range of 200 Da to 10 KDa or a range of 500 to 5 KDa.

Pendant groups hereof (such as the second plurality of pendant groups) which include a hydrophilic polymer may, for example, be attached to the hydrophobic polymer backbone via a linking moiety that is labile under in vivo conditions (for example, under acidic pH conditions). The labile bond may, for example, be sensitive to conditions in a target region (for example, sensitive to or labile under acidic conditions in the region of a tumor). An acid-labile bond may, for example, include a carboxydimethyl maleate, a hydrazine, an imine, an acetal, an oxime, a silyl ether, a cis-asonityl or another acid-labile bond or linkage. Use of a labile bond that is sensitive to acidic conditions may be used to cleave the hydrophilic polymer/oligomer in, for example, an acidic tumor environment. Examples of other suitable labile bonds include disulfide bonds, hypoxia sensitive bonds and glucose-sensitive bonds.

A formulation hereof may, for example, include a plurality of polymers (as described above) which are formed via radical polymerization to have a hydrophobic polymer backbone, a first plurality of pendant groups attached to the hydrophobic polymer backbone and including at least one cationic group and a second plurality of pendant groups attached to the hydrophobic polymer backbone and including at least one hydrophilic polymer. The formulation may further include a first therapeutic compound and a second therapeutic compound, wherein the second therapeutic compound is different from the first therapeutic compound and includes a nucleic acid. The first therapeutic compound may, for example, be a hydrophobic compound that does not include a nucleic acid. The first therapeutic compound may, for example, be a small molecule therapeutic compound. Such small molecule therapeutic compounds may, for example, have a molecular weight below 2.0 kDa, below 1.5 kDa or below 1.0 kDa. The second therapeutic compound may, for example, include RNA or DNA. In a number of embodiments, the second therapeutic compound include includes a gene or siRNA. In general, any nucleic acid including negative charges may be used in the formulation hereof including naturally occurring and synthetic nucleic acids (for example, RNA, DNA, locked DNA etc.).

In formulations for delivery of compounds in vivo, a plurality of polymers hereof may assemble/self-assemble into structures. A plurality of polymers hereof may, for example, form micelles. Without limitation to any mechanism, the plurality of nucleic acid compounds may interact with cationic groups of the first plurality of pendant groups to stabilize such micelles.

Figure 4:
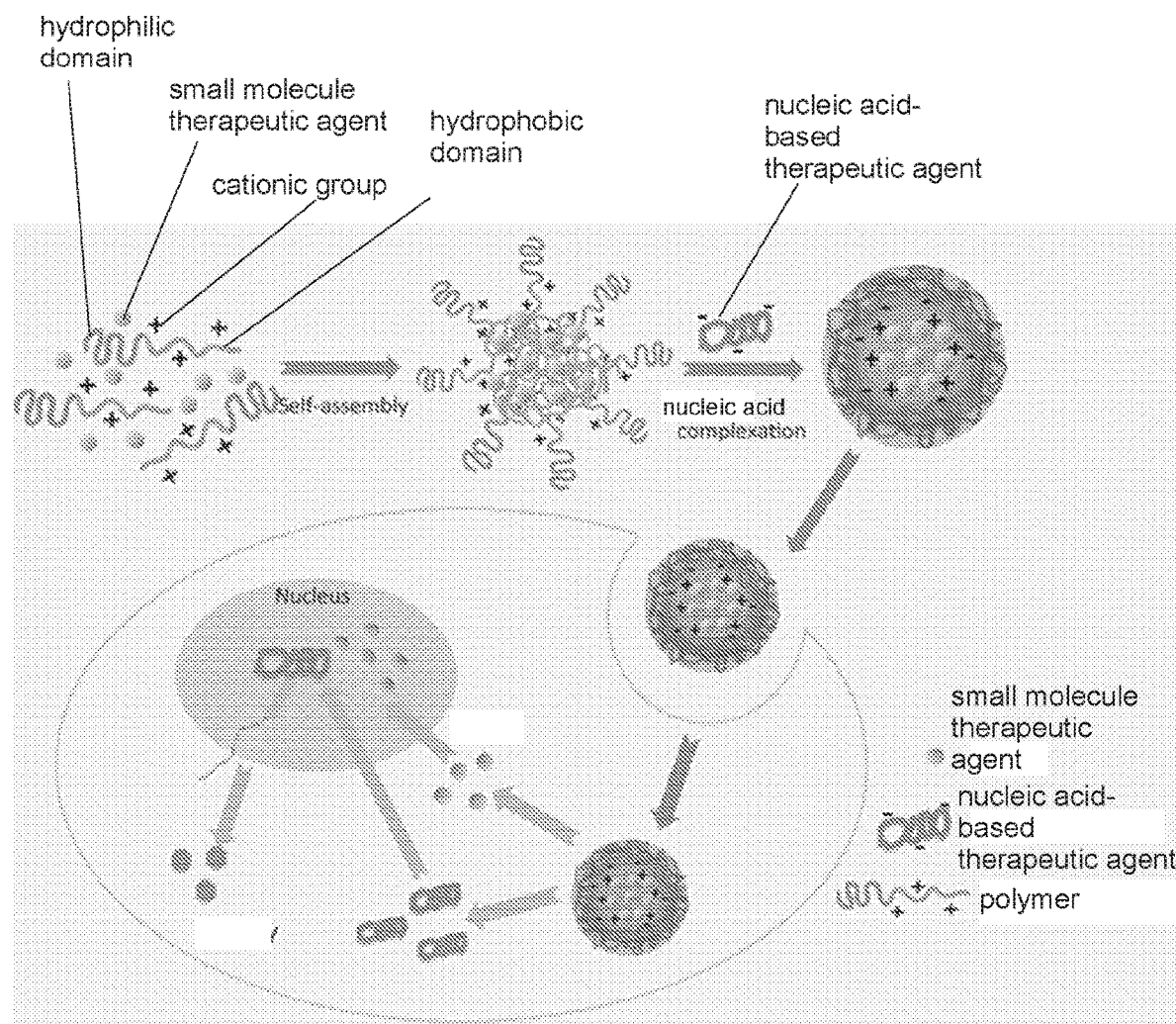
FIG. 4 illustrates an idealized schematic representation of a formulation hereof including a nucleic acid-base therapeutic agent, compound or drug and a small-molecule therapeutic agent, compound or drug loaded onto a micelle carrier structure formed with the polymers hereof.

FIG. 4 sets forth an idealized schematic representation of a nucleic acid-base therapeutic agent, compound or drug (for example, a gene, a plasmid, siRNA etc.) and a small-molecule therapeutic agent, compound or drug loading onto a micelle carrier structure formed with the polymers hereof. FIG. 4 further illustrates multifunctional nanocarriers hereof as co-delivery platforms for cells such as cancer cells. As used herein a therapeutic agent or drug is a biologically active substance which has an effect on the body (for example, a medicinal or therapeutic effect, an intoxicating effect, a performance enhancing effect or another effect). A therapeutic agent may, for example, be an antibody, an antibiotic, an antiviral, an antimycotic, an anticancer agent, an immunosuppressant, a chemotherapeutic agent, an anti-rejection agent, an analgesic agent, or an anti-inflammatory agent. Small molecule drugs suitable for use herein include, but are not limited to JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl)oxymethyl-5-isopropylisoxazole), rose bengal, epigallo-catechin gallate, curcumin, indomethacin, tamoxifen. NLG-919 (an indoleamine 2,3-dioxygenase (IDO) pathway inhibitor), sunitinib, imatinib, erlotinib, fluorouracil (5-FU), a c-Myc inhibitor such as 10058-F4 (5-[(4-Ethylphenyl)methylene]-2-thioxo-4-thiazolidinone) or doxorubicin.

Without limitation to any mechanism, and with reference to FIG. 4, it is hypothesized that an inwardly oriented hydrophobic domain is created during micelle formation via the hydrophobic backbone of the polymers hereof, which may orient via intrachain hydrophobic interactions to assume a folded conformation. Pendant aromatic groups, when present, increase hydrophobicity and assist in forming the hydrophobic domain. It was further hypothesized that an outwardly oriented hydrophilic domain was formed by the hydrophilic polymer side chains. Cationic groups likely assume a conformation to orient toward the hydrophilic domain near the interface of the hydrophobic and hydrophilic domains or intermediate therebetween.

In a number of embodiments, delivery systems prior to the present invention were designed for delivery of either small molecule drugs or nucleic acid-based therapeutics. In the present studies, we have developed a simple micellar system that is highly effective in codelivery of small molecules drugs and nucleic acids (for example, siRNA, genes, plasmids, etc.). In addition to providing a platform for new combination therapies that involves both small molecule drug therapeutics and nucleic acid therapeutics, the carrier systems hereof also resolve an issue of instability that is associated with most micellar carrier systems. Micelles are formed through the self-assembly of amphiphilic monomers, which is a reversible and dynamic process. Micelles tend to fall apart when they are diluted in the blood upon systemic administration. This instability can be further aggravated by lipid exchange as a result of interactions with lipoproteins in the blood. A number of strategies have been reported to create cross-linking bonds between amphiphilic molecules to stabilize the micelles. Some of the approaches involve a complicated procedure and/or modification of the structure of the amphiphilic molecules. In the systems hereof, multi-valent charge-charge interactions between the cationic groups of the amphiphilic polymer molecules and nucleic acids serve as a simple approach to create interactive, non-covalent crosslinks between amphiphilic polymeric molecules of the micelles hereof. Moreover, π-π interactions stacking between the amphiphilic polymer molecules and nucleic acids may additionally or alternatively be used to create interactive, non-covalent crosslinks between amphiphilic polymeric molecules of the micelles hereof π-π interactions or stacking between the groups of amphiphilic polymers forming micelles and numerous compounds such as drugs are, for example, discussed in U.S. Pat. Nos. 10,172,795 and 9,855,341 and U.S. Patent Publication No. 2018/0214563, the disclosure of which are incorporated herein by reference. As a result, micelles hereof that are co-loaded with small molecules and nucleic acid-based molecules are more stable than free micelles or the micelles that are loaded with small molecules alone.

In several representative embodiment, a multifunctional delivery system hereof based on an amphiphilic polymer with morpholine attached to the pendant side chains (POEG-st-Pmor; wherein POEG represents polyoxyethylene glycol and mor represents morpholine) for codelivery of small molecule chemotherapy drugs and plasmid DNA. The hydrophobic anticancer drugs may, for example, be incorporated into the hydrophobic core through hydrophobic-hydrophobic interaction and π-π stacking. Morpholine is incorporated into the polymer to introduce positive charges to form complexes with nucleic acids as described above. The positively charged morpholine groups in the polymers may also facilitate the accumulation of the carrier in the lung as a result of the interaction of positively charged tertiary amine with negatively charged cell membrane in the lung. In a number of representative studies, doxorubicin (DOX) and IL-36γ plasmid were selected as a model/representative drug and model/representative nucleic acid (DNA), respectively for study of combination therapies hereof. DOX is a first-line chemotherapeutic drug in the treatment of a broad range of cancers including breast, ovary, bladder, and lung cancers, and breast cancer metastasis. Cytokines are reported to have a synergistic antitumor effect in combination with conventional antitumor treatments such as chemotherapy. Interleukin 36 (α, β, γ) belongs to IL-1 family of cytokines, and the three isoforms share the same receptor complex. IL-36γ is reported to promote the differentiation of type 1 effector lymphocytes, including $CD8^+$, NK, and γδT cells in vitro. The tumoral expression of IL-36γ exerts strong antitumor immune responses in vivo and transforms the tumor microenvironment in favor of tumor eradication. Codelivery of DOX and IL-36γ plasmid via the multifunctional carrier hereof represents a simple and effective approach for the treatment of lung metastasis. The biophysical properties of the nanocarrier co-loaded with DOX and IL-36γ plasmid was first examined. The efficiency of delivery and transfection was then examined both in vitro and in vivo. Finally, the antitumor effect of DOX+IL-36γ plasmid/polymer as well as the underlying mechanism was investigated.

Figure 5:
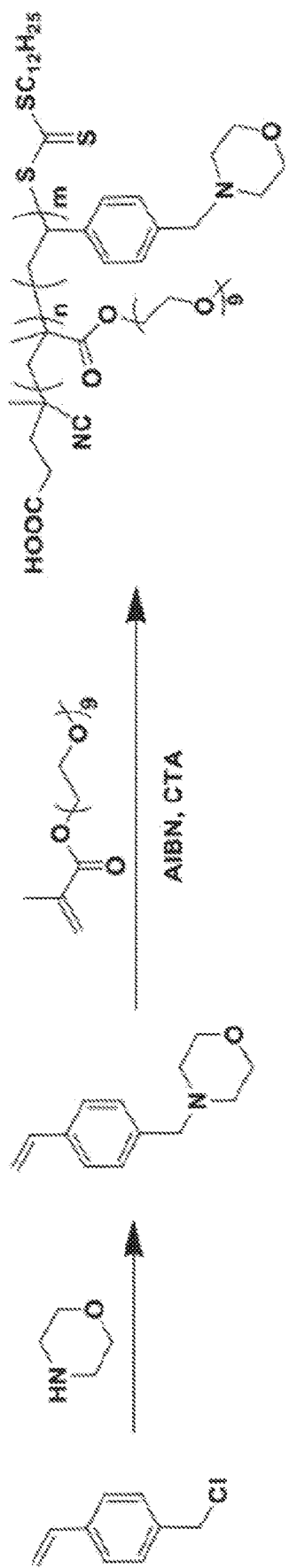
FIG. 5 illustrates a synthetic scheme for a POEG-st-Pmor polymer hereof.

The synthesis scheme for POEG-st-Pmor polymer was shown in FIG. 5. First, VBMor monomer was synthesized by reacting vinylbenzyl chloride with morpholine. The structure of VBMor monomer was confirmed by 1H NMR. Then, POEG-st-Pmor copolymer was prepared via reversible addition-fragmentation chain-transfer (RAFT) polymerization of OEG500 monomer and VBMor monomer. The structures and molecular weight of POEG-st-Pmor polymer were characterized by 1H NMR and gel permeation chromatography (GPC). The average degree of polymerization (DP) of the OEG500 monomer was calculated to be 10 according to the conversion of OEG500 monomer at the end of the polymerization (conversation: 70%). The DP of the VBMor monomer was determined to be 60 by comparing intensities. The average molecular weight Mn of POEG-st-Pmor polymer determined by GPC was 9260, and the polydispersity is 1.13 as determined by gel permeation chromatography, which indicated the successful synthesis of POEG-st-Pmor copolymer with well-defined structure. Although a narrow polydispersity (for example, below 1.75, below 1.5 or below 1.25) may result in formation of more uniform micelles, it is not clear whether in vivo performance of formulation hereof is improved with narrower polydispersity.

Figure 6A:
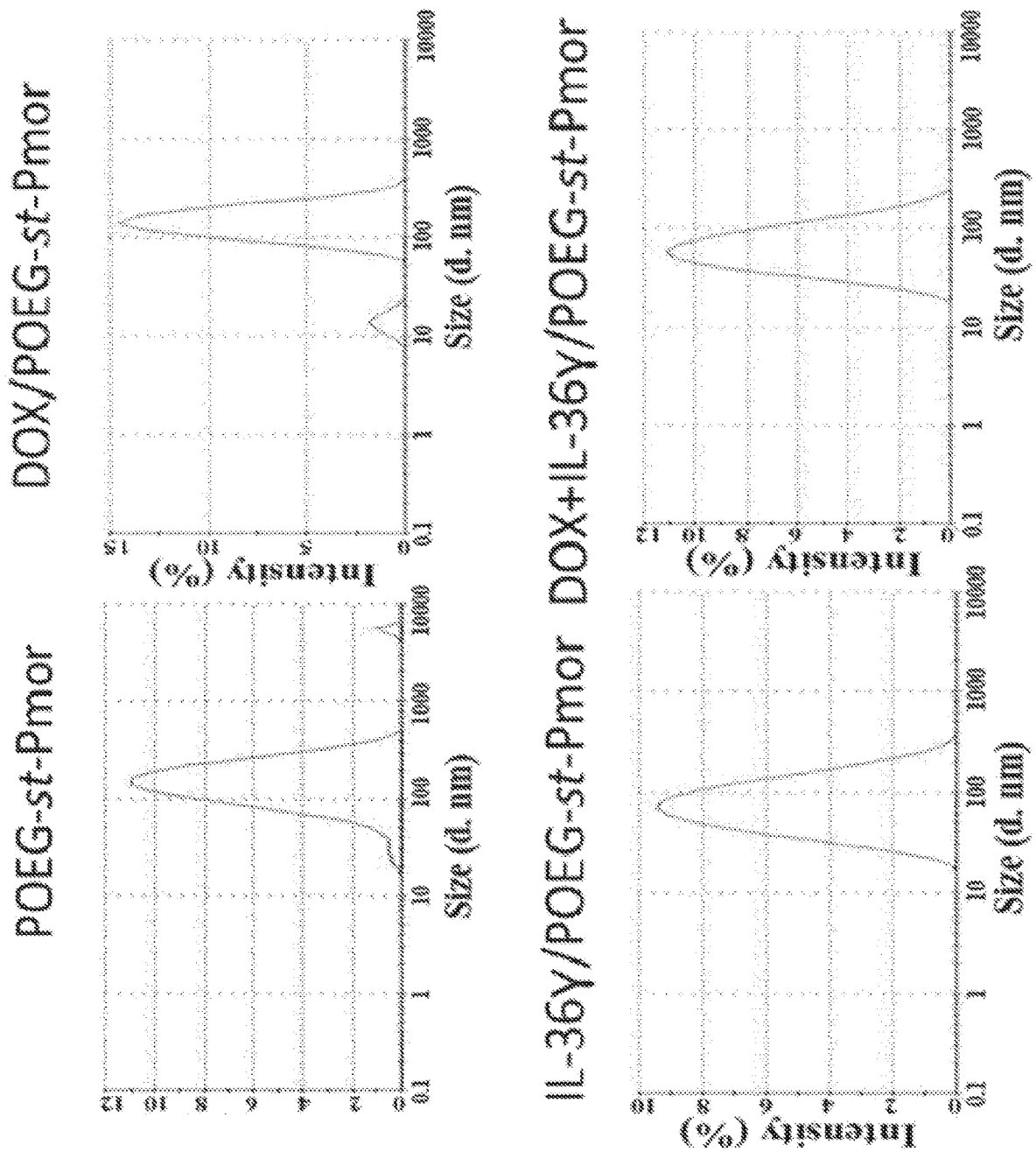
FIG. 6A illustrates the results of studies of POEG-st-Pmor micelles with a zetasizer.
Figure 6B:
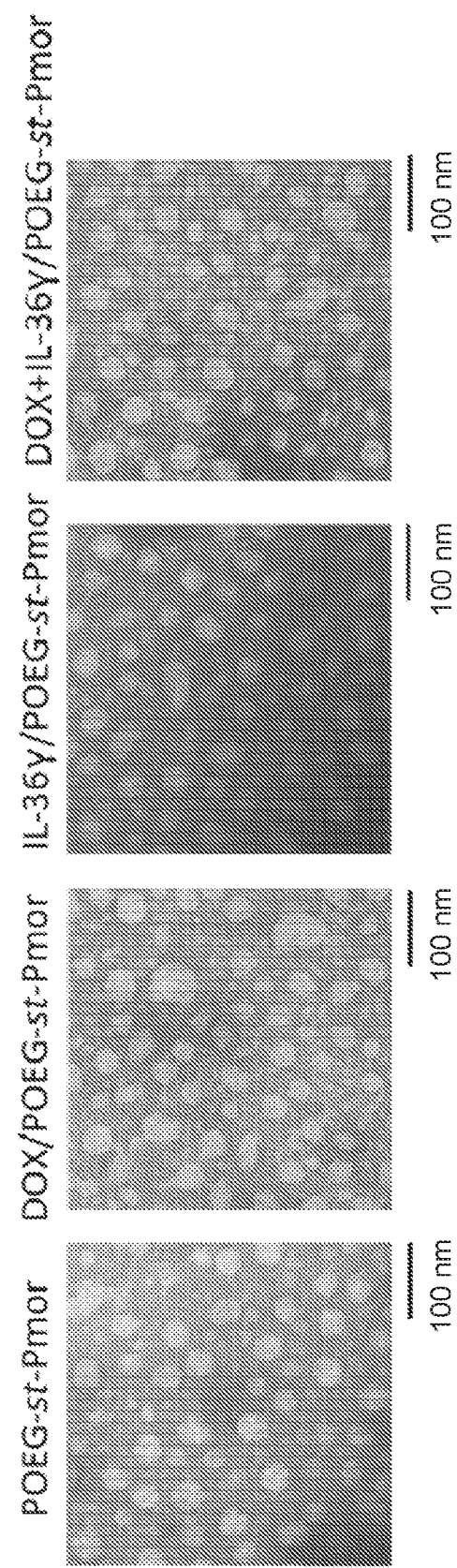
FIG. 6B illustrates TEM images of POEG-st-Pmor micelles (blank micelles, DOX-loaded micelles and IL-36γ plasmid complexed micelles and micelles co-loaded with IL-36 γ and DOX) wherein the scale bars are 100 nm.

POEG-st-Pmor micelles were prepared via a dialysis method. As shown in FIGS. 6A and 6B, POEG-st-Pmor micelles had sizes around 200 nm as tested with a zetasizer. Spherical structure was observed by TEM. The size tested by TEM is smaller than that by DLS, which may be a result the different principles of analysis and the shrinkage of dried micellar nanoparticles during TEM measurement. The critical micelle concentration (CMC) of the polymer was determined using nile red as a fluorescence probe. POEG-st-Pmor has a low CMC around 0.04 mg/ml.

The DOX-loaded POEG-st-Pmor micelles were similarly prepared as blank micelles. POEG-st-Pmor carrier could load DOX at a carrier/drug mass ratio starting from 10:1 with sizes ranging from 160 to 190 nm (FIGS. 6A and 6B, Table 1, setting forth Biophysical characteristics of blank micelles and the micelles co-loaded with IL-36γ plasmid and DOX) and the formulation could remain stable for two weeks at room temperature. Then we tested whether the POEG-st-Pmor could form stable complexes with plasmid DNA. A gel retardation assay was performed to assess the pDNA binding ability of the pMor-based polymer. Plasmid DNA/carrier complexes were fabricated at N/P ratios from 0.1:1 to 30:1. As known to those skilled in the art, the N/P ratio refers to the number of cationic carrier nitrogens/to DNA phosphates. Complete complexation of plasmid DNA by POEG-st-Pmor polymer was achieved at an N/P ratio of 5/1 or greater. To further study the interaction between DNA and carrier, a competitive binding gel-shift assay with dextran sulfate was performed. Substantial amounts of DNA were released from control PEI/DNA complexes at an S/P ratio (molar ratio between the sulfur from dextran sulfate and the phosphate from pDNA) as low as 15/1. In contrast, no obvious release of DNA was observed for POEG-st-Pmor/DNA complexes at an S/P ratio as high as 40/1.

TABLE 1

| Micelles | Mass ratio (mg:mg) | N/P ratio | Size (nm) | Zeta potential (mV) | Stability |
|---|---|---|---|---|---|
| POEG-st-Pmor | — | — | 184 ± 3.5 | 26.4 ± 1.1 | — |
| IL-36γ/ POEG-st-Pror | — | 20 | 95.0 ± 1.8 | 10.3 ± 0.1 | — |
| DOX/ POEG-st-Pmor | 10:1 | — | 178 ± 2.1 | 27.1 ± 0.7 | 2 weeks |
|  | 20:1 | — | 174 ± 1.5 | 24.7 ± 0.9 | 4 weeks |
|  | 30:1 | — | 162 ± 4.1 | 26.01 ± 0.7 | 1 month |
| DOX+IL-36γ/ POEG-st-Pmor | 20:1 | 20 | 84.4 ± 1.7 | 10.4 ± 0.2 | 1 month |

*The colloidal stability was followed at room temperature by measuring the size and observing precipitates.

Figure 7A:
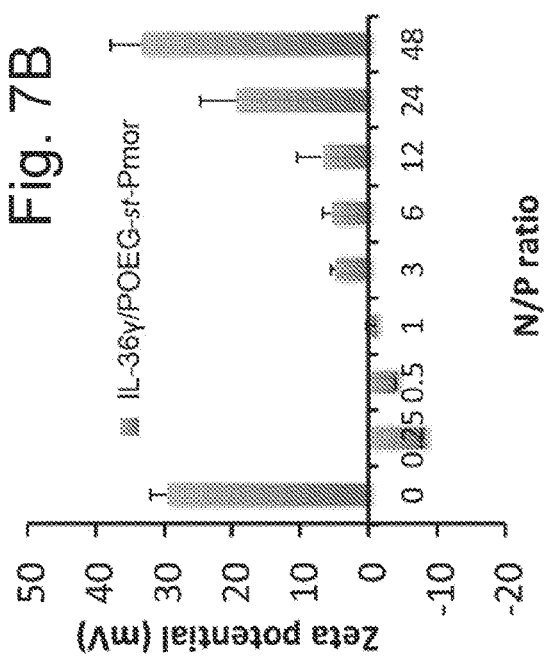
FIG. 7A illustrates the size of POEG-st-Pmor blank micelles as a function of N/P ratio.
Figure 7C:
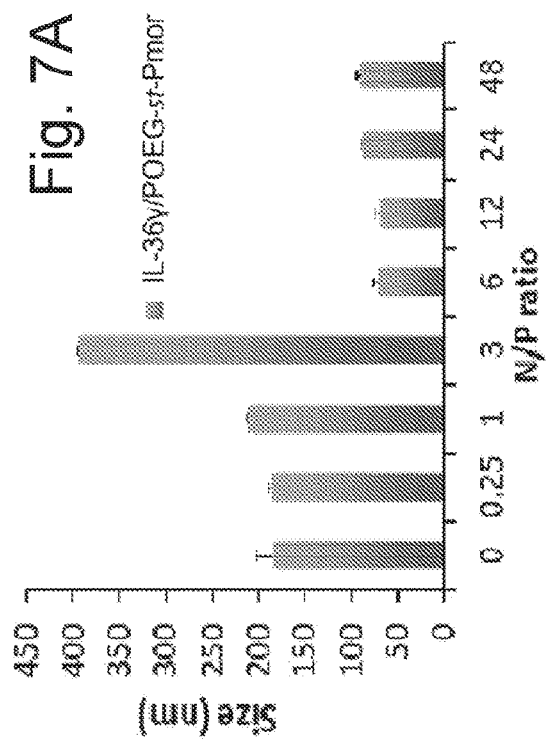
FIG. 7C illustrates a study of the effect on particle size over time upon exposure to BSA solution.
Figure 7B:
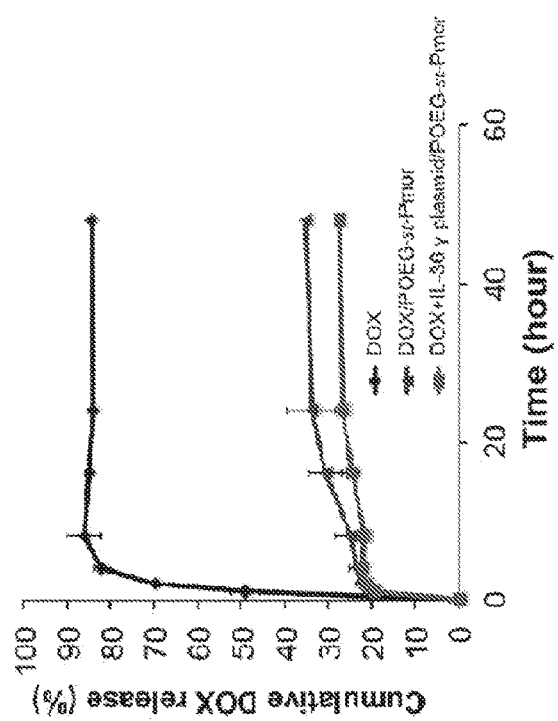
FIG. 7B illustrates zeta potential of POEG-st-Pmor blank micelles as a function of N/P ratio.

The surface zeta potential of the POEG-st-Pmor blank micelles was 26.4 mV before the addition of IL-36γ plasmid (FIGS. 7A and 7B and Table 1). At the N/P ratios of below 1, the complexes were negatively charged and the particle sizes were similar to the sizes of the micelles alone. There was a significant increase in the sizes of the complexes at an N/P ratio of 3. At this ratio, the particle charges were close to neutral. Further increases in the N/P ratios led to a significant decrease in the particle sizes and the particles became more positively charged with continuous increases in the N/P ratios. Specifically, when the micelles were mixed with IL-36γ plasmid at an N/P ratio of 20:1, the average size of the complexes decreased to 70-80 nm (Table 1, FIG. 7A). Nonetheless, DNA/micelle complexes were less positively charged compared to free micelles with a surface zeta potential of 10.3 mV (Table 1).

We then went on to further explore the possibility of co-delivery of pDNA and DOX by POEG-st-Pmor micelles. As shown in FIG. 6A and Table 1, the size distribution and zeta-potential were not significantly affected when DOX was loaded into the pDNA/polymer complexes at a drug concentration of 1 mg/mL and a carrier/drug ratio of 20/1 (w/w).

The colloidal stability of micelle/DNA complexes was tested in BSA solution (30 mg/mL). PEI/DNA complexes were used as a control (N/P=20, zeta potential=18.3 mV). As shown in FIG. 7C, exposure of PEI/DNA complexes to BSA led to a rapid increase in the particle sizes. At 5 h post-incubation, the sizes of PEI/DNA complexes increased from 149 to 261 nm. It is also apparent that POEG-st-Pmor/DNA complexes were resistant to BSA-induced aggregation and showed minimal changes in sizes throughout the entire 18 h of observation.

Figure 7D:
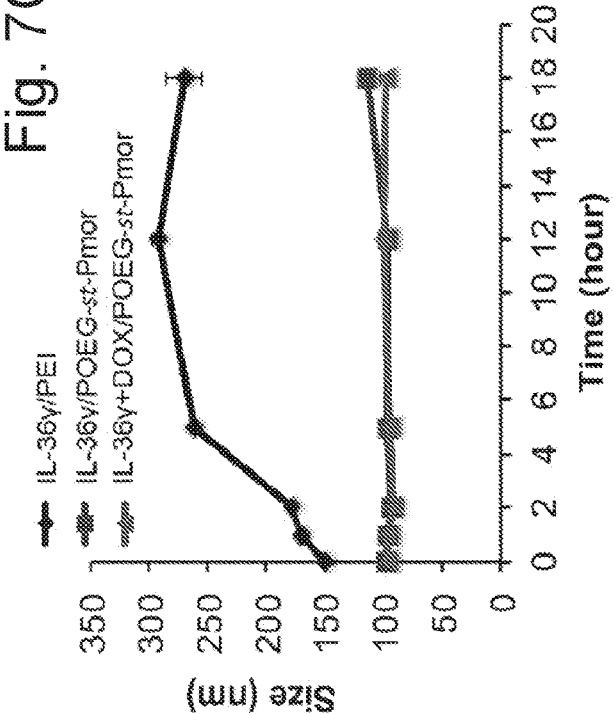
FIG. 7D illustrates a study of DOX release from several DOX-loaded micelles over time by a dialysis method with DOX.HCl solution as a control.

The profile of DOX release from the DOX-loaded micelles was examined by a dialysis method with DOX.HCl solution as a control (FIG. 7D). Free DOX was rapidly diffused out of the dialysis tubing with 80% of DOX found in the dialysate in the first 4 hours. However, DOX formulated in POEG-st-Pmor micelles showed a slow kinetics of release with less than 25% of DOX released outside of dialysis bag at the first 4 hours, and only 35% of DOX released at 24 h. The micelles co-loaded with DOX and plasmid exhibited an even slower DOX release profile compared to micelles loaded with DOX alone at later time points. The polymer concentration inside the dialysis bag was far above the CMC value and the micelles were stable throughout the entire course of release study.

Most delivery systems developed so far are designed for delivery of either small molecule drugs or nucleic acid-based therapeutics. The readily formulized micellar systems hereof are highly effective in codelivery of both small molecules and nucleic acids (for example, plasmid DNA). Various mechanisms are likely to be involved in the formation of free micelles and drug- or drug/gene-loaded micelles. While the hydrophobic interaction and π-π stacking drive the formation of a compact particle, the positive charge-mediated repulsion may impose a negative force on the formation of such particle. Loading of DOX into the micelles led to a small decrease in particle sizes (180 vs 160 nm): this may, for example, be a result of formation of a more compacted particle, which is facilitated by the carrier-DOX interactions. The particle size was more dramatically reduced following the complexation of the micelles with plasmid DNA in the presence or absence of DOX: the size decreased from 180 nm to about 100 nm. The interaction of large-sized plasmid DNA with the positively charged micelles results in a non-covalent cross-linking of micelles. In addition, charge neutralization of DNA is known to induce DNA condensation. Together, these characteristics drive the formation of a more compact hydrophobic core and thus significantly decreased particle size. The significantly increased particle size at an N/P ratio of 3/1 may, for example, be a result of a status of neutral surface, which drives the aggregation of the nanomicelles. On the other hand, the excess surface positive charges at N/P ratios of above 3/1 help to maintain the colloidal stability of the "condensed" nanomicelles through charge-mediated repulsion. Another advantage provided by the nanomicellar formulation hereof is improved stability. As described above, micelles are formed through the self-assembly of amphiphilic monomers, which is a reversible and dynamic process. Once again, micelles tend to fall apart when they are diluted in the blood upon systemic administration. This instability can be further aggravated by lipid exchange as a result of interactions with lipoproteins in the blood. In the systems hereof, the multivalent charge-charge interactions between the cationic polymer and nucleic acid (plasmid DNA, in the current example) serve as a simple approach to "cross-link" the micelles. As a result, micelles that are co-loaded with small molecules and plasmid DNA are likely to be more stable than free micelles or the micelles that are loaded with small molecule alone. This observation is supported by the data from DOX release studies. DOX formulated in the co-loaded nanoparticles exhibited a slower kinetics of release compared to the formulation that is loaded with DOX only (FIG. 7D).

Figures 8A, 8B:
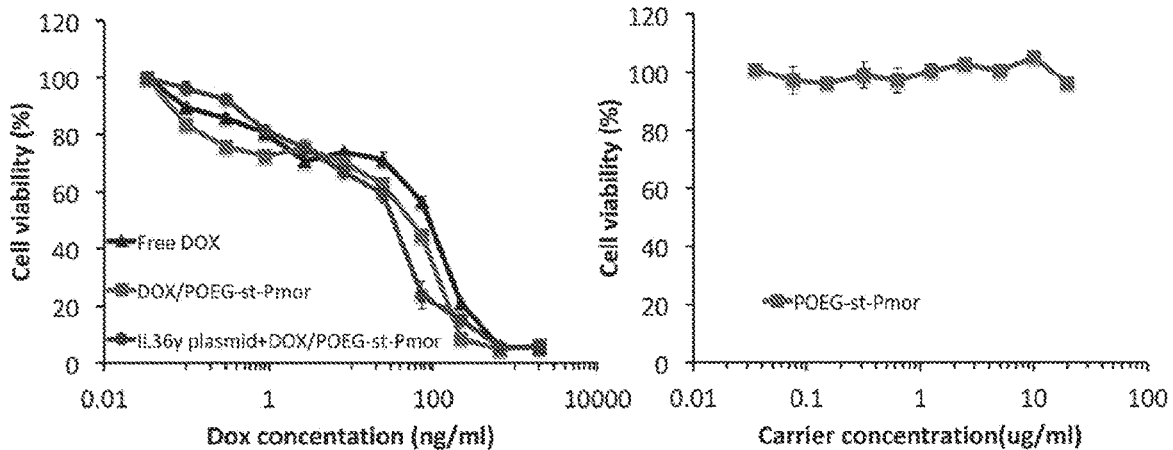
FIG. 8A illustrates a study of in vitro cytotoxicity of DOX+IL36γ plasmid/micelle complexes with 4T1.2 breast cancer cells as a function of DOX concentration via MTT assay.
FIG. 8B illustrates a study of in vitro cytotoxicity of POEG-st-Pmor alone, demonstrating minimal cytotoxicity to 4T1.2 cells at polymer concentration as high as 20 μg/mL.

The in vitro cytotoxicity of DOX+IL36γ plasmid/micelle complexes was evaluated with 4T1.2 breast cancer cells via MTT assay. Cells received various treatments for 72 h and the final concentrations of DOX ranged from 4 to 1000 ng/mL (FIG. 8A). The free DOX and the DOX-loaded micelles showed a dose-dependent cell killing profile. The DOX/POEG-st-Pmor micelles had lower IC50s (60 ng/ml) compared to free DOX (130 ng/ml) (FIG. 8A). Incorporation of IL36γ plasmid into DOX-loaded micelles led to slightly increased cytotoxicity on 4T1.2 cells. POEG-st-Pmor alone showed minimal cytotoxicity to 4T1.2 cells at the polymer concentration as high as 20 µg/mL (FIG. 8B).

The cellular uptake of DOX-loaded POEG-st-Pmor micelles was investigated by confocal laser scanning microscopy with free DOX as a control. At 2 h of incubation, DOX-loaded POEG-st-Pmor micelles showed more DOX cellular uptake compared to free DOX at the same DOX concentration. The signals for free DOX were largely found in the nucleus while the signals for the micellar DOX were mainly located outside the nucleus. This may, for example, be a result of different cellular uptake routes of free DOX and DOX micelles.

Using EGFP as a reporter gene, we investigated if POEG-st-Pmor carrier could effectively deliver EGFP plasmid into 4T1.2 cultured cells and tumor tissues, leading to expression of biologically active protein. The studies showed that 4T1.2 tumor cells were effectively transfected with EGFP plasmid complexed with POEG-st-Pmor micelles. 4T1.2 cells were also effectively transfected with branched PEI, a control carrier.

In studies of the in vivo EGFP expression in tumor, lung and liver tissues, there were significantly more EGFP signals in tumors with POEG-st-Pmor formulation compared to linear PEI. In agreement with previous reports, lungs could be effectively transfected by linear PEI. However, more and stronger signals of EGFP were observed in lungs transfected with POEG-st-Pmor formulation. The liver was hardly transfected with either the formulation hereof or the control linear PEI. These results indicate that POEG-st-Pmor polymer is suitable for in vivo gene delivery to both lungs and distant solid tumors.

The complexes of DNA with POEG-st-Pmor polymer were significantly more stable than PEI/DNA complexes following exposure to BSA (30 mg/mL). This may, for example, be a result of the dynamic shielding of the complexes by PEG despite the fact that both complexes remain positively charged. The improved stability of the complexes in the presence of serum proteins may contribute to the efficient delivery of DNA to distant subcutaneous or s.c. tumors. A more effective accumulation in the lung may, for example, be a result of the interaction of tertiary amine moiety with negatively charged cell membrane in the lung. Amine-containing basic compounds have been reported to be predominantly accumulated in the lung due to the specific binding to acidic phospholipids on the cell membrane, which is abundantly distributed in lung tissue. Therefore the carriers hereof are suitable for codelivery of nucleic acid therapeutics and small molecule drugs to both distant solid tumors and lung metastatic lesions.

POEG-st-Pmor was more effective than PEI in transfecting either lungs or distant s.c. tumor tissues in vivo. The higher in vivo transfection efficiency of POEG-st-Pmor polymer may, for example, be a result of the enhanced stability of DNA/POEG-st-Pmor complexes in blood circulation due to the PEG shielding. It is also possible that POEG-st-Pmor form more stable complexes with DNA compared to PEI. Single or double-strand DNA may bind to nanoparticles through electrostatic, π-π stacking and hydrophobic interactions or even central cavity insertion. In addition to charge-charge interaction, the hydrophobic backbone of the polymers hereof and the pendant benzene rings can further interact with the base π-systems of nucleic acids through π-π stacking and hydrophobic interactions. This observation was supported by results from competitive binding gel-shift assay studies showing that the pDNA could hardly be released from POEG-st-Pmor micelles by dextran sulfate at an S/P ratio as high as 60. In contrast, substantial amounts of DNA were readily released from DNA/PEI complexes by dextran sulfate at an S/P ratio as low as 15/1.

Figure 9A:
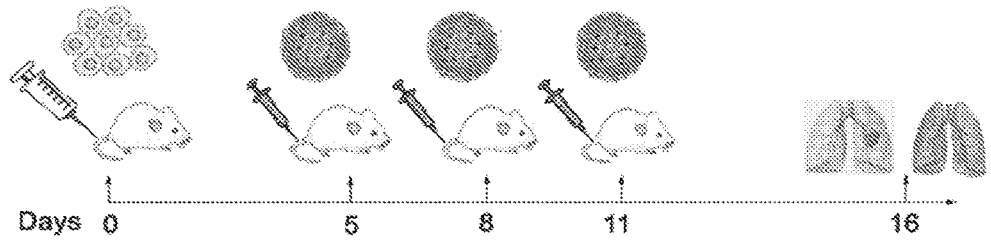
FIG. 9A illustrates a mouse model study of breast cancer lung metastasis (4T1.2) generated in female Balb/c mice via tail vein injection.
Figures 9B, 9C:
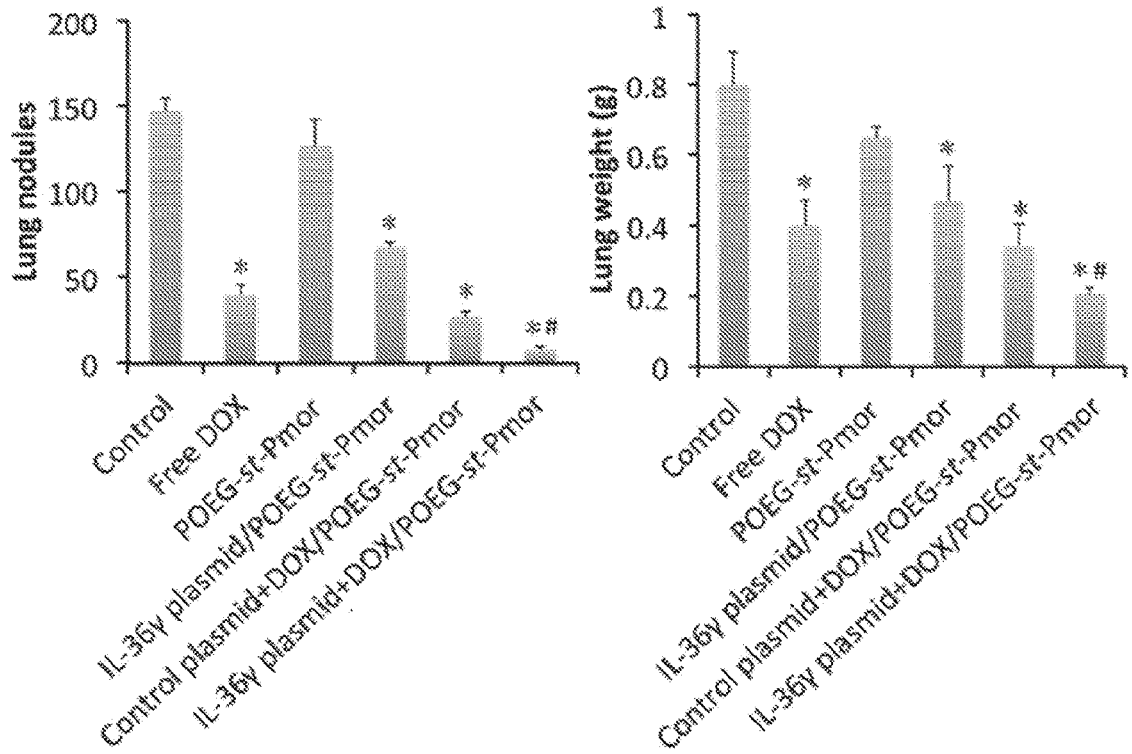
FIG. 9B illustrates lung tumor nodules as a function of treatment with various compositions.
FIG. 9C illustrates lung weights as a function of treatment with various compositions.
Figure 9D:
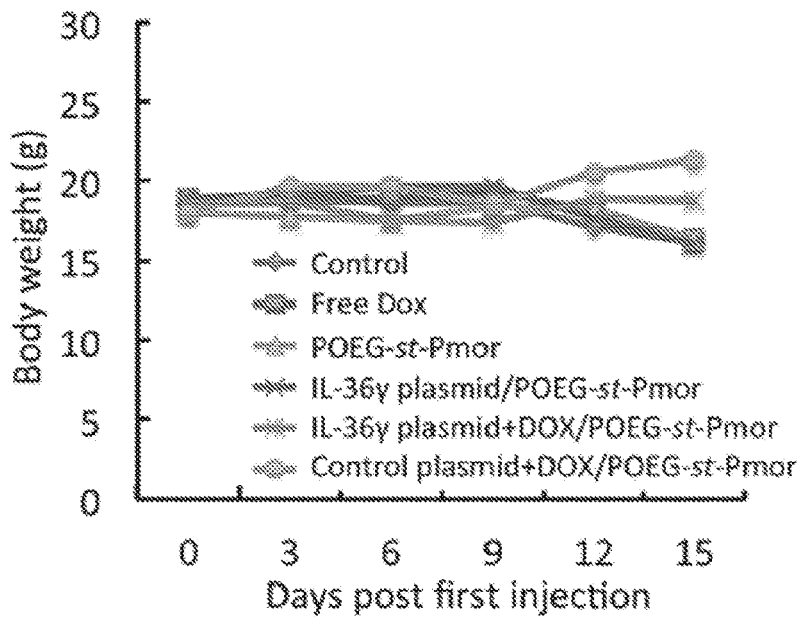
FIG. 9D illustrates a study of body weights during the treatment period for various compositions.

A mouse model of breast cancer lung metastasis (4T1.2) was generated in female Balb/c mice and various treatments were given to each group of mice via tail vein injection (FIG. 9A). The carrier alone did not show therapeutic activity compared to control group. Free DOX showed a significant inhibition of lung metastasis and the antitumor activity was further enhanced for micelles co-loaded with DOX and IL-36γ plasmid compared to free DOX, DOX+control plasmid/micelles and IL-36γ plasmid/micelles. The H&E (haemotoxylin and eosin) staining of lung tissues showed clear tumor cell infiltration in all of the groups except the co-delivery group. The group with more tumor nodules had more lung weights (FIGS. 9B and 9C). Body weights were also monitored during the treatment period. No significant decrease of body weight was observed, indicating the safety of the formulation (FIG. 9D).

POEG-st-Pmor alone was not active in the 4T1.2 lung metastasis model. Free DOX or delivery of IL-36γ alone via POEG-st-Pmor polymer showed a significant activity in inhibiting the lung metastasis. Combination of the two led to a further improvement in antitumor activity as shown by both smallest number of tumor nodules in the lung and the lowest weights of the tumor-bearing lungs (FIGS. 9B and 9C).

Figure 10A:
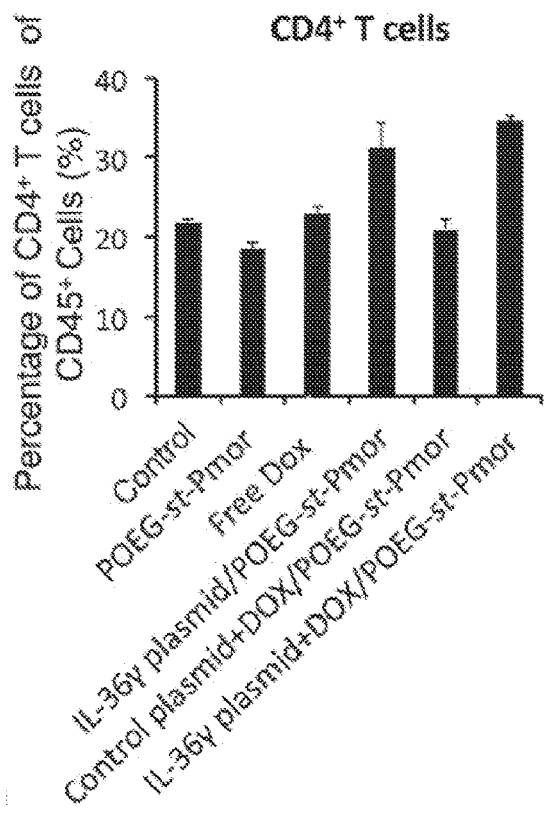
FIG. 10A illustrates a study of cytotoxic $CD4^+$ T cells in lung tissues for treatment with various compositions.
Figure 10B:
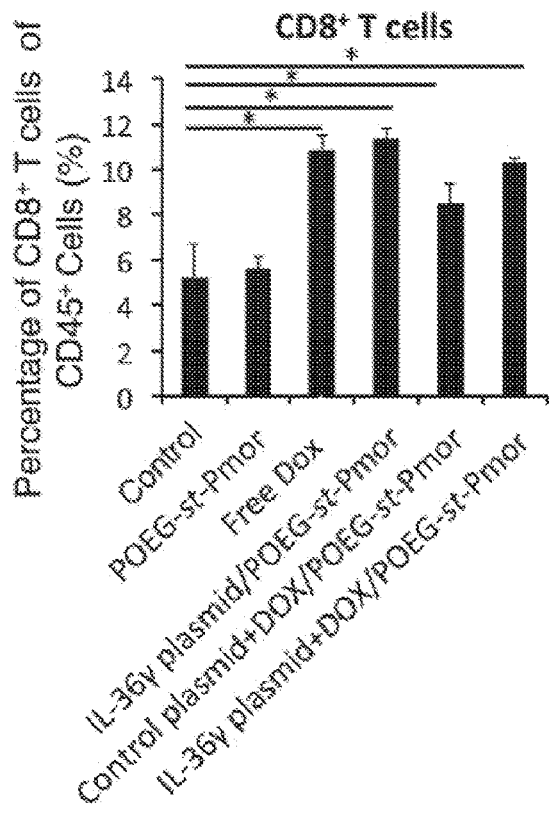
FIG. 10B illustrates a study of cytotoxic $CD8^+$ T cells in lung tissues for treatment with various compositions.
Figure 10C:
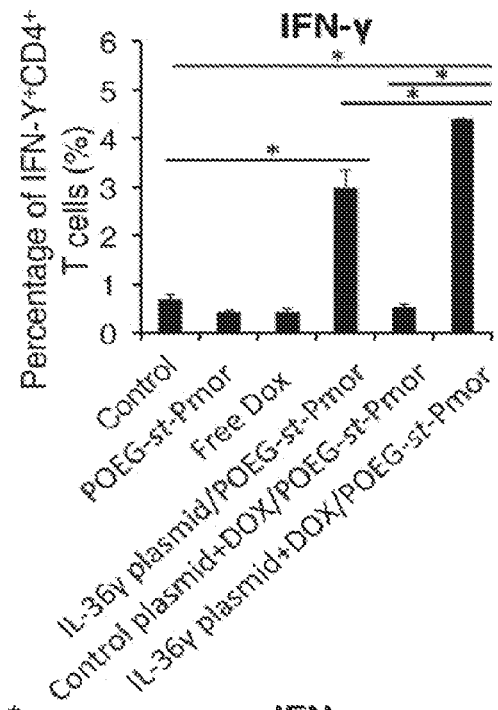
FIG. 10C illustrates a study of the number of $IFN-\gamma^+$ $CD4^+$ for treatment with various compositions.
Figure 10E:
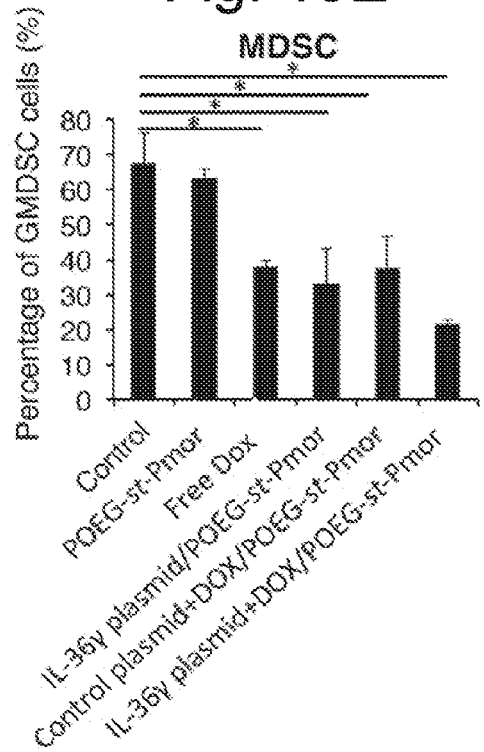
FIG. 10E illustrates a study of the number of MDSCs cells for treatment with various compositions.
Figure 10D:
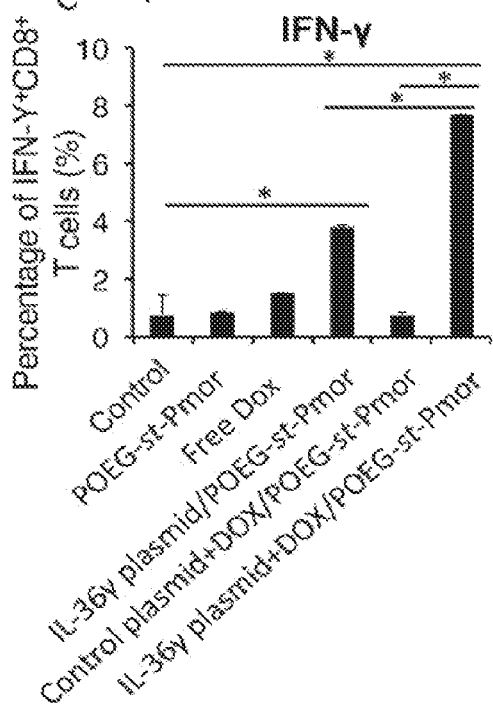
FIG. 10D illustrates a study of the number of $IFN-\gamma^+$ $CD8^+$ T cells for treatment with various compositions.
Figure 10F:
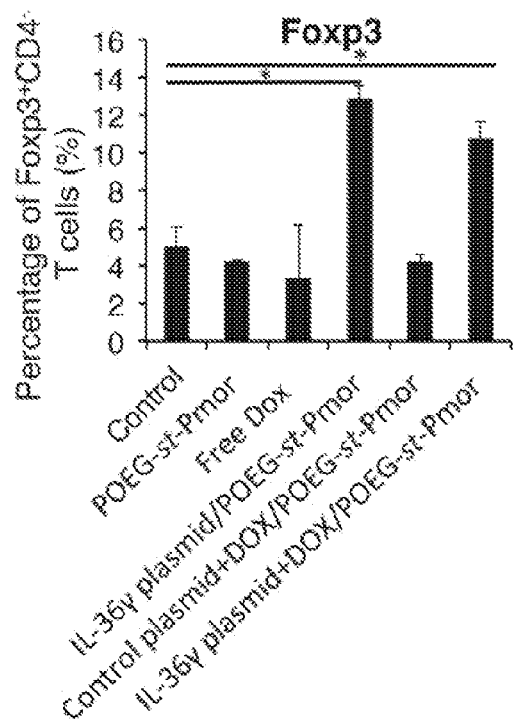
FIG. 10F illustrates a study of the number of $Foxp3^+$ $CD4^+$ T cells (regulatory T cells (Treg)) for treatment with various compositions.

Following demonstration of the significant antitumor activity of DOX+IL-36γ plasmid/POEG-st-Pmor, we examined the immune cell infiltration in the tumor-bearing lungs to elucidate a role of immune response in the overall antitumor activity. As shown in FIGS. 10A and 10B, there was a significant increase of cytotoxic $CD4^+$ T and $CD8^+$ T cells in the lung tissues treated with free DOX, IL-36γ plasmid/POEG-st-Pmor or the combination of both compared to untreated control group. Although there was no significant difference in the total number of T cells between DOX+IL-36γ plasmid/POEG-st-Pmor and DOX+control plasmid/POEG-st-Pmor, the numbers of IFN-γ$^+$ $CD4^+$ and IFN-γ$^+$ $CD8^+$ T cells were significantly increased in the combination treatment group compared to either of the other treatment groups (FIGS. 10C and 10D). We also examined the $CD11^+Gr-1^+$ immunosuppressive myeloid-derived suppressor cells (MDSCs) in lung tissues. The numbers of MDSCs were significantly decreased in all treatment groups except the carrier alone group (FIG. 10E). Surprisingly, there was a significant increase in the number of Foxp3$^+$ $CD4^+$ T cells (regulatory T cells (Treg)) in the mice treated with IL-36γ plasmid, alone or in combination with DOX (FIG. 10F).

DOX is known to induce immunogenic cell death of tumor cells and enhance the recruitment of T cells, which was consistent with flow studies (FIGS. 10A and 10B). On the other hand, IL-36γ is effective in promoting the function of T cells through enhancing the production of IFN-γ as shown in FIGS. 10C and 10D. The synergistic effect between DOX and IL-36γ (s 10C and 10D) may play an important role in the overall antitumor activity.

In another representative embodiment hereof, a co-delivery system (a nanomicellar carrier) for a representative combination of DOX and miR-34a (an oncogenic microRNA or mRNA) was developed which included the natural and endogenous cationic molecule creatine. An important function of creatine is to facilitate recycling of ATP primarily in muscle and brain tissues. It is, for example, widely used by athletes as an ergogenic aid to enhance anaerobic exercise performance. Typically, creatine is produced endogenously or obtained through the diet at a rate of 1 g per day in young adults. Excess amounts of creatine could be metabolized to creatinine and excreted through kidney.

MicroRNAs, sometimes referred to a miRNAs or miRs, are short endogenous non-coding RNAs, responsible for post-transcriptional regulation of many target genes that are involved in cancer cell proliferation and tumor progression. As a result of the imperfect complementarity with target mRNAs, miRs are capable of regulating a broad set of genes simultaneously, which benefits the treatment of cancer as a heterogenic disease. Therefore, there has been growing interest in developing miR-based therapies. In particular, expression level of tumor suppressive miR-34a is usually downregulated in cancerous tissues, which could be reintroduced into cancerous tissues to achieve replacement therapy. Recent studies have revealed that introduction of exogenous miR-34a into cancer cells induced cell apoptosis and inhibited cell proliferation and migration through targeting Bcl-2, CD44, SIRT1, Rac1, Fra-1, Notch-1, and various cyclins. In addition, miR-34a has been reported to sensitize breast cancer cells to first line chemotherapies, including doxorubicin (DOX), paclitaxel, and 5-FU. Moreover, a liposome-formulated miR-34a, namely "MRX34", has entered Phase I clinical trials for the treatment of unresectable primary liver cancer.

A significant limitation for miR-based therapy is that the source of miRs has been limited to synthetic RNAs with artificial modifications, which raises concerns over the stability, cost, specificity and safety of these RNA-based therapeutics. To improve the miR-based therapy, a miR-34a prodrug, pre-miR-34a fused to a transfer RNA (tRNA), namely tRNA-mir-34a has been developed. Wang, W. P. et al. Bioengineering Novel Chimeric microRNA-34a for Prodrug Cancer Therapy: High-Yield Expression and Purification, and Structural and Functional Characterization. *The Journal of pharmacology and experimental therapeutics*

354, 131-141 (2015), the disclosure of which is incorporated herein by reference. These bioengineered miRs are produced and folded in *Escherichia coli* in large scale with high yield, which have been shown to effectively capture the function and safety properties of natural RNAs and therefore represent a new class of more affordable and biocompatible miR-based agents for research and therapy. Indeed, this tRNA-carried pre-miR-34a was selectively processed into mature miR-34a in human carcinoma cells, resulting in reduced expression of the target genes and consequently the inhibition of cancer cell proliferation in vitro and in vivo. The miR-34a prodrug tRNA/miR-34a, which is converted into mature miR-34a upon intracellular delivery, represents an improvement on DOX/miR-34a combination therapy. Currently, miRNA replacement therapy is limited to the use of synthetic RNAs that are chemically modified to improve their stability. Such modifications may alter the folding, biologic activities and, potentially more importantly, the safety profiles (such as the proinflammatory cytokine response). In contrast, the bioengineered miR-34a prodrug is folded in living cells, which may better capture the functions and safety properties of natural miR-34a. However, the application of tRNA-mir-34a alone only exhibited modest effect against human lung cancer or hepatocarcinoma cells. The nanocarrier system hereof provide for a combination of tRNA-mir-34a and small-molecule chemotherapy (for example, DOX) to work synergistically to increase the efficacy of treatment while minimizing the toxicity associated with each treatment alone.

In a number of representative embodiments, a multi-functional delivery system hereof was formed using an amphiphilic polymer (POEG-PCre) with a naturally occurring cationic molecule creatine attached to a pendent side chain. The carrier or delivery system is suitable for the co-delivery of bioengineered a nucleic acid such as tRNA-mir-34a and one or more small molecules such as chemodrugs. Similar to the POEG-st-Pmor polymer describe above, the backbone, the POEG-PCre polymer (POEG-PVBC) includes hydrophobic alkyl main chain and pendent benzyl rings and forms the core of micelles to load hydrophobic molecules such as anticancer drugs through hydrophobic-hydrophobic interaction and π-π stacking. Creatine was post-conjugated to the backbone to introduce positive charges to form complexes with the negatively charged nucleic acids. In addition, the cationic creatine groups in the polymer can also facilitate accumulation of the nanoparticles in, for example, the lung and the subsequent interaction with target cells. The lung is the first capillary bed encountered by cationic NPs after intravenous (i.v.) injection and may be the most effective target organ. It also has been reported that lung tissue is endowed with a much higher polyamine active uptake system than any other major organs, which may benefit the targeted delivery of the creatine-based carrier systems hereof with amine groups to the lungs. The excess amount of positive charges on the nanocarrier was shielded by PEG to improve in vivo stability. The co-delivery of, for example, tRNA-mir-34a and DOX via the multi-functional nanocarriers hereof may provide a safe and effective approach for the treatment of, for example, metastatic TNBC. The biodegradability of the polymer and the non-toxic nature of creatine may provide for an excellent safety profile of the nanocarrier system as further discussed below. The biophysical properties of the nanocarrier co-loaded with DOX and tRNA-mir-34a were studied. The efficiency of delivery and transfection was also examined both in vitro and in vivo. Further, the antitumor effect of DOX+tRNA-mir-34a/polymer as well as the underlying mechanism was investigated.

Figure 11:
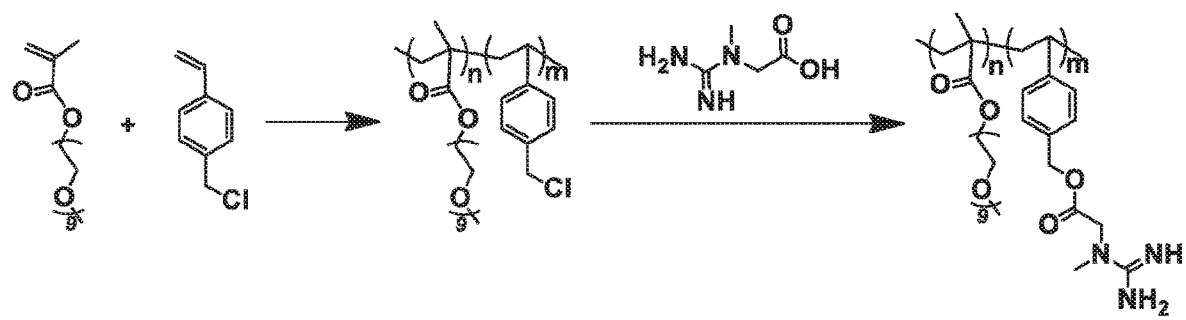
FIG. 11 illustrates an embodiment of synthesis of a POEG-PCre polymer hereof by RAFT co-polymerization of OEG500 monomer and VBC monomer, followed by conjugation with creatine.

The POEG-PCre polymer was synthesized by RAFT co-polymerization of OEG500 monomer and VBC monomer, followed by conjugation with creatine as illustrated in FIG. 11. The structure of the POEG-PVBC and POEG-PCre were characterized via $^1$H nuclear magnetic resonance (NMR) spectra. The units of OEG and VBC were calculated to be 25 and 118, respectively, according to the monomer conversion. The conjugated units of creatine were calculated to be 47 by comparing the characteristic signals at 4.12-4.8, 5.07, and 5.95-7.88 ppm.

Figure 12A:
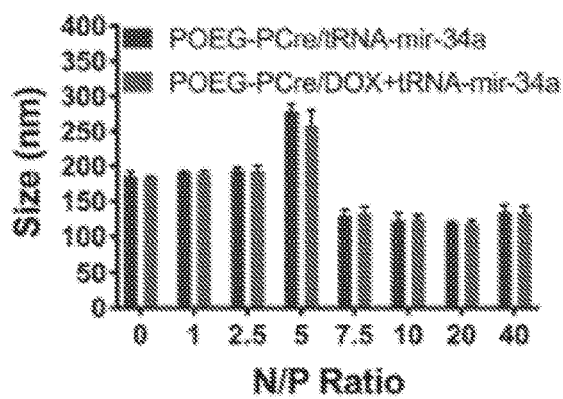
FIG. 12A illustrates a study of the size of POEG-PCre micelles hereof as a function of N/P ratio.

POEG-PCre micelles were prepared by dialysis. The POEG-PCre copolymer self-assembled into spherical nanoparticles with a size around 180 nm as indicated by DLS and TEM (FIG. 12A). The CMC of POEG-PCre copolymer, determined using nile red as a fluorescence probe, was as low as approximately 0.05 mg/mL. The low CMC indicated the stability of POEG-PCre micelles upon dilution in the blood stream after i.v. injection. The DOX-loaded POEG-PCre micelles were similarly prepared. DOX could be incorporated into POEG-PCre micelles at a carrier/drug mass ratio of 5:1 or higher. A carrier/drug ratio of 10:1 was chosen for the subsequent studies because of the relatively high drug loading capacity and the excellent colloidal stability (stable for one month and two months at RT and 4° C., respectively). DOX-loaded POEG-PCre micelles were comparable to blank POEG-PCre micelles in size and morphology.

Figure 12B:
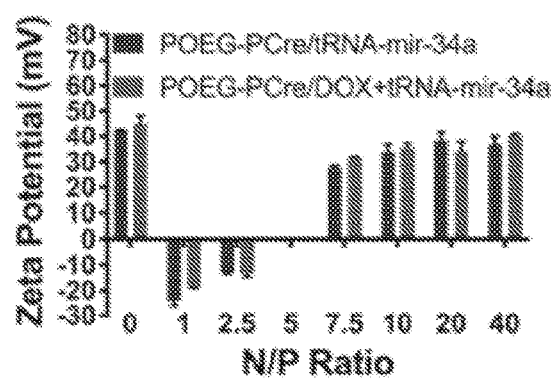
FIG. 12B illustrates a study of the surface zeta potential of POEG-PCre micelles hereof as s function of N/P ratio.

The surface zeta potential of POEG-PCre micelles was approximately +40 mV (FIG. 12B). Whether the cationic micelles could form stable complexes with tRNA-mir-34a was tested via gel retardation assay. POEG-PCre micelles were mixed with tRNA-mir-34a at various N/P ratios from 1:1 to 40:1. Complete complexation of tRNA-mir-34a by POEG-PCre polymer was achieved at an N/P ratio of 5:1 or greater. Accordingly, at N/P ratios of below 5, the net charges of nanocomplexes were negative with the particle sizes similar to that of blank micelles. At an N/P ratio of 5, a significant increase in particle size was observed with particle charges close to neutral. Further increases in N/P ratios led to continuous increases in zeta potentials and decreases in particle sizes, suggesting gradual condensation of nucleic acid by POEG-PCre cationic polymer. To form more compact POEG-PCre/tRNA-mir-34a complexes as well as to overcome the neutralization by serum proteins, an N/P ratio of 20 was chosen for all subsequent studies. At this N/P ratio, the average size of the nanocomplexes decreased to around 120 nm. In addition, DOX loading had negligible effect on the size distribution, zeta-potential and nucleic acid binding ability of POEG-PCre micelles. In a number of embodiments of formulations hereof, the N/P ratio may, for example, be 1:1 to 100:1, 1:1 to 40:1, or 5:1 to 20:1. Suitable ranges of N/P ratio are readily determined for particular compositions hereof using the methods described herein.

The binding ability of POEG-PCre to plasmid or siRNA was also investigated. Compared to complexation with tRNA-mir-34a, POEG-PCre polymer could form stable complexes with plasmid at a lower N/P ratio of 2.5:1. However, POEG-PCre polymer was not effective in complexing with siRNA at an N/P ratio as high as 80:1, suggesting that the POEG-PCre carrier was unique in forming complexes with nucleic acids with appropriate sizes and secondary structures including tRNA-mirs. In a number of embodiments of formulation based on POEG-PCRE, the nucleic acid may, for example, include approximately 19 to 20,000 base pairs for double stranded molecules or 19 or more base pairs for single stranded molecules. However, one may readily adjust the polymer composition hereof to interact via charge-charge interactions with negatively charged nucleic acids of virtually any size/composition. Ranges of sizes of single or double stranded nucleic acids for use in forming formulations hereof are readily determined using the methods described herein for any polymer composition hereof. To further investigate the interaction between POEG-PCre nanocarrier and tRNA-mirs, a competitive binding gel-shift assay with dextran sulfate was performed. At an N/P ratio of 5:1, substantial amounts of tRNA-mir-34a began to be released from POEG-PCre nanocarrier or PEI at an S/P ratio (molar ratio between the sulfur from dextran sulfate and the phosphate from tRNA-mir-34a) of 5 or greater. When the N/P ratio reached 10:1 or higher, tRNA-mir-34a could not be replaced by dextran sulfate even at an S/P ratio as high as 80. In contrast, an obvious release of tRNA-mir-34a was observed from PEI carrier at the corresponding N/P ratios. These data suggest that, in addition to electrostatic interaction as seen with PEI, other mechanisms of interactions, such as π-π stacking between the pendent benzyl rings of our polymer and the base π-systems of nucleic acids, might be conductive to a more stable nanocomplexing system.

Figure 12C:
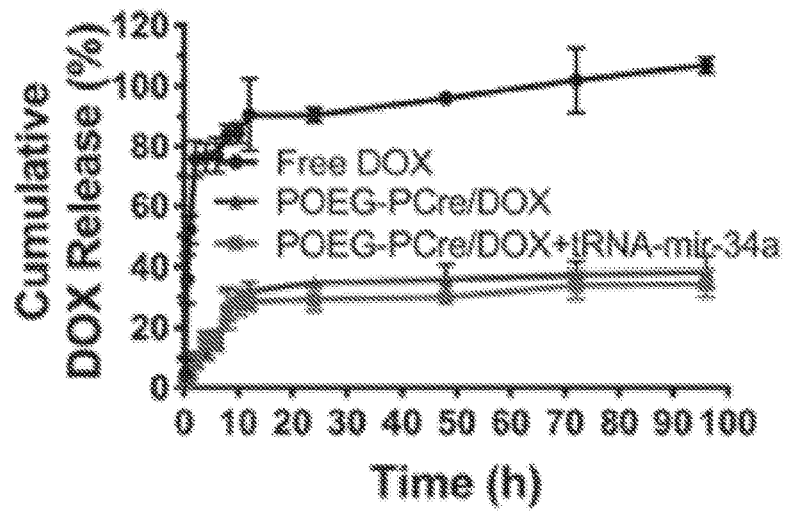
FIG. 12C illustrates a study of cumulative DOX release from micelles hereof as a function of time.

The release kinetics of DOX from DOX-loaded POEG-PCre micelles was investigated by dialysis against DPBS of pH 7.4 at 37° C. As shown in FIG. 12C, more than 80% of free DOX was diffused out of dialysis bag (MWCO=3500) in the first 4 h. To the contrary, only 16% of DOX was released from DOX/POEG-PCre micelles in first 4 h, and less than 40% of DOX was released for an extended period of 96 h. POEG-PCre micelles co-loaded with DOX and tRNA-mir-34a exhibited a comparable but slightly slower release profile compared with micelles loaded with DOX alone.

Figure 12D:
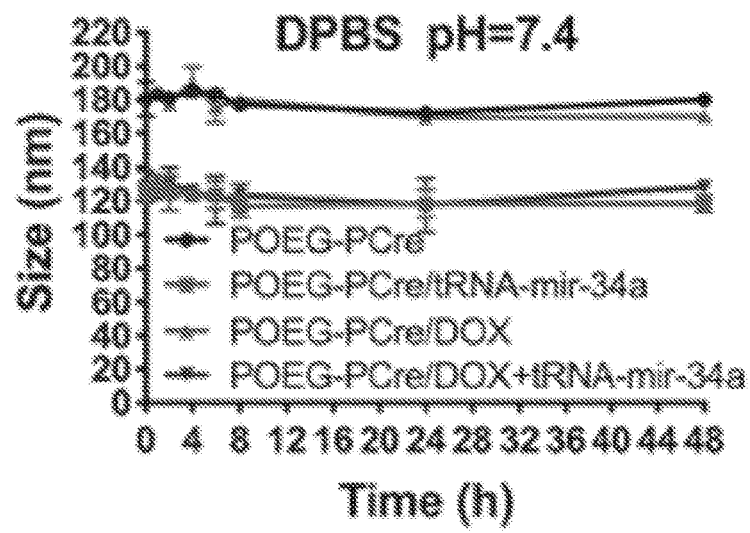
FIG. 12D illustrates a study of micelle size over time in DPBS solution, demonstrating little aggregation.
Figure 12E:
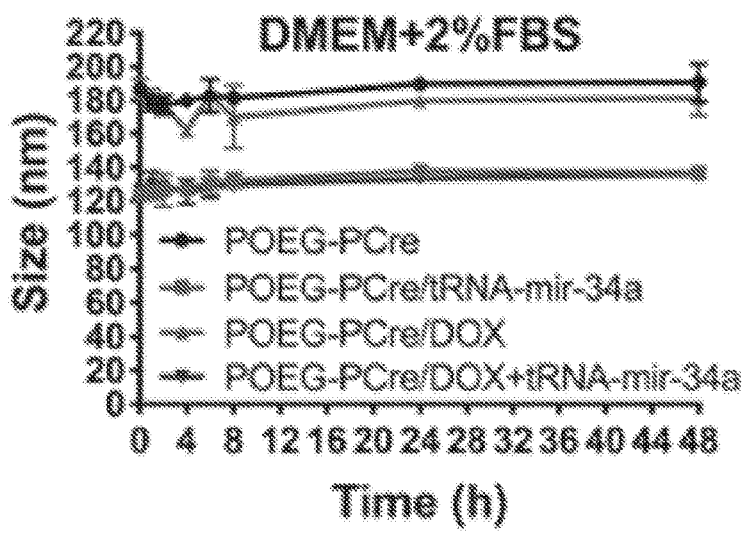
FIG. 12E illustrates a study of micelle size over time in DMEM solution, demonstrating little aggregation.
Figure 12F:
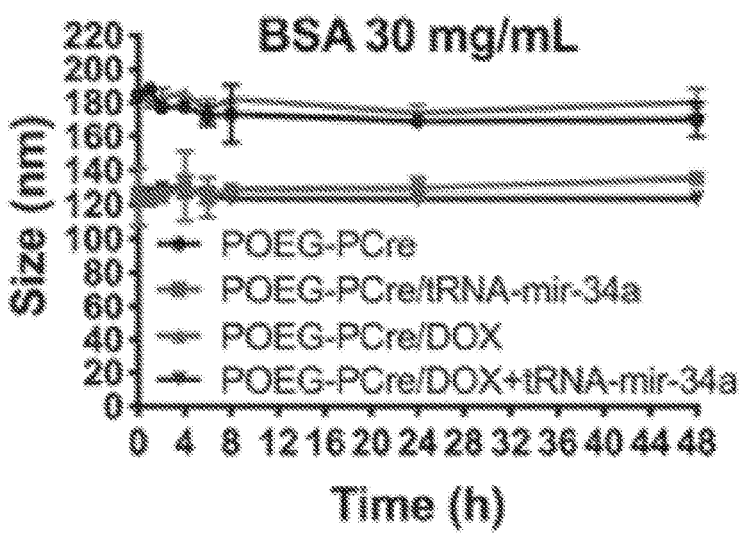
FIG. 12F illustrates a study of micelle size over time in BSA solution, demonstrating little aggregation.

The stability of the nanocomplexes was studied in various solutions that mimic commonly used buffer, routine cell culture medium or serum, respectively, such as DPBS of pH 7.4, DMEM medium with 10% FBS or 30 mg/mL of BSA. As shown in FIG. 12D through 12F, no aggregation of nanoparticles was observed in all tested solutions and all of the nanocomplexes showed minimal changes in sizes for up to 48 h.

To monitor intracellular co-delivery of DOX and tRNA-mir-34a, tRNA-mir-34a was labeled with MFP488 fluorescent dye to visualize the cell uptake of tRNA-mir-34a along with red fluorescence of DOX. 4T1.2 cells were incubated for 4 h with micelle complexes carrying DOX and/or MFP488-labeled tRNA-mir-34a and then observed under a confocal microscope. Naked tRNA-mir-34a without any transfection agent was used as a negative control. DOX/POEG-PCre showed more DOX fluorescence signal compared to free DOX at the same dose of DOX. The DOX+tRNA-mir-34a$^{MFP488}$ co-loaded POEG-PCre micelles showed even more uptake of DOX than that of the DOX/POEG-PCre micelles, which may, for example, be a result of a more condensed structure following complexation with tRNA-mir-34a and, therefore, higher endocytosis efficiency. Overlay of DOX (red) and tRNA-mir-34a$^{MFP488}$ (green) generated the yellow signals in the merged channel, suggesting the co-localization of DOX and tRNA-mir-34a$^{MFP488}$ inside tumor cells. In addition, fluorescence signals of both DOX and tRNA-mir-34a$^{MFP488}$ were present in the perinuclear regions of the cytoplasm in nanocomplexes treated groups, while the DOX fluorescence signals in free DOX treated group were largely found in the nucleus overlapping with Hoechst staining (blue). These data suggest the different cellular uptake routes of free DOX and DOX-loaded micelles, through passive diffusion and endocytosis, respectively.

The processing of tRNA-mir-34a into mature tumor suppressor miR-34a was evaluated by quantitative RT-PCR. As shown in FIG. 13A, there was over a 200-fold increase in the amount of mature miR-34a in 4T1.2 cells following treatment with tRNA-mir-34a/POEG-PCre nanocomplexes. Significantly greater amounts of mature miR-34a (~1200-fold increase) were found in cells treated with the DOX+tRNA-mir-34a co-loaded POEG-PCre micelles. This is not likely a result of the differences in the amounts of tRNA-mir-34a delivered intracellularly as comparable levels of MFP488 fluorescence were found for the two groups. Consistently, FIG. 13B shows that the amounts of chimeric ncRNA scaffold inside 4T1.2 cells were similar after treatment with either POEG-PCre/tRNA-mir or POEG-PCre/DOX+tRNA-mir, suggesting comparable efficiency of delivery of the two formulations. It might, however, be a result of a more efficient processing of tRNA-mir-34a in cells following co-delivery of DOX. Treatment with free DOX or DOX-loaded POEG-PCre micelles led to the induction of Dicer, an RNase III enzyme involved in pre-miRs cleavage, in a dose dependent manner. As a result, the level of pre-miR-34a in DOX+tRNA-mir-34a/POEG-PCre-treated cells was significantly lower than that in cells treated with tRNA-mir-34a/POEG-PCre, suggesting a more complete processing of pre-miR-34a into mature miR-34a as a result of the co-delivered DOX (FIG. 13C). Similar trends were observed in MDA-MB-231 cells (FIGS. 13A through C).

The expression of Bcl-2 was then evaluated at both the transcript and protein levels after intracellular delivery of tRNA-mir-34a. tRNA-MSA (Sephadex aptamer tagged methionyl-tRNA), the sole tRNA scaffold, was used as a control. As shown in FIG. 13D, the mRNA expression levels of Bcl-2 in cells treated with blank POEG-PCre micelles, tRNA-MSA/POEG-PCre micelles, free DOX, DOX/POEG-PCre micelles or DOX+tRNA-MSA/POEG-PCre micelles were similar to that of untreated control cells, indicating that POEG-PCre carrier, tRNA-MSA as well as DOX had minimal regulatory effects on the expression of Bcl-2. In contrast, significant down-regulation of Bcl-2 expression was observed in the tumor cells treated with POEG-PCre/tRNA-mir-34a or the co-loaded formulation. Consistently, the downregulation of Bcl-2 was also confirmed at the protein level by Western blotting. Down-regulation of Bcl-2 was more dramatic in cells treated with the co-loaded formulation compared to cells treated with POEG-PCre/tRNA-mir-34a. Similar results were found in MDA-MB-231 cells.

Figure 14A:
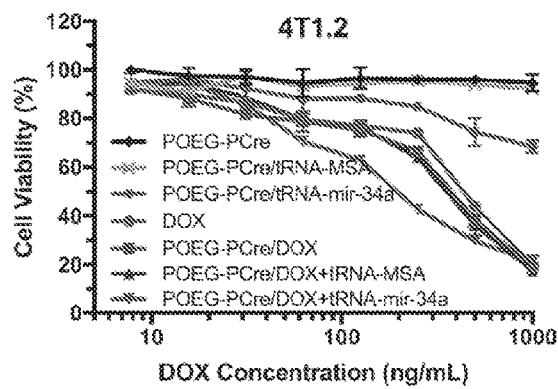
FIG. 14A illustrates a study of cell growth inhibition for 4T1.2 cells after treatment with various formulations.
Figure 14B:
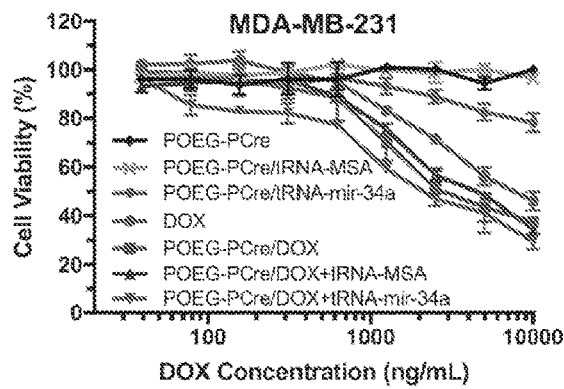
FIG. 14B illustrates a study of cell viability of MDA-MB-231 cells after treatment with various formulations.

The in vitro cytotoxicity of DOX+tRNA-mir-34a co-loaded POEG-PCre micelles was evaluated by MTT assay. Tumor cells were treated with various formulations for 48 h, with the doses of DOX, tRNA-mir, and POEG-PCre carrier ranging from 7.8 to 1,000 ng/mL, 0.78 nM to 100 nM, and 78 ng/mL to 10000 ng/mL, respectively. As shown in FIGS. 14A and 14B, no obvious cell growth inhibition was noticed in cells treated with POEG-PCre nanocarrier alone or tRNA-MSA loaded POEG-PCre micelles, even when the concentration of the polymer reached 10 μg/mL. tRNA-mir-34a/POEG-PCre micelles showed a moderate level of cytotoxicity at high concentrations. Free DOX inhibited the proliferation of tumor cells in a dose dependent manner and the cytotoxicity of DOX/POEG-PCre was comparable to that of free DOX. Incorporation of tRNA-MSA into DOX/POEG-PCre micelles showed minimal impact on the overall cytotoxicity of the co-loaded formulation. In contrast, incorporation of tRNA-mir-34a into DOX loaded POEG-PCre micelles led to a significant improvement in the cytotoxicity of nanocomplexes on 4T1.2 cells, indicating the synergistic effect between co-delivered tRNA-mir-34a and DOX via our POEG-PCre system (FIG. 14A). A similar trend was also observed in MDA-MB-231 breast cancer cells (FIG. 14B).

The enhanced cytotoxicity of DOX+tRNA-mir-34a-co-loaded nanocomplexes was assessed via apoptosis assay. Cell apoptosis was evaluated quantitatively by Annexin V/propidium iodide flow cytometry. Few apoptotic cells were detected in control cells or cells treated with POEG-PCre carrier alone or tRNA-MSA loaded nanocomplexes, which was consistent with MTT assay. An increase in cell apoptosis (~21%) was observed in cells treated with tRNA-mir-34a loaded nanoparticles, suggesting that increased expression of mature miR-34a after delivery of tRNA-mir-34a into tumor cells can trigger the apoptosis of breast cancer cells, which are consistent with the tumor suppressor functions of miR-34a. Free DOX, DOX/POEG-PCre and DOX+tRNA-MSA POEG-PCre were comparable in inducing cell apoptosis to a significantly higher level (~31%), which was consistent with previous reports that DOX kills cancer cells through triggering cell apoptosis. Importantly, a significantly higher percentage of necrosis (~13%), in addition to much greater degree of late apoptosis (~20%) and comparable level of early apoptosis was obtained in cells treated with DOX+tRNA-mir-34a co-loaded formulation, again suggesting a potent synergy between tRNA-mir-34a and DOX in inducing apoptosis and necrosis.

Besides cancer cell viability, cell migration represents a critical process for tumor progression and metastasis. MiR-34a has been reported to be functional as an anti-metastatic miRNA by directly targeting CD44 and NOTCH-1. Therefore, the effect of tRNA-mir-34a and DOX co-loaded nanocomplexes on the cell migration was investigated using the wound closure assay. The wounded area was substantially repopulated by highly aggressive 4T1.2 cancer cells after 24 h in groups with no treatment or when treated with POEG-PCre nanocarrier alone or tRNA-MSA loaded nanocomplexes. Significant inhibition (~75%) of cell migration was observed in cells treated with tRNA-mir-34a/POEG-PCre. The three DOX-containing formulations (free DOX, DOX/POEG-PCre or DOX+tRNA-MSA/POEG-PCre) were comparable in potency with a modest inhibition of ~40%. In contrast, the DOX/tRNA-mir-34a-co-loaded group was most effective in inhibiting the migration of cancer cells; the denuded area was well retained with only 4.9% of repopulated cells.

To gain insight into the biodistribution of nanocomplexes, the fluorescence signals of DOX and MFP488-labeled tRNA-mir-34a in tissue sections were examined by confocal microscopy. Substantial amounts of fluorescent signals of both DOX and MFP488 were detected in lungs treated with DOX+tRNA-mir-34a$^{MFP488}$ co-loaded micelles. The yellow color in the merged channel indicated the co-localization of DOX and tRNA-mir-34a in lung tissues. Compared to the lungs, substantially lower levels of fluorescent signals were observed in other major organs, suggesting that POEG-PCre nanocarrier is particularly suitable for targeted co-delivery of DOX and tRNA-mir-34a to lungs, which may benefit the prevention and treatment of breast cancer lung metastasis.

Figure 15A:
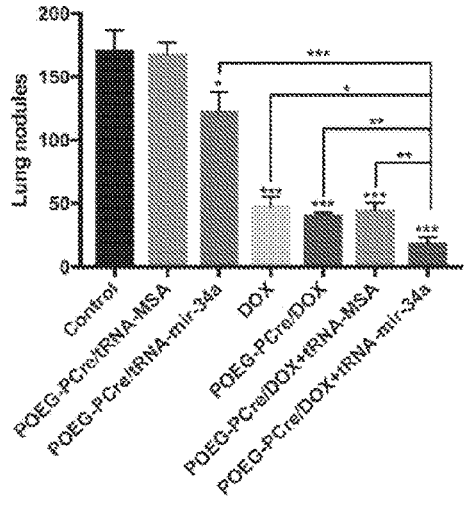
FIG. 15A illustrates a study of the number of lung nodules after treatment with various formulations.
Figure 15B:
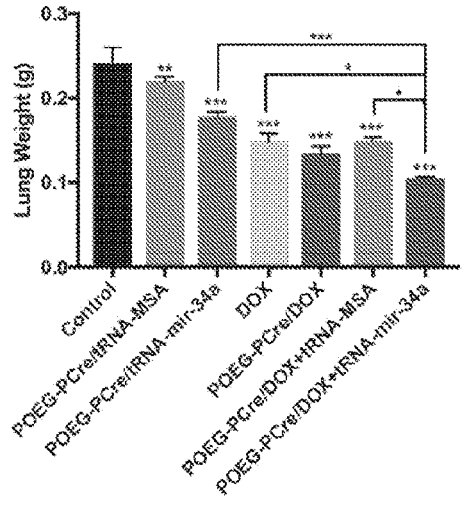
FIG. 15B illustrates a study of lung weight after treatment with various formulations.
Figure 15C:
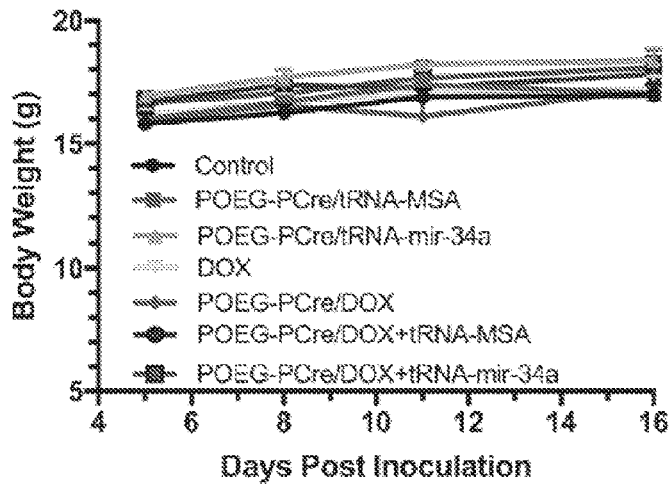
FIG. 15C illustrates a study of body weight as a function of time of treatment with various formulations.

The in vivo anti-tumor efficacy of DOX+tRNA-mir-34a co-loaded nanocomplexes was evaluated in a breast cancer lung metastasis model, generated by tail-vein injection of 4T1.2 tumor cells into female Balb/c mice. Five days after tumor inoculation, various treatments were applied to each group of mice (n=5) via i.v. administration every 3 d for 3 times. The tumor burdens in the lungs were analyzed 5 days after the last treatment. As shown in FIGS. 15A and 15B, tRNA-MSA loaded in POEG-PCre micelles showed negligible therapeutic effect compared to the control group. However, tRNA-mir-34a/POEG-PCre nanocomplexes exhibited a moderate inhibition of lung metastasis (P<0.05). Dramatic reduction in the number of tumor nodules in lungs was found in groups treated with free DOX, DOX/POEG-PCre or DOX+tRNA-MSA/POEG-PCre micelles. More importantly, POEG-PCre micelles co-loaded with DOX and tRNA-mir-34a was significantly superior to all other treatments in the inhibition of 4T1.2 tumor metastasis. No significant decrease of body weight was observed, indicating the safety of the formulation (FIG. 15C).

FIG. 15D shows that the levels of mature miR-34a were significantly and selectively unregulated in tumors treated with tRNA-mir-34a loaded micelles. Consistent with in vitro data, codelivery of tRNA-mir-34a and DOX via POEG-PCre micelles led to a further increase in the amounts of mature miR-34a which may be a result of the upregulation of Dicer expression by DOX-containing formulations in vivo. FIGS. 15E and 15F illustrate that the expression levels of Bcl-2 in tumor tissues were significantly suppressed at both mRNA and protein levels following treatment with tRNA-mir-34a, particularly the co-loaded formulation. To further confirm the anticancer efficacy, H&E staining and immunohistochemical analysis of Ki67 were performed in tumor-bearing lungs. Staining of lung tissues showed clearly infiltration of tumor cells (with large nuclei) in all of the groups except the DOX/tRNA-mir-34a co-delivery group. In addition, DOX/tRNA-mir-34a co-delivery group showed the lowest number of Ki67-positive tumor cells. Together, the above data clearly suggest a synergy between DOX and tRNA-mir-34a in the overall antitumor activity in the lung metastasis model.

Compared to control or monotherapy, co-delivery of DOX and tRNA-mir-34a did not cause loss of body weight (FIG. 15C) or any other signs of stress such as hunched posture and labored movement. In addition, blood chemistry tests were performed to evaluate the effect of our formulations on liver and kidney functions. None of the measured blood biomarkers including alanine aminotransferase (ALT), aspartate aminotransferase (AST) and creatinine were significantly altered by our therapies, indicating the absence of hepatic and renal toxicity. Moreover, the H & E staining of major organs was carried out to further evaluate the potential toxicity of different treatments. Further, there were signs of myocytolysis and myofibrillolysis with fibrils dearrangement in the heart sections in free DOX group. In addition, hepatocellular vacuolation was found in this group, suggesting possible cardiac and liver toxicities despite no significant alterations in ALT and AST levels. In contrast, no significant pathological changes were observed in the major organs in the groups treated with single-loaded or co-loaded nanocomplexes. These results suggested that POEG-PCre based formulations were well tolerated at the doses tested.

FIGS. 16A and 16B show that DOX treatment led to a significant increase in the numbers of CD4 and CD8 cells in the tumor-bearing lungs. DOX treatment also led to a trend of increase in the numbers of functional CD8 (IFN-γ+ CD8) cells (FIG. 16C). However, the above changes were much more dramatic following the tRNA-mir-34a/DOX combination treatment (FIGS. 16A-C). Treatment with tRNA-mir-34a alone or tRNA-mir-34a/DOX combination reduced the numbers of PD1+ CD8 cells (FIG. 16D) and T-regulatory cells (Tregs) (FIG. 16E). FIG. 16F shows that the numbers of MDSC were significantly decreased following the tRNAmir-34a/DOX combination treatment. There was a trend of decreases in the numbers of MDSC following the treatment with DOX alone.

The studies hereof thus show that POEG-PCre represents a simple nanocarrier for effective co-loading of small molecule drugs and nucleic acids-based therapeutics. POEG-PCre readily self-assembles to form a hydrophobic core that allows effective loading of hydrophobic drugs such as DOX. At the same time, the multiple positive charges from creatine at the interface of the POEG-PCre micelles facilitate the interaction with the negatively charged nucleic acids. As described above, the multivalent charge-charge interactions between the cationic polymer and nucleic acids may also serve as a simple approach to "cross-link" and stabilize the micelles. As a result, the size of tRNA-mir-34a complexed micelles (~120 nm) was much smaller than that of blank micelles or DOX-loaded micelles (~180 nm). In addition, DOX/tRNA-mir-34a-coloaded nanoparticles exhibited a slightly slower release kinetics compared to that of micelles loaded with DOX only.

Complexation of cationic polymers with large-sized nucleic acids such as plasmid DNA is known to lead to formation of compact particles, which involves structure arrangement and condensation of nucleic acids. On the other hand, cationic polymers tend to form loose complexes with short oligonucleotides as a result of their small lengths. Accordingly, the POEG-PCre polymers hereof readily formed stable complexes with plasmid DNA at N/P ratios above 2.5 but failed to do so with short siRNA at N/P ratio as high as 80. In a number of embodiments, nucleic acids with 100 or more nucleotides (nt) are used. Interestingly, tRNA-mir-34a appears to have an appropriate size (~200 nt) to form stable complexes with POEG-PCre polymer. The POEG-PCre/tRNA-mir-34a complexes were more stable than PEI/tRNA-mir-34a complexes as evidenced by the fact that tRNA-mir-34a in POEG-PCre/tRNA-mir-34a complexes was more resistant to the replacement by the negatively charged dextran sulphate compared to PEI/tRNA-mir-34a. This observation may be a result of additional mechanisms of interactions between POEG-PCre and nucleic acids in addition to charge interactions. Similar to other polymers hereof, the backbone of POEG-PCre includes hydrophobic alkyl main chains and pendent benzyl rings that can interact with the base π-systems of nucleic acids through hydrophobic interaction and π-π stacking. The enhanced interaction of the polymers hereof with nucleic acids may help to improve the stability of polymer/nucleic acid complexes in the blood circulation.

POEG-PCre was highly effective in mediating codelivery of the representative combination of tRNA-mir-34a and DOX to cultured tumor cells in vitro and pulmonary circulation in vivo. Creatine is a derivative of the guanidinium cation. Positively charged guanidinium groups are able to form electrostatic association and bidentate hydrogen bond with anionic cell surface phosphates, carboxylates and/or sulfates to initiate the event of cellular entry. This feature has been widely utilized to design several new guanidinium-rich transporter scaffolds to improve the performance of cell penetration for small molecules, peptides and genes. The efficient intracellular delivery of tRNA-mir-34a and DOX may benefit from this multivalent effect. Following systemic administration, the creatine-based polymer may take advantage of the lung-enriched polyamine transporters to guide the targeted accumulation of nanocomplexes to lung tissues. Indeed, a more predominant distribution of the nanocomplexes in the lungs was observed as described above, which should be beneficial for the prevention and treatment of lung metastasis.

Codelivery of DOX and tRNA-mir-34a via POEG-PCre-based nanoparticles led to an enhanced combinational effect both in vitro and in vivo. Codelivery of DOX facilitates the processing of tRNA-mir-34a, resulting in increased levels of mature miR-34a ($P<0.001$). The underlying mechanism is not clearly understood. However, the data suggest that DOX induced the expression of RNase III enzyme Dicer. It has been reported that Dicer is required for activating the DNA damage response when double-strand DNA breaks and non-coding RNA is synthesized at the site of DNA damage. Therefore, DOX may enhance the expression of Dicer through the DNA damage response.

Without limitation to any mechanism, the improved antitumor activity of DOX/tRNA-mir-34a-based therapy is likely attributed to various factors. Overexpression of miR-34a is effective in inhibiting the proliferation of cancer cells and inducing apoptosis. In addition, miR-34a sensitizes cancer cells to chemotherapeutic agents such as DOX. The data further suggest a role of immune response in the overall antitumor activity of DOX/tRNA-mir-34a combination therapy. DOX was reported to trigger immunogenic cell death by promoting tumor infiltration of IL-17-secreting γδ T cells and enhancing the proliferation and activation of IFNγ-secreting CD8+ T cells in tumor draining lymph nodes. Similar results were shown in our studies with a lung metastatic tumor model. However, treatment with DOX+tRNA-mir-34a co-loaded nanocomplexes resulted in even greater numbers of tumor-infiltrating CD4+, CD8+ and CD8+ IFN-$\gamma^+$ CD8$^+$ T cells, which may be attributed to the effect of miR-34a on the down-regulation of PD-L1 expression. In addition, the co-treatment led to significantly reduced numbers of MDSCs that are highly immunosuppressive and play an important role in suppressing the antitumor immunity. The combination therapy enabled by the nanocarriers hereof thus helps to create an active tumor immune microenvironment that likely contributes to the overall antitumor activity.

In another representative example, PMet-P(cdmPEG$_{2K}$) polymeric micelles based on polymetformin (PMet) with an intratumor, pH-responsive PEG deshielding functionality was developed for co-loading and tumor-targeted co-delivery of a small molecule therapeutic agent (for example, DOX) and a nucleic-acid-base therapeutic (for example, plasmid encoding interleukin 12 or IL-12 cytokine gene) for a combined chemoimmunotherapy. The positive charge shielding performance of PEG on the PMet-P(cdmPEG$_{2K}$) micellar surface enhanced the serum stability of micelles and micelleplexes after intravenous injection. IL-12/DOX co-loaded micelleplexes exhibited enhanced cell proliferation inhibition effects than DOX-loaded micelles, and displayed a higher cytotoxicity at acidic extracellular microenvironment of tumor (pH 6.8). The PMet-P(cdmPEG$_{2K}$) micelles showed the significantly improved EGFP/luciferase reporter plasmid expression and Cy3-siRNA transfection efficiency, and DOX intracellular uptake in 4T1.2 cells at pH 6.8. Moreover, PMet-P(cdmPEG$_{2K}$) micelles showed excellent EGFP pDNA transfection in an aggressive murine breast cancer (4T1.2) model, which suggested potent in vivo gene delivery for targeted tumor therapy application. PMet-P(cdmPEG$_{2K}$) micelles co-loaded with DOX and IL-12 cytokine gene was more efficient in tumor growth inhibition, compared to DOX loaded micelles and IL-12 gene loaded micelleplexes. This intratumor pH-responsive deshielding micellar system exhibited significant potential for effective combination of immunotherapy based on plasmid encoding IL-12 cytokine gene and traditional DOX chemotherapy.

As described above, cytokine-based therapy has been emerging as a promising strategy for various cancer therapies because of the direct anti-proliferative activity against cancer cells or indirect anti-tumor activity by stimulating the immune system. Among various cytokines, IL-12 is considered to be promising immunostimulatory cytokine with potent anti-tumor activity. It can activate cytotoxic T lymphocytes, natural killer (NK) cells and induce the secretion of IFN-γ. Although recombinant IL-12 protein has demonstrated effective therapeutic effect against several tumor models, severe adverse effects after systemic administration limit its application. As an alternative approach, IL-12 based gene therapy has been reported to cause lower side effects through localized expression of IL-12 protein in tumor cells compared to recombinant IL 12 protein therapy. Unfortunately, only moderate antitumor efficacy has been achieved.

The combination strategy of IL-12 based gene therapy with standard cytotoxic chemotherapy holds considerable promise to further improve the therapeutic efficacy. As described above, DOX is a first-line chemotherapeutic agent which has been widely utilized for the treatment of a variety of malignant tumor. In addition, it has been reported that DOX can induce immunogenic cell death and activate antitumor T cell immune responses, leading to synergistic antitumor effect when combined with immunostimulatory agents, including IL-12. However, similar to other small molecule therapeutic/nucleic-acid-base therapeutic combinations, the simultaneous and efficient delivery of DOX and IL-12 gene in vivo is particularly challenging as a result of the differences in physicochemical properties of these two types of agents. Therefore, a drug delivery system capable of co-delivering DOX and IL-12 gene simultaneously with high efficiency for cancer therapy is very desirable.

PEGylation of cationic polymeric micelles is an effective way to sterically stabilize micelles and minimize the non-specific interaction in vivo, thereby prolonging the circulation time and facilitating tumoral accumulation via enhanced permeation and retention (EPR) effects. However, PEGylation may significantly reduce their cellular uptake in tumor tissues, significantly limiting gene transfection and drug delivery efficiency in vivo. PEG shielding/deshielding strategies may be used PEGylated polymers for delivery of genes or drugs. Carboxydimethyl maleate (cdm) is an acid-labile linker which can be cleaved at the acidic tumor extracellular pH (pH=6.5-6.8). Based on the differences in pH between normal tissues (pH=7.4) and tumor tissues (pH=6.5-7.2), conjugation of the cationic polymers with PEG chains via cdm linker is an efficient strategy to construct pH-responsive PEG deshielding carriers for improved cell internalization and targeted gene/drug delivery in tumor tissues.

Metformin (Met, dimethybiguanide)-based and cdm-linked cationic micelles PMet-P(cdmPEG$_{2K}$) with PEG deshielding characteristics was developed for co-loading and tumor-targeted co-delivery of, for example, DOX and a nucleic acid (plasmid encoding IL-12 gene). Metformin is a commonly used antidiabetic drug for type II diabetes treatment. Increasing evidence has also demonstrated that Met shows potent antitumor efficacy against various types of cancers, which may be attributable to the activation of adenosine monophosphate-activated protein kinase (AMPK) and inhibition of the mammalian target of rapamycin (mTOR) [23-26]. Moreover, the biguanide group of Met can be used as an ideal cationic motif for constructing gene delivery carriers. PMet-P(cdmPEG$_{2K}$) polymers can self-assemble into micelles under aqueous conditions for DOX encapsulation. The resultant DOX-loaded PMet-P(cdmPEG$_{2K}$) micelles further complex with IL-12 pDNA through electrostatic interaction. After intravenous injection, IL-12/DOX PMet-P(cdmPEG$_{2K}$) micelleplexes may prolong circulation in the blood via the PEG shielding and accumulate preferentially in tumor tissue by enhanced permeability and retention (EPR) effect. Once reaching the tumor extracellular acidic pH environment (pH 6.8), IL-12/DOX co-loaded PMet-P(cdmPEG$_{2K}$) micelleplexes may undergo acid hydrolysis of cdm moieties to deshield PEG shell and expose the positive charges, facilitating DOX endocytosis and IL-12 pDNA transfection in tumor cells for an efficient chemoimmunotherapy combination. DOX kills tumor cells by blocking the cell cycle progression and apoptosis induction. In addition, IL-12 induces the increase in numbers of CD8$^+$ T cells and NK cells, as well as the Treg suppression, to relieve the immunosuppression and enhance the antitumor function of the immune system. Overall, DOX/IL-12 pDNA co-loaded PMet-P(cdmPEG$_{2K}$) micelleplexes generate a synergistic antitumor effect of the chemo-immunotherapy combination treatment.

Figure 17:
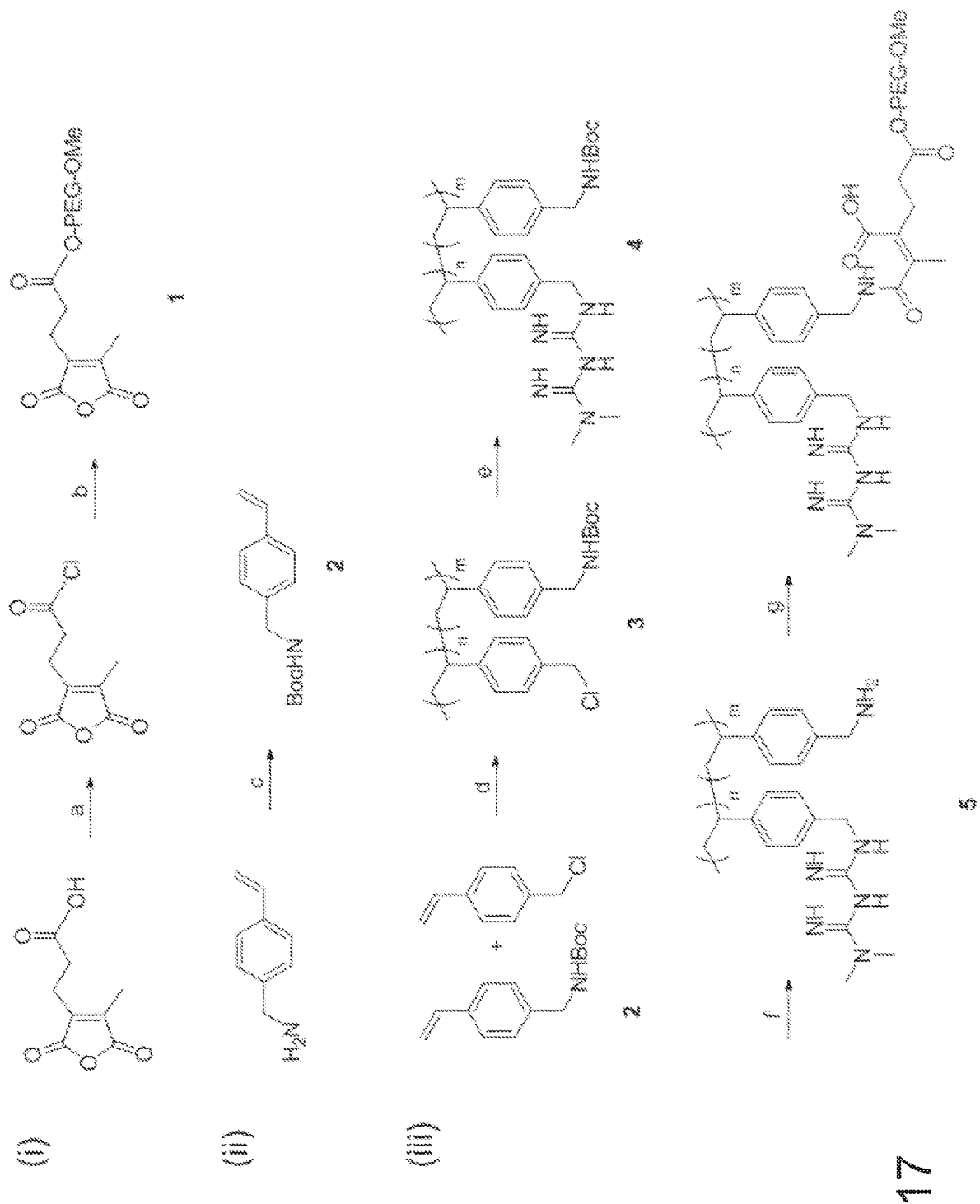
FIG. 17 illustrates an embodiment of the synthesis of a $PMet-P(cdmPEG_{2K})$ polymer hereof.

The PMet-P(cdmPEG$_{2K}$) polymer was synthesized as illustrated in FIG. 17. PEG$_{2K}$ was first reacted with pH-labile cdm to obtain PEG$_{2K}$-cdm (compound 1) according to previous published literature methodology. Compound 3 was synthesized by reversible addition fragment chain transfer (RAFT) polymerization of 4-vinylbenzyl chloride and Boc-protected 4-vinylbenzylamine monomers (compound 2). NMR confirmed that Compound 3 included 85% of 4-vinylbenzyl chloride and 15% of Boc-protected 4-vinyl-benzylamine moieties. MET was then conjugated on compound 3 to obtain compound 4. The Boc-groups of the synthesized compound 4 was deprotected, and amine-bearing compound 5 was obtained and further conjugated with PEG$_{2K}$-cdm through the reaction with cdm anhydride residue. The amide bond of PMet-P(cdmPEG$_{2K}$) was tumor extracellular acid labile and PEG$_{2K}$ would be cleaved to expose cationic PMet micelles at tumor sites, facilitating tumor targeted co-delivery of drugs and genes for efficient chemoimmunotherapy combination.

The chemical structure of PMet-P(cdmPEG$_{2K}$) polymer was confirmed by $^1$H NMR. The average unit numbers of MET per PMet-P(cdmPEG$_{2K}$) molecule, calculated was about 42 by the relative intensity ratio of the methyl protons (b, N—CH$_3$) of MET to the ethylene protons of the benzene ring. The unit number of PEG$_{2K}$ chain was calculated from the relative intensity ratio of the protons (—OCH$_3$) of PEG$_{2K}$ chain to the ethylene protons (—CH=CH—) of the benzene ring, showing around 12 units of PEG$_{2K}$ were conjugated per PMet-P(cdmPEG$_{2K}$) molecule. MET conjugating content on PMet-P(cdmPEG$_{2K}$) polymeric prodrug calculated was about 14% (w/w), exhibiting an excellent MET loading capacity of PMet-P(cdmPEG$_{2K}$) polymeric prodrug.

Met-P(cdmPEG$_{2K}$) polymer had a lower CMC value of 28.6 μg/mL, which suggested the self-assembling behavior of PMet-P(cdmPEG$_{2K}$). As a carrier, micelles of the polymer could maintain stability upon dilution in bloodstream after intravenous injection.

DOX loaded PMet-P(cdmPEG$_{2K}$) micelles were prepared by thin film method and the cationic PMet-P(cdmPEG$_{2K}$) micelles loading with DOX complexed with IL-12 pDNA through electrostatic interaction to prepare the DOX/IL-12 co-loaded micelleplexes. Gel retardation assay was utilized to confirm the micelleplexes formation of blank and DOX-loaded micelles complexed with IL-12 pDNA. The inhibition migration of condensed IL-12 pDNA in agarose gel was observed, indicating a complete formation of IL-12 loaded PMet-P(cdmPEG$_{2K}$) micelleplexes and IL-12/DOX PMet-P(cdmPEG$_{2K}$) co-loaded micelleplexes were achieved at and above N/P ratio of 5. It also indicated the DOX encapsulation in the micellar core had little influence on the gene condensing capacity of micelles, as a result of their similar zeta potentials. In addition, DOX encapsulated in IL-12/DOX co-loaded micelleplexes and DOX loaded PMet-P(cdmPEG$_{2K}$) micelles exhibited a series of opposite migration bands from IL-12 as the N/P ratio increased, owing to the positively charged DOX molecules migrated from micellar cores, which further confirmed that DOX and IL-12 were co-encapsulated in PMet-P(cdmPEG$_{2K}$) micellar system.

Furthermore, the IL-12 pDNA condensing capacities of PMet-P(cdmPEG$_{2K}$) micelles was also evaluated by dynamic light scattering. The average particle size and zeta potential of IL-12 and IL-12/DOX co-loaded micelleplexes at different N/P ratios. The blank and DOX-loaded PMet-P(cdmPEG$_{2K}$) micelles showed an average size of 154 nm and 178 nm (see Table 2 below). PMet-P(cdmPEG$_{2K}$) micelles were able to condense IL-12 pDNA efficiently into a more compact micelleplex structure with a smaller particle size of 100-125 nm and a narrow size distribution above a N/P ratio of 5, which could be favorable for EPR effect mediated tumor tissue accumulation and gene/drug co-delivery via a particle size-dependent endocytosis approach. The more compactable micelleplexes might be a result of the charge neutralization and non-covalent cross-linking of PMet-P(cdmPEG$_{2K}$) micelles by IL-12 pDNA.

Zeta potential of micelles is an important parameter related to the gene condensing ability and in vivo delivery performance. In the case of zeta potential results, blank and DOX-loaded micelles exhibited similar zeta potential of 18.2 and 17.1 mV (Table 2), respectively. The lower zeta potential is a result of the partial shielding by PEG$_{2K}$ on cationic shell of PMet micelles. The zeta potential of IL-12 and IL-12/DOX PMet-P(cdmPEG$_{2K}$) micelleplexes reversed from negative charge to positive charge when the N/P ratio increased to 5, indicating the formation of micelleplexes system. The above particle size and zeta potential results of IL-12 and IL-12/DOX co-loaded micelleplexes were consistent with the gel retardation assay results.

Table 2 also shows the physicochemical properties of IL-12 and IL-12/DOX PMet-P(cdmPEG$_{2K}$) micelleplexes at N/P ratio of 20, at which ratio the in vivo gene transfection and therapeutic efficacy were evaluated. IL-12 and IL-12/DOX PMet-P(cdmPEG$_{2K}$) micelleplexes showed an average size of 103 and 102 nm, and a zeta potential of 10.3 and 10.4 mV, respectively (Table 2). The micelles and micelleplexes observed by TEM all showed compact and spherical morphology. The observed size from TEM was smaller than that from DLS, which was a result of the collapse of micelles during TEM sample preparation processes. In addition, PMet-P(cdmPEG$_{2K}$) micelles exhibited excellent encapsulation performance for DOX, with DLC and DLE of 9.53% and 99.9%, respectively (Table 1).

To verify that the PEG shell could be deshielded from PMet-P(cdmPEG$_{2K}$) micelleplexes at extracellular tumor pH, the pH sensitivity of IL-12 loaded and IL-12/DOX co-loaded micelleplexes was investigated by monitoring the pH-dependent zeta potential in HEPES buffer at pH 7.4 and 6.8. The surface charge of micelleplexes increased significantly from 10.7 mV to 29.8 mV after 4 h incubation at pH 6.8. On the contrary, the zeta potential of micelleplexes showed no significant change after 4 h incubation at pH 7.4. The zeta potential changes may, for example, be attributable to partial detachment of PEG shell from IL-12 and IL-12/DOX PMet-P(cdmPEG$_{2K}$) micelleplexes, and the re-exposure of cationic amino groups on the surface of micelleplexes after cdm linker cleavage under tumor extracellular pH (pH=6.8). The increased positive charges in response to tumor extracellular pH would facilitate the internalization of PMet-P(cdmPEG$_{2K}$) micelleplexes by tumor cells and generate excellent gene transfection and drug delivery performances.

PEGylation of micelles can minimize opsonin adhesion by serum components in blood, thus potentially prolonging the blood circulation time and increasing the tumor tissue accumulation by EPR effect following systemic administration in vivo. To evaluate the blood protein adsorption and interaction, the serum stability of micelles and micelleplex systems were investigated through monitoring the size changes at different time intervals after co-incubation with bovine serum albumin (BSA, 1 mg/mL). "Gold-standard" transfection agent PEI$_{25K}$ complexed with IL-12 gene was investigated as a control for comparison. PMet-P(cdmPEG$_{2K}$) micelles and micelleplex groups showed a slightly increased size after 24 h incubation, but IL-12/PEI$_{25K}$ polyplexes formed a significantly larger aggregates in a short time period after incubation with BSA. These results showed that the positive charge shielding effect of PEG on the PMet-P(cdmPEG$_{2K}$) micellar surface enhanced the serum stability of micelles and micelleplexes after intravenous injection in vivo.

MET amounts released from PMet-P(cdmPEG$_{2K}$) were analyzed for evaluation of the MET cleavage efficiency of polymeric prodrug. The MET achieved highest released amounts from prodrug micelles at 48 h incubation. The cleavage mechanism may, for example, involve the enzymatic hydrolysis of carbon-carbon bonds between MET and compound 3. However, blank micelles and IL-12 loaded PMet-P(cdmPEG$_{2K}$) micelleplexes did not exhibit notable tumor cell proliferation inhibition activity against 4T1.2 cells after 72 h incubation. It is possible that the intracellular enzyme in cultured tumor cells was not effective for hydrolyzing MET completely from PMet-P(cdmPEG$_{2K}$) prodrug carrier, which was not sufficient for generating effective antitumor activity. However, the in vivo enzyme condition at

TABLE 2

| Micelles | Mass ratio (mg:mg) | N/P ratio | Size (nm) | Zeta potential (mV) | DLC (%) | DLE (%) | Stability (d) |
|---|---|---|---|---|---|---|---|
| PMet-P(cdmPEG$_{2K}$) | — | — | 154 | 18.2 | — | — | — |
| IL-12 PMet-P(cdmPEG$_{2K}$) | — | 20 | 103 | 10.3 | — | — | 10 |
| DOX PMet-P(cdmPEG$_{2K}$) | 10:1 | — | 178 | 17.1 | 95.3 | 9.53 | 7 |
|  | 20:1 | — | 174 | 14.7 | 98.2 | 4.91 | 7 |
|  | 30:1 | — | 162 | 16.0 | 99.9 | 3.33 | 8 |
| IL-12/DOX PMet-P(cdmPEG$_{2K}$) | — | 20 | 102 | 10.4 | 95.3 | 9.53 | 6 | the tumor site is different from and more complicated than that of cultured tumor cells. A more effective MET release from the PMet-P(cdmPEG$_{2K}$) polymeric prodrug may be expected, and that release may generate a more effective anti-tumor activity, displaying synergistic antitumor effect with DOX in vivo.

Cytotoxicities results indicated significant anti-tumor activity of PMet-P(cdmPEG$_{2K}$) micelleplexes co-delivering IL-12 pDNA and DOX. To further illustrate that the chemotherapeutic agent and gene co-encapsulated into PMet-P (cdmPEG$_{2K}$) micelles could be co-delivered simultaneously into tumor cells, the intracellular co-delivery of DOX and FAM-labeled siRNA by PMet-P(cdmPEG$_{2K}$) micelles was observed by confocal laser scanning microscopy (CLSM). FAM-siRNA loaded micelleplexes and DOX-loaded micelles only showed green fluorescence signal of FAM-siRNA and red fluorescence signal of DOX, respectively. However, both red fluorescence signal of DOX and green fluorescence signal of FAM-siRNA was observed in double fluorescence-labeled FAM-siRNA/DOX co-loaded PMet-P (cdmPEG$_{2K}$) micelleplexes. For FAM-siRNA/DOX co-loaded PMet-P(cdmPEG$_{2K}$) micelleplexes, DOX fluorescence signals were mainly appeared in nuclei, and FAM-siRNA fluorescence signals were found to be localized largely in perinuclear region of cells. It was demonstrated that DOX and FAM-siRNA could be co-loaded and co-delivered into same 4T1.2 cells simultaneously by PMet-P (cdmPEG$_{2K}$) micellar system.

Intracellular uptake and distribution of DOX-loaded micelles and IL-12/DOX co-loaded PMet-P(cdmPEG$_{2K}$) micelleplexes was investigated by CLSM. After 4 h incubation, a much stronger intracellular fluorescence signal of DOX loaded micelles and IL-12/DOX co-loaded micelleplexes was observed at pH 6.8 than those at pH 7.4, and DOX fluorescence was mainly localized in the nuclei. PEG deshielding in tumor extracellular pH (pH=6.8) re-exposed the positive charge of micelles and facilitated adherence to negatively charged cellular membranes, promoting the internalization and DOX release of micelles. In contrast, the internalization of DOX solution was not significantly affected by pH, which showed slightly stronger fluorescence signal compared with DOX loaded micelles formulations because of the rapid passive diffusion of free DOX. In addition, compared to DOX-loaded micelles, the smaller size of IL-12/DOX co-loaded PMet-P(cdmPEG$_{2K}$) micelleplexes facilitated the endocytosis pathway, and showed an increased cellular uptake.

The intracellular uptake and trafficking results indicated the PEG deshielding property of PMet-P(cdmPEG$_{2K}$) micelleplexes under tumor intracellular condition led to the increased intracellular DOX and IL-12 pDNA co-internalization, which would improve the therapeutic efficacy of the combined chemoimmunotherapy.

To evaluate the potential application of PMet-P (cdmPEG$_{2K}$) micelles for gene delivery, in vitro gene transfection efficiency was evaluated against 4T1.2 cells by loading EGFP or luciferase-encoding pDNA. To investigate the optimized N/P ratio of PMet-P(cdmPEG$_{2K}$) micelles for gene delivery and expression, the transfection efficiency of PMet-P(cdmPEG$_{2K}$) micelles were quantitative performed with luciferase reported gene (luc-pDNA) at various N/P ratios firstly. Luc pDNA/PEI$_{25K}$ polyplexes was used as the positive control for comparison. The luc pDNA/PEI$_{25K}$ polyplexes showed the best luciferase gene expression level at N/P ratio of 20. The luciferase expression of luc pDNA/ PMet-P(cdmPEG$_{2K}$) micelleplexes were significantly enhanced with increasing N/P ratios, reaching the highest efficiency at N/P ratio of 20. Further increase of the N/P ratio up to 40 showed decreased transfection efficiency for luc pDNA/PMet-P(cdmPEG$_{2K}$) micelleplexes. At pH 7.4, PEI$_{25K}$ exhibited a superior luc-pDNA transfection efficiency, which was about 10-fold higher than that of PMet-P(cdmPEG$_{2K}$) micelles. However, at pH 6.8, the luc-pDNA/ PEI polyplexes exhibited a marked decreased in luciferase expression level. To the contrary, an increased transfection level and a significantly higher expression level was founded in luc-pDNA/PMet-P(cdmPEG$_{2K}$) micelleplexes compared to incubation at pH 7.4.

The gene expression efficiency was also qualitative evaluated using a plasmid encoding EGFP report gene. The fluorescence images showed similar results to the measured data of luciferase pDNA expression. The gene transfection results showed that deshielding of the PEG layer of PMet-P(cdmPEG$_{2K}$) micelles under tumor extracellular pH (pHe 6.8) conditions led to more EGFP or luciferase encoding gene being delivered and transfected into the cultured cells, further improving the EGFP/luc pDNA expression. With significant EGFP/luc encoding gene delivery and transfection performance, PMet-P(cdmPEG$_{2K}$) micelles at N/P ratio of 20 were further studied as a co-delivery system for DOX and IL-12 pDNA for immunotherapy and chemotherapy combination via in vitro and in vivo experiments.

To evaluate the potential efficiency of PMet-P (cdmPEG$_{2K}$) micelles for tumor acidity-targeting gene delivery in vivo, the transfection and GFP expression efficiency was examined in liver, tumor and lung after 24 h intravenous injection of PEI$_{25K}$ and PMet-P(cdmPEG$_{2K}$) micelles carrying EGFP pDNA in 4T1.2 tumor-bearing mice. The mice only treated with Hoechst 33342 and the mice treated with EGFP pDNA in saline solution via hydrodynamic injection at an EGFP pDNA dose of 25 μg/mice were used as negative and positive control, respectively.

The negative control group did not show any detectable green fluorescence in all organs. Bright GFP fluorescence spots were presented in liver tissues, and negligible fluorescence signal was observed in tumor and lung of the positive control group treated with naked EGFP pDNA through hydrodynamic injection. Liver tissues of mice treated with EGFP/PMet-P(cdmPEG$_{2K}$) micelleplexes showed very few fluorescence spots, while much more GFP fluorescence signals were observed in EGFP/PEI$_{25K}$ polyplexes groups in liver. The shielding PEG on the surface of PMet-P(cdmPEG$_{2K}$) micelles could prevent plasma opsonins absorption and avoid the uptake of reticuloendothelial system (RES), thus prolonging the blood circulation of micelleplexes and decreasing accumulation in liver tissue.

Weak GFP fluorescence was detected in the tumor for the EGFP/PEI$_{25K}$ polyplexes treated mice. As a comparison, EGFP/PMet-P(cdmPEG$_{2K}$) micelleplexes induced an evidently higher level of GFP expression in tumor. The prolonged blood circulation promoted the tumor accumulation of PMet-P(cdmPEG$_{2K}$) micelleplexes via EPR effects, and the PEG deshielding micelleplexes under extracellular tumor acid environment could further efficiently deliver EGFP pDNA to the tumor cells and release the loaded pDNA for GFP expression.

Much more and intense GFP expression was observed in the lung of the mice treated with EGFP/PEI$_{25K}$ polyplexes. The positively charged EGFP/PEI$_{25K}$ polyplexes may, for example, be primarily delivered to the lung of mice in vivo. In contrast, a decreased GFP expression in lung was observed for PMet-P(cdmPEG$_{2K}$) micelleplexes, which might be contributed to the efficient positive charged shielding effect of micelleplexes by PEG layer.

The in vivo EGFP pDNA transfection results indicated potent in vivo gene delivery of PMet-P(cdmPEG$_{2K}$) micelles for targeted tumor therapy application. It is expected that IL-12 pDNA would exhibit significant IL-12 cytokine expression performance after intravenous injection into mice carried by PMet-P(cdmPEG$_{2K}$) micelles, generating potent immunostimulatory effect for tumor immunotherapy, and producing synergistic effect with DOX for chemoimmunotherapy combination.

Combination of cytotoxic drugs and immunostimulatory agents such as cytokines in chemoimmunotherapy provides a novel approach for cancer therapy. To evaluate the chemoimmunotherapy efficiency of IL-12-encoding pDNA and DOX co-loaded and co-delivered by PMet-P(cdmPEG$_{2K}$) micelles, the in vivo therapeutic efficacy was studied using 4T1.2 tumor bearing mice. Compared to the saline group, all the treatment groups exhibited tumor growth inhibition activity. Moreover, the co-delivery of DOX with IL-12 pDNA using PMet-P(cdmPEG$_{2K}$) micelles suppressed tumor growth more efficiently than the delivery of either DOX or IL-12 by PMet-P(cdmPEG$_{2K}$) micelles. The tumor growth inhibition rate for the treated groups of IL-12 micelleplexes, DOX-loaded micelles and IL-12/DOX co-loaded micelleplexes were calculated to be 28.7%, 41.0% and 66.5%, respectively, after 18 days past the first injection. The superior tumor growth inhibition activity of IL-12/DOX co-loaded micelleplexes suggested a significant synergistic/combined antitumor effect was achieved for DOX and IL-12 pDNA co-delivered by PMet-P(cdmPEG$_{2K}$) micelles.

The evaluation of systemic toxicity is essential for systemic drug delivery of micellar systems. The body weight of mice in different treatment groups was also monitored after first injection. The body weight increased obviously as time prolonged for saline and IL-12 loaded micelleplexes treated groups, which might be a result of the mice of those two groups bearing larger tumor size. However, the mice treated with DOX loaded micelles and IL-12/DOX co-loaded micelleplexes displayed a slight body weight increase. These results indicate that PMet-P(cdmPEG$_{2K}$) micelles were well-tolerated for DOX and IL-12 pDNA co-delivery in vivo.

Although DOX was loaded into micelle formulations hereof in a number of representative embodiments, numerous small molecule compounds such as drugs may be used in the present formulations. Table 3 below, for example, provides a summary of several of the small molecule drugs that have been loaded into PMet-P(cdmPEG$_{5K}$) formulations hereof.

TABLE 3

| Micelles * | Mass Ratio | Particle Size (nm) | DLC (%) |
|---|---|---|---|
| Pmet-P(cdm PEG$_{5K}$) | | 142 | |
| Pmet-P(cdm PEG$_{5K}$):Doxrubicin | 10:1 | 133 | 9.09% |
| Pmet-P(cdm PEG$_{5K}$):Paclitaxel | 10:1 | 140 | 9.09% |
| Pmet-P(cdm PEG$_{5K}$):Docetaxel | 10:1 | 144 | 9.09% |
| Pmet-P(cdm PEG$_{5K}$):Erlotinib | 10:1 | 146 | 9.09% |
| Pmet-P(cdm PEG$_{5K}$):Imatinib | 10:1 | 138 | 9.09% |
| Pmet-P(cdm PEG$_{5K}$):Curcumin | 5:1 | 104 | 16.6% |
| Pmet-P(cdmPEG$_{5K}$):10058-F4 | 20:1 | 137 | 4.80% |

* Micelles were complexed with IL 12 plasmid at a N/P ratio of 20:1

Nanocarriers hereof exhibit the ability to safely co-deliver both small molecule drugs and nucleic acid-based therapeutics. As described above, most chemotherapeutic drugs are poorly water-soluble, while nucleic-acid based therapeutics are polyanionic molecules with high water-solubility, instability and high molecular weight. Most reported carriers are designed for delivery of either small molecule drugs or nucleic acid therapeutics alone. The few carriers which have been described for codelivery of the two different types of therapeutics often involved complicated preparation process.

Representative Experimental Procedures

Materials and Reagents. Doxorubicin (>99%) was purchased from LC Laboratories (MA, USA). Dicyclohexylcarbodiimide (DCC) was purchased from Alfa Aesar (MA, USA). 4-(Dimethylamino) pyridine (DMAP) was purchased from Calbiochem-Novabiochem Corporation (CA, USA). Creatine, vinylbenzyl chloride, 4-Cyano-4-(phenylcarbonothioylthio)pentanoic acid, oligo(ethylene glycol) methacrylate OEGMA (average Mn=500), 2,2-Azobis(isobutyronitrile) (AIBN), trypsin-EDTA solution, 3-(4,5-dimethylthiazol-2-yl)-2,5-di phenyl tetrazolium bromide (MTT), metformin hydrochloride, monomethoxy PEG$_{2K}$, branched and linear polyethyleneimine (PEI, MW=25 kDa), triton X-100, hoechst 33342, lysotracker Green DND-26, FAM-labeled siRNA, AF647-labeled siRNA and Dulbecco's Modified Eagle's Medium (DMEM) were all purchased from Sigma-Aldrich (MO, U.S.A.). Opti-MEM medium was purchased from Invitrogen (Carlsbad, USA). AIBN was purified by recrystallization in anhydrous ethanol. Fetal bovine serum (FBS), TRIzol lysis reagent and penicillin-streptomycin solution were purchased from Invitrogen (New York, U.S.A.). Vinylbenzylamine, 2-propionic-3-methylmaleic anhydride (cdm) were obtained from TCI America (Portland, Oreg. USA). QuantiTect Reverse Transcription Kit was purchased from Qiagen (MD, U.S.A). All solvents used in this study were HPLC grade.

EGFP expression plasmid pEGFP-N$_2$ and luciferase expression plasmid luc-pDNA were propagated in competent *Escherichia coli* DH5α cells. IL-12 pDNA and control pDNA were supplied by Shulin Li's Lab. The IL-12 pDNA construct was obtained from Valentis, Inc. The control pDNA used for in vivo study consisted of a deletion of the IL-12 pDNA from the IL-12 construct. All endotoxin-free pDNA were prepared using the endotoxin free Plasmid Maxiprep Kit according to the manufacturer's instructions.

Synthesis of VBMor monomer. Vinylbenzyl chloride (167.2 mg, 1.1 mM), morpholine (95.8 mg, 1.1 mM) and K$_2$CO$_3$ (0.69 g, 5 mM) were dissolved in 6 mL DMF and stirred at 50° C. for 6 h. After cooling down to room temperature, 20 mL water was added to the mixture, followed by three times extraction with 50 mL CH$_2$Cl$_2$. After evaporation of CH$_2$Cl$_2$, the crude product was purified by column chromatography with petroleum ether/ethyl acetate (v/v, 4/1~2/1) as the elution liquid. VBMor monomer was obtained with a 71% yield.

Synthesis of POEG-st-Pmor polymer. VBMor monomer (228.8 mg, 1.13 mmol), OEG500 (100 mg, 0.20 mmol), AIBN (1 mg, 0.0062 mmol), 4-Cyano-4-(phenylcarbonothioylthio)pentanoic acid (4 mg, 0.014 mmol), and 1 mL of dried tetrahydrofuran were added into a Schlenk tube, and deoxygenated by free-pump-thawing for three times. Then the mixture was filled with N$_2$ and immersed into an oil bath thermostated at 80° C. to start the polymerization. After 24 h, the reaction was quenched by immersing the tube into liquid nitrogen and the mixture was precipitated in hexane for 3 times. The product POEG-st-Pmor was obtained after vacuum drying.

Preparation and characterization of IL-36γ Plasmid/DOX-co-formulated micelles. DOX-loaded POEG-st-Pmor micelles were prepared by the dialysis method. Briefly, 10 mg of polymer was dissolved in 5 mL of DMSO and mixed with 100 μL of DOX DMSO solution (10 mg/ml). To remove free DOX from the DOX-incorporated micelles, the solution was dialyzed against PBS using dialysis membrane with a MW cutoff of 3,500. The solution was lyophilized and resolubilized in 1 mL PBS. Drug-free micelles were similarly prepared. For plasmid DNA complexation, polymeric micelles were diluted to different concentrations in water and mixed with plasmid DNA solution to obtain the desired N/P ratios. This mixture was allowed to incubate at RT for 20 min prior to further characterization.

In vitro characterization of POEG-st-Pmor polymer. The structure and molecular weight of POEG-st-Pmor polymer was characterized by $^1$H NMR and gel permeation chromatography (GPC) similarly conducted as previously reported. The particle size and zeta potential of POEG-st-Pmor polymer were determined by dynamic light scattering (Nano-ZS 90, Malvern Instruments, Malvern, UK). The morphology of POEG-st-Pmor polymers was observed under a transmission electron microscope (TEM). The micelles were placed on a copper grid covered with nitrocellulose. The samples were negatively stained with phosphotungstic acid and dried at room temperature before measurement.

Drug loading capacity (DLC) and drug loading efficiency (DLE) were determined as described before. The amount of DOX loaded in the micelles was determined by high performance liquid chromatography (HPLC, Shimadzu LC-20AD, Japan). The DLC of DOX/micelles was calculated using the equation: DLC=Drug incorporated/(input polymer+Drug)×100%

Critical micelle concentration (POEG-st-Pmor). The critical micellar concentration (CMC) was determined using Nile Red as a fluorescence probe. Micelles of various concentrations (0.0001 to 1 mg/mL) were first prepared. Two microliter of a Nile Red solution in acetone (0.97 mg/mL) were then added to each sample and acetone was evaporated prior to fluorescence measurements using a microplate reader. Fluorescence from emission wavelength ranging from 560 to 750 nm was recorded with an excitation wavelength of 550 nm.

In vitro drug release study for POEG-st-Pmor micelles. The in vitro DOX release kinetics for the POEG-st-Pmor micelles was determined by a dialysis method. Briefly, 0.5 ml of DOX-loaded micelles and micelles co-loaded with DOX and IL-36γ plasmid at a DOX concentration of 0.5 mg/mL were placed into a dialysis bag (MW cutoff 3,500), respectively. The dialysis bag was incubated in 100 mL PBS with gentle shaking at 37° C. Two ml of PBS solution outside of the dialysis bag was collected at different time points and equal amount of fresh PBS was added back. The concentrations of released DOX were determined by HPLC.

Gel retardation assay. Plasmid/polymer complexes were prepared at different N/P ratios, ranging from 0.1 to 20 (plasmid DNA concentration was fixed at 5 mg/ml). The resulting complexes were then electrophoresed on a 1% agarose gel in TAE buffer at 120 mV for 30 min, and visualized using a UV illuminator with ethidium bromide staining. Free plasmid DNA was used as a control.

Cell culture and animals. The murine breast cancer cell line 4T1.2 was cultured in DMEM medium supplemented with 10% FBS and 1% penicillin/streptomycin at 37° C. in 5% $CO_2$ atmosphere. Female BALB/c mice (4-6 weeks, Charles River, Davis, Calif.) were housed under pathogen-free conditions according to AAALAC guidelines. The mice related experiments were performed following institutional guidelines and approved by the Animal Use and Care Administrative Advisory Committee at the University of Pittsburgh.

In vitro cytotoxicity. The cytotoxicity of DOX-formulated POEG-st-Pmor micelles, IL-36γ plasmid-complexed micelles and DOX+IL-36γ plasmid-co-loaded micelles were assessed in 4T1.2 breast cancer cells and compared to free DOX. Briefly, 4T1.2 cells (2,000 cells/well) were seeded in 96-well plates for overnight and were treated with various concentrations of DOX formulations for 72 h. MTT solution was added to each well and MTT formazan was solubilized by DMSO after 2 h of incubation. The absorbance in each well was measured by a microplate reader at a wavelength of 570 nm. Cell viability was calculated as $[(OD_{treat}-OD_{blank})/(OD_{control}-OD_{blank})\times100\%]$. The cytotoxicity of POEG-st-Pmor micelles alone was similarly tested in 4T1.2 cells as described above.

Stability of the micelles in BSA. BSA was used to simulate the blood physiological environment to investigate the stability of POEG-st-Pmor micelle complexes under the mimicked physiological conditions. Plasmid DNA/micelle complexes and plasmid DNA+DOX/micelle complexes were prepared as described above and incubated with BSA (30 mg/ml). pDNA/PEI complexes were used as a control. Sizes of complexes were followed at different time points as an indication of stability.

In vitro plasmid transfection. 4T1.2 cells were seeded in a 96-well plate and incubated for 24 h until cells were 80% confluent. Cells were then transfected with EGFP plasmid/POEG-st-Pmor complexes (N/P=20) and EGFP plasmid/PEI (N/P=20) complexes in serum-free opti-DMEM medium. After 4 h incubation, transfection medium was removed and 100 μL of fresh complete medium were added to each well. PBS group was used as a control. After 48 h, the transfected cells were observed under a fluorescence microscope (OLYMPUS America, Melville, N.Y.).

In vivo fluorescence imaging. Female Balb/C mice bearing 4T1.2 tumor (~400 mm$^3$) in the mammary fat pad were used to investigate the biodistribution and in vivo transfection efficiency of our micellar carriers.

The in vivo transfection efficiency of POEG-st-Pmor micellar carriers was evaluated with EGFP plasmid as a reporter gene. Linear PEI was used to as control. Various formulations were i.v. injected into tumor-bearing mice at a dose of 50 μg plasmid per mouse. One day later, mice were injected with 1 μg of Hoechst and sacrificed one hour later. The fluorescence signal of EGFP in the cryosections was examined under a confocal microscope.

Mouse model of breast cancer lung metastasis. Female Balb/c mice were injected with 2×10$^5$ 4 T1.2 cells through the tail vein. Five days after tumor cell injection, mice were randomly divided into 6 groups. POEG-st-Pmor was chosen as a representative carrier system for codelivery of IL-36γ plasmid and DOX. Animals were treated intravenously with free POEG-st-Pmor micelles, IL-36γ plasmid/POEG-st-Pmor micelles, DOX+control plasmid/POEG-st-Pmor micelles and DOX+IL-36γ plasmid/POEG-st-Pmor micelles every three days for three times. The PBS treatment group was used as control. DOX dosage was 5 mg/kg and plasmid dosage was 50 μg per mouse. Lung tissues were harvested and weighted 11 days after the first injection. Pulmonary metastases were enumerated by intra-tracheal injection of India ink solution. India ink-injected lungs were washed in Feket's solution (300 ml 70% EtOH, 30 ml 37% formaldehyde and 5 ml glacial acetic acid) and white tumor nodules against a dark blue lung background were counted.

Histopathological analysis. The lung tissues were harvested and fixed in 10% formalin after the above treatments. The fixed samples were then embedded in paraffin and the tissue sections were stained with hematoxylin/eosin and analyzed for the presence of metastases under microscope. The total number of metastases per lung section was counted in different treatment groups.

Analysis of tumor-infiltrating lymphocytes and myeloid-derived suppressor cells. Lung tissues were collected in serum free RPMI medium and cut mechanically with scissors. Liberase TL (0.3 mg/ml) and DNase I (0.3 mg/ml) were used to digest the lung tissues and tumor nodules. Tissues were further grinded and filtered through a 40-mm cell strainer. TILs and MDSC cells were further purified and stained with fluorescence-labeled antibody for flow cytometry analysis using a FACS flow cytometer.

Synthesis of POEG-st-PVBC polymer, OEG500 (550 mg, 1.1 mmol), VBC monomer (600 μL, 4.27 mmol), 4-Cyano-4-(phenylcarbonothioylthio) pentanoic acid (8 mg, 0.0286 mmol), AIBN (3 mg, 0.0186 mmol), and 1 mL of dried tetrahydrofuran were added into a Schlenk tube, and deoxygenated by free-pump-thawing for three times. Then the mixture was filled with $N_2$ and immersed into an oil bath thermostated at 82° C. to start the polymerization. After 16 h, the reaction was quenched and the mixture was precipitated in hexane for 3 times. The product POEG-PVBC was obtained after vacuum drying. Conversion of OEG500 monomer was 66.0% and conversion of VBC monomer was 80.0%.

Synthesis of POEG-st-PCre polymer. The POEG-PVBC polymer (270 mg) and creatine (1 g) were mixed in 15 mL anhydrous DMF with $K_2CO_3$ (1 g). After stirring at 80° C. for 36 h, the reaction mixture was cooled down and transferred into a dialysis bag (MWCO=3500 Da). After dialysis against a dilute hydrochloric acid solution for 1 day and deionized water for 3 days, the solution in the dialysis bag was centrifuged at 4,500 rpm for 12 min and the supernatant was lyophilized to give the POEG-PCre polymer. $^1H$ NMR spectra were examined on a 600.0 MHz Bruker spectrometer using DMSO-$d_6$ as the solvent.

Preparation of DOX+tRNA-mir-34a co-formulated DOX solution was first prepared by dissolving DOX.HCl in DMSO containing triethylamine (5 equiv) overnight to remove HCl. DOX-loaded POEG-PCre micelles were prepared by the dialysis method. Briefly, 2 mg of polymer was dissolved in 200 uL DMSO and mixed with 20 uL of DOX solution (10 mg/mL). The mixture was then dialyzed against distilled deionized (DD) water using a dialysis bag (MWCO=3500) overnight to remove the unloaded free DOX. Drug-free micelles were similarly prepared without adding DOX solution. For tRNA-mir-34a complexation, polymeric micelles were diluted to different concentrations in DD water and mixed with the equivalent volume of tRNA-mir-34a (in 10% of glucose) to obtain the desired N/P ratios. This nanocomplexes was allowed to incubate at RT for 20 min prior to further characterization. In vitro studies were performed with freshly prepared nanocomplexes. For in vivo studies, micelles and tRNA-mir-34a were first mixed in DD water for 20 min, and then lyophilized with glucose as a cryoprotectant.

Synthesis of polymetformin (PMet) polymer. 4-Vinylbenzyl chloride (1.27 g), compound 2 (354 mg) of FIG. 17, AIBN (3 mg), 4-cyano-4-[(dodecylsulfanylthiocarbonyl) sulfanyl] pentanoic acid (24 mg), and 1 mL of dried tetrahydrofuran were added into a Schlenk tube, and deoxygenated by free-pump-thawing for three times. Then the mixture was filled with $N_2$ and immersed into an oil bath thermostated at 90° C. to start the polymerization. After 24 h, the reaction was quenched by immersing the tube into liquid nitrogen and the mixture was dialyzed against DMSO and distilled water for 2 days, respectively. The compound 3 with 85% of vinylbenzyl chloride and 15% of Boc-protected 4-vinylbenzylamine was obtained after precipitation. Metformin hydrochloride (1.65 g), compound 3 (150 mg) and N, N-diisopropylethylamine (1.35 mL) were added in DMSO (4.8 mL), and then the mixture was stirred for 48 h at 110° C. Reaction mixture was dialyzed against 0.5% hydrochloride solution and distilled water for 2 days, respectively. PMet with 15% Boc-protected 4-vinylbenzylamine (Boc-PMet) (compound 4) was obtained after lyophilization. The Boc-PMet (compound 4) polymer was deprotected at room temperature in DMSO/TFA (1/1, v/v) mixture for 2 h, and then dialyzed against distilled water for 2 days. The Boc-deprotected PMet product with 15% free amino group (compound 5) was obtained after lyophilization.

Synthesis of PMet-P(cdmPEG$_{2K}$) polymer. PMet-P (cdmPEG$_{2K}$) was synthesized by a ring opening reaction of PEG$_{2K}$-cdm and pMet polymers. Boc-deprotected PMet (compound 5 of FIG. 17, 100 mg) and PEG$_{2K}$-cdm (compound 1, 303 mg) were dissolved in 4 mL of DMSO and stirred at 37° C. for 24 h. The mixture was dialyzed against DMSO and distilled water for 2 days, respectively. The final products of PMet-P(cdmPEG$_{2K}$) polymer was obtained after lyophilization. $^1H$ NMR spectrum was analyzed on a Varian-400 FT-NMR spectrometer at 400 MHz with DMSO-$d_6$ and CDCl$_3$ as the solvent.

Preparation of micelles with PMet-P(cdmPEG$_{2K}$) polymer. Blank and DOX loaded PMet-P(cdmPEG$_{2K}$) micelles were prepared by thin film hydration method. Briefly, DOX (5 mg/mL in 1:1(v/v) of DCM/methanol) and (10 mg/mL in DCM) at designated mass ratios were mixed in a glass tube, and organic solvent was removed through a gentle stream of nitrogen, followed by drying in vacuum for 1 h. The obtained thin-film of PMet-P(cdmPEG$_{2K}$)/DOX mixture was hydrated in HEPES buffer solution (10 mM, pH 7.4), forming a clear solution of DOX-loaded PMet-P (cdmPEG$_{2K}$) micelles. The blank micelles were prepared by the same procedure as described above except for no DOX adding.

For IL-12 loaded micelleplexes and IL-12/DOX co-loaded micelleplexes preparation, desired amounts of IL-12 pDNA mixed with equal volume of blank micelles or DOX-loaded PMet-P(cdmPEG$_{2K}$) micelles (the DLC (w/w) was about 9%) solutions at various N/P ratios (the ratios of the number of amino groups in PMet-P(cdmPEG$_{2K}$) to the number of phosphate groups in IL-12 pDNA), and the resultant mixture was further incubated at room temperature for 20 min.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A formulation, comprising: a plurality of polymers comprising a hydrophobic polymer backbone formed via radical polymerization, a first plurality of pendant groups attached to the hydrophobic polymer backbone and comprising at least one cationic group, and a second plurality of pendant groups attached to the hydrophobic polymer backbone and comprising at least one hydrophilic polymer, wherein the first plurality of pendant groups is attached to the hydrophobic polymer backbone via a first linking group comprising at least a first aromatic group which is interactive via π-π stacking and the second plurality of pendant groups is attached to the hydrophobic polymer backbone via a second linking group comprising at least a second aromatic group which is interactive via π-π stacking,
- a first therapeutic compound, and
- a second therapeutic compound, wherein the second therapeutic compound is different from the first therapeutic compound and comprises a nucleic acid.

2. The formulation of claim 1 wherein the first therapeutic compound is a small molecule therapeutic compound.

3. The formulation of claim 2 wherein the first therapeutic compound has a molecular weight below 1 kDa.

4. The formulation of claim 3 wherein the second therapeutic compound comprises RNA or DNA.

5. The formulation of claim 3 wherein the second therapeutic compound is a gene or siRNA.

6. The formulation of claim 3 wherein the first therapeutic compound is a chemotherapeutic compound.

7. The formulation of claim 1 wherein the at least a first aromatic group which is interactive via π-π stacking is a benzyl group.

8. The formulation of claim 1 wherein the at least a first aromatic group which is interactive via π-π stacking comprises a benzyl group and the at least a second aromatic group which is independently interactive via π-π stacking independently comprises a benzyl group.

9. The formulation of any one of claims 1 through 8 wherein the hydrophobic polymer backbone is formed via radical polymerization of vinyl monomers.

10. The formulation of claim 9 wherein the hydrophobic polymer backbone is formed via a free radical polymerization.

11. The formulation of claim 9 wherein the hydrophobic polymer backbone is formed via a reversible-deactivation radical polymerization.

12. The formulation of any one of claims 1 through 8 wherein the at least one cationic group comprises an inherently cationic group or a group which forms a cation in vivo.

13. The formulation of claim 12 wherein the group which forms a cation in vivo is an amine group, wherein the amine group is an acyclic amine group, a cyclic amine group or a heterocyclic amine group.

14. The polymer of claim 13 wherein the amine group is selected from the group consisting of a metformin group, a morpholine group, a piperazine group, a pyridine group, a pyrrolidine group, piperidine, a thiomorpholine, a thiomorpholine oxide, a thiomorpholine dioxide, imidazole, guanidine or creatine.

15. The formulation of any one of claims 1 through 8 wherein the second plurality of pendant groups is attached to the hydrophobic polymer backbone via a linking moiety that is labile in vivo and optionally labile under acidic pH conditions.

16. A formulation for delivery of compounds in vivo comprising a plurality of polymers comprising a hydrophobic polymer backbone formed via radical polymerization, a first plurality of pendant groups attached to the hydrophobic polymer backbone and comprising at least one cationic group, and a second plurality of pendant groups attached to the hydrophobic polymer backbone and comprising at least one hydrophilic polymer, wherein the first plurality of pendant groups is attached to the hydrophobic polymeric backbone via a first linking group comprising at least a first aromatic group which is interactive via π-π stacking and the second plurality of pendant groups is attached to the hydrophobic polymer backbone via a second linking group comprising at least a second aromatic group which is interactive via π-π stacking, and
- a plurality of nucleic acid compounds.

17. The formulation of claim 16 wherein the plurality of polymers form micelles.

18. The formulation of claim 17 wherein the plurality of nucleic acid compounds interact with cationic groups of the first plurality of pendant groups.

19. A method of formulating a composition for delivery of a first therapeutic compound and a second therapeutic compound to a patient, wherein the second therapeutic compound is different from the first therapeutic compound and comprises a nucleic acid, comprising: mixing a plurality of polymers comprising a hydrophobic polymer backbone formed via radical polymerization, a first plurality of pendant groups attached to the hydrophobic polymer backbone and comprising at least one cationic group, and a second plurality of pendant groups attached to the hydrophobic polymer backbone and comprising at least one hydrophilic polymer with a plurality of the first therapeutic compounds and with a plurality of the second therapeutic compounds.

* * * * *